(12) United States Patent
Bovin et al.

(10) Patent No.: US 10,919,941 B2
(45) Date of Patent: Feb. 16, 2021

(54) FUNCTIONAL LIPID CONSTRUCTS

(71) Applicant: KODE BIOTECH LIMITED, Auckland (NZ)

(72) Inventors: Nicolai Vladimirovich Bovin, Moscow (RU); Stephen Micheal Henry, Auckland (NZ); Igor Leonidovich Rodionov, Moscow (RU); Cristina-Simona Weinberg, Rotorua (NZ); Alexander Borisovich Tuzikov, Moscow (RU)

(73) Assignee: KODE BIOTECH LIMITED, Auckland (NZ)

( * ) Notice: Subject to any disclaimer, the term of this patent is extended or adjusted under 35 U.S.C. 154(b) by 301 days.

(21) Appl. No.: 15/350,792

(22) Filed: Nov. 14, 2016

(65) Prior Publication Data
US 2017/0218027 A1    Aug. 3, 2017

Related U.S. Application Data

(63) Continuation-in-part of application No. 14/172,346, filed on Feb. 4, 2014, now Pat. No. 9,802,981, which is a continuation of application No. 12/734,072, filed as application No. PCT/NZ2008/000266 on Oct. 13, 2008, now Pat. No. 8,669,084.

(30) Foreign Application Priority Data

| Oct. 12, 2007 | (NZ) | 562475 |
|---|---|---|
| Jun. 6, 2008 | (NZ) | 569024 |
| Jun. 10, 2008 | (NZ) | 569059 |
| Jul. 7, 2008 | (NZ) | 569912 |
| Jul. 18, 2008 | (NZ) | 569964 |
| Nov. 11, 2015 | (AU) | 2015904655 |

(51) Int. Cl.
| C07K 9/00 | (2006.01) |
|---|---|
| C07F 9/10 | (2006.01) |
| C07K 7/08 | (2006.01) |
| C07K 7/06 | (2006.01) |
| A61K 47/54 | (2017.01) |
| C07F 9/6561 | (2006.01) |
| A61K 47/65 | (2017.01) |
| G01N 33/80 | (2006.01) |
| C07F 9/572 | (2006.01) |

(52) U.S. Cl.
CPC ............ *C07K 9/001* (2013.01); *A61K 47/544* (2017.08); *A61K 47/65* (2017.08); *C07F 9/106* (2013.01); *C07F 9/572* (2013.01); *C07F 9/6561* (2013.01); *C07K 7/06* (2013.01); *C07K 7/08* (2013.01); *G01N 33/80* (2013.01)

(58) Field of Classification Search
CPC ....... A61K 47/544; A61K 47/65; C07F 9/106; C07F 9/572; C07F 9/6561; C07K 7/06; C07K 7/08; C07K 9/001; G01N 33/80
See application file for complete search history.

(56) References Cited

U.S. PATENT DOCUMENTS

| 8,669,084 B2 | 3/2014 | Bovin | 435/173.4 |
|---|---|---|---|
| 2003/0157115 A1 | 8/2003 | Bay et al. | |
| 2003/0229017 A1 | 12/2003 | Wu et al. | |
| 2004/0077826 A1 | 4/2004 | Koganty et al. | |
| 2012/0021430 A1* | 1/2012 | Bovin | C07F 9/106 435/7.1 |
| 2012/0184461 A1 | 7/2012 | Bovin | 506/13 |
| 2014/0161723 A1 | 6/2014 | Bovin | 424/1.69 |
| 2015/0064690 A1 | 3/2015 | Bovin | 435/5 |

FOREIGN PATENT DOCUMENTS

| WO | WO 2005/090368 A1 | 9/2005 |
|---|---|---|
| WO | WO 2015/170121 A1 | 11/2015 |

OTHER PUBLICATIONS

Macher et al., "The Galα1,3Galβ1,4GlcNAc-R (α-Gal) epitope: a carbohydrate of unique evolution and clinical relevance," Biochim. Biophys. Acta, 2008, vol. 1780, No. 2, pp. 75-88; Published online Nov. 22, 2007.*

Blake et al., "FSL Constructs: A Simple Method for Modifying Cell/Virion Surfaces with a Range of Biological Markers Without Affecting their Viability," J. Vis. Exp., 2011, vol. 54, e3289; Published online Aug. 5, 2011.*

Frame et al; "Synthetic glycolipid modification of red blood cell membranes"; *Transfusion*, 47(5), pp. 876-882 (2007).

Co-pending U.S. Appl. No. 12/998,345, filed Apr. 12, 2011; Specification (371 of PCT/EA2008/000006, filed Oct. 13, 2008); now U.S. Pat. No. 8,674,061.

Nishimura, Shin-Ichiro, et al; "Specific crosslinking of cell adhesive molecules by heterobifunctional glycopeptide synthesised on the basis of chemoenzymatic strategy"; *Chemical communication*; vol. 15; pp. 1435-1436 (1999).

Shaikh, Harun, A., et al; Synthesis of glycocluster peptides; *Carbohydrate research*, vol. 343; pp. 1665-1674 (2008).

* cited by examiner

*Primary Examiner* — Galina M. Yakovleva

(74) *Attorney, Agent, or Firm* — Nixon & Vanderhye P.C.

(57) ABSTRACT

The invention relates to functional lipid constructs and their use in diagnostic and therapeutic applications, including serodiagnosis, where the functional moiety is carbohydrate, peptide, chemically reactive group, conjugator or fluorophore.

5 Claims, 13 Drawing Sheets

Specification includes a Sequence Listing.

SEQUENCE LISTING

```
<160> NUMBER OF SEQ ID NOS: 55

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Ser Lys Lys Lys Lys Gly
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic peptide

<400> SEQUENCE: 2

Ala Ala Ala Ala Ala
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic peptide

<400> SEQUENCE: 3

Gly Ser Gly Ser Gly
1               5

<210> SEQ ID NO 4
<211> LENGTH: 7
<212> TYPE: PRT
```

```
<213> ORGANISM: Artificial sequence
<220> FEATURE:
<223> OTHER INFORMATION: Synthetic peptide

<400> SEQUENCE: 4

Gly Lys Lys Lys Lys Ser Cys
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5

Ala Ala Ala Ala Ala Cys
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

Gly Ser Gly Ser Gly Cys
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Cys Ser Lys Lys Lys Lys Gly
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Cys Ala Ala Ala Ala Ala
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Cys Gly Ser Gly Ser Gly
1               5

<210> SEQ ID NO 10
<211> LENGTH: 17
<212> TYPE: PRT
<213> ORGANISM: Artificial sequence
```

```
<220> FEATURE:
<223> OTHER INFORMATION: Synthetic peptide

<400> SEQUENCE: 10

Gln Thr Asn Asp Lys His Lys Arg Asp Thr Tyr Ala Ala Ala Ala
1               5                   10                  15

Cys

<210> SEQ ID NO 11
<211> LENGTH: 17
<212> TYPE: PRT
<213> ORGANISM: Artificial sequence
<220> FEATURE:
<223> OTHER INFORMATION: Synthetic peptide

<400> SEQUENCE: 11

Gln Thr Asn Asp Lys His Lys Arg Asp Thr Tyr Gly Ser Gly Ser Gly
1               5                   10                  15

Cys

<210> SEQ ID NO 12
<211> LENGTH: 17
<212> TYPE: PRT
<213> ORGANISM: Artificial sequence
<220> FEATURE:
<223> OTHER INFORMATION: Synthetic peptide

<400> SEQUENCE: 12

Gln Thr Asn Asp Met His Lys Arg Asp Thr Tyr Gly Ser Gly Ser Gly
1               5                   10                  15

Cys

<210> SEQ ID NO 13
<211> LENGTH: 14
<212> TYPE: PRT
<213> ORGANISM: Artificial sequence
<220> FEATURE:
<223> OTHER INFORMATION: Synthetic peptide

<400> SEQUENCE: 13

Ser Ser Gln Thr Asn Asp Lys His Lys Arg Asp Thr Tyr Cys
1               5                   10

<210> SEQ ID NO 14
<211> LENGTH: 11
<212> TYPE: PRT
<213> ORGANISM: Artificial sequence
<220> FEATURE:
<223> OTHER INFORMATION: Synthetic peptide

<400> SEQUENCE: 14

Thr Tyr Pro Ala His Thr Ala Asn Glu Val Cys
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Thr Tyr Pro Ala His Thr Ala Asn Glu Cys
1               5                   10
```

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Pro Ala His Thr Ala Asn Glu Val Cys
1               5

<210> SEQ ID NO 17
<211> LENGTH: 11
<212> TYPE: PRT
<213> ORGANISM: Artificial sequence
<220> FEATURE:
<223> OTHER INFORMATION: Synthetic peptide

<400> SEQUENCE: 17

Ser Gln Thr Asn Asp Lys His Lys Arg Asp Cys
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic peptide

<400> SEQUENCE: 18

Cys Thr Tyr Pro Ala His Thr Ala Asn Glu
1               5                   10

<210> SEQ ID NO 19
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 19

Cys Xaa Xaa Xaa Xaa Xaa Xaa Trp Thr Pro Pro Arg Ala Gln Ile Thr
1               5                   10                  15

Gly Tyr Leu Thr Val Gly Leu Thr Arg Arg
            20                  25

<210> SEQ ID NO 20
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 20

Cys Xaa Xaa Xaa Xaa Xaa Xaa Trp Thr Pro Pro Arg Ala Gln Ile Thr
1               5                   10                  15

```
Gly Tyr Arg Leu Thr Val Gly Leu Thr Arg Arg
            20                  25

<210> SEQ ID NO 21
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 21

Cys Xaa Xaa Xaa Xaa Xaa Xaa Val Met Tyr Ala Ser Ser Gly
1               5                   10

<210> SEQ ID NO 22
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 22

Cys Xaa Xaa Xaa Xaa Xaa Xaa Tyr Pro Ala His Thr Ala Asn Glu
1               5                   10                  15

<210> SEQ ID NO 23
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(13)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 23

Val Met Tyr Ala Ser Ser Gly Xaa Xaa Xaa Xaa Xaa Xaa Cys
1               5                   10

<210> SEQ ID NO 24
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 24

Asp Tyr His Arg Val Met Tyr Ala Ser Ser Gly Xaa Xaa Xaa Xaa Xaa
1               5                   10                  15
```

Xaa Cys

<210> SEQ ID NO 25
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 25

Thr Asn Gly Glu Thr Gly Gln Leu Val His Arg Phe Xaa Xaa Xaa Xaa
1               5                   10                  15

Xaa Xaa Cys

<210> SEQ ID NO 26
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 26

Thr Asn Gly Glu Met Gly Gln Leu Val His Arg Phe Xaa Xaa Xaa Xaa
1               5                   10                  15

Xaa Xaa Cys

<210> SEQ ID NO 27
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 27

Asp Thr Tyr Pro Ala His Thr Ala Asn Glu Val Ser Glu Xaa Xaa Xaa
1               5                   10                  15

Xaa Xaa Xaa Cys
            20

<210> SEQ ID NO 28
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where Xaa may be any naturally occurring amino acid)

<400> SEQUENCE: 28

Thr Tyr Pro Ala His Thr Ala Asn Glu Val Xaa Xaa Xaa Xaa Xaa Xaa
1               5                   10                  15

Cys

<210> SEQ ID NO 29
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 29

Pro Ala His Thr Ala Asn Glu Val Xaa Xaa Xaa Xaa Xaa Xaa Cys
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 30

Tyr Pro Ala His Thr Ala Asn Glu Xaa Xaa Xaa Xaa Xaa Xaa Cys
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 31

Thr Tyr Pro Ala His Thr Ala Asn Xaa Xaa Xaa Xaa Xaa Xaa Cys
1               5                   10                  15

<210> SEQ ID NO 32
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 32

Thr Tyr Pro Ala His Thr Ala Asn Glu Xaa Xaa Xaa Xaa Xaa Xaa Cys
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 33

Tyr Pro Ala His Thr Ala Asn Glu Val Xaa Xaa Xaa Xaa Xaa Xaa Cys
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 34

Tyr Pro Ala His Thr Ala Asn Glu Xaa Xaa Xaa Xaa Xaa Xaa Cys
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 35

Pro Ala His Thr Ala Asn Glu Val Ser Xaa Xaa Xaa Xaa Xaa Xaa Cys
1               5                   10                  15

<210> SEQ ID NO 36
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 36

-continued

```
Asp Thr Tyr Pro Ala His Thr Ala Asn Glu Xaa Xaa Xaa Xaa Xaa Xaa
1               5                   10                  15

Cys

<210> SEQ ID NO 37
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 37

Tyr Pro Ala His Thr Ala Asn Glu Val Ser Xaa Xaa Xaa Xaa Xaa Xaa
1               5                   10                  15

Cys

<210> SEQ ID NO 38
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 38

Ser Gln Thr Asn Asp Lys His Lys Arg Asp Xaa Xaa Xaa Xaa Xaa Xaa
1               5                   10                  15

Cys

<210> SEQ ID NO 39
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 39

Gln Thr Asn Asp Lys His Lys Arg Asp Thr Tyr Xaa Xaa Xaa Xaa Xaa
1               5                   10                  15

Xaa Cys

<210> SEQ ID NO 40
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (25)..(30)
<223> OTHER INFORMATION: Optional proximal terminal sequence (PTS) of 0
``` to 6 residues selected to promote solubility of the peptide (where
Xaa may be any naturally occurring amino acid)

<400> SEQUENCE: 40

Gln Thr Asn Asp Lys His Lys Arg Asp Thr Tyr Ser Ser Gln Thr Asn
1               5                   10                  15

Asp Met His Lys Arg Asp Thr Tyr Xaa Xaa Xaa Xaa Xaa Xaa Cys
            20                  25                  30

<210> SEQ ID NO 41
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 41

Gln Thr Asn Asp Met His Lys Arg Asp Thr Tyr Xaa Xaa Xaa Xaa Xaa
1               5                   10                  15

Xaa Cys

<210> SEQ ID NO 42
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 42

Ser Ser Gln Thr Asn Asp Lys His Lys Arg Xaa Xaa Xaa Xaa Xaa Xaa
1               5                   10                  15

Cys

<210> SEQ ID NO 43
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 43

Ser Ser Gln Thr Asn Asp Lys His Lys Arg Asp Thr Tyr Xaa Xaa Xaa
1               5                   10                  15

Xaa Xaa Xaa Cys
            20

<210> SEQ ID NO 44
<211> LENGTH: 20
<212> TYPE: PRT

```
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 44

Ser Ser Gln Thr Asn Asp Met His Lys Arg Asp Thr Tyr Xaa Xaa Xaa
1               5                   10                  15

Xaa Xaa Xaa Cys
            20

<210> SEQ ID NO 45
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (27)..(32)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 45

Ser Ser Gln Thr Asn Asp Lys His Lys Arg Asp Thr Tyr Ser Ser Gln
1               5                   10                  15

Thr Asn Asp Met His Lys Arg Asp Thr Tyr Xaa Xaa Xaa Xaa Xaa Xaa
            20                  25                  30

Cys

<210> SEQ ID NO 46
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 46

Gln Thr Asn Asp Lys His Lys Arg Asp Thr Xaa Xaa Xaa Xaa Xaa Xaa
1               5                   10                  15

Cys

<210> SEQ ID NO 47
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 47
```

Ser Gln Thr Asn Asp Lys His Lys Arg Asp Thr Xaa Xaa Xaa Xaa Xaa
1               5                   10                  15

Xaa Cys

<210> SEQ ID NO 48
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 48

Thr Asn Asp Lys His Lys Arg Asp Thr Tyr Pro Xaa Xaa Xaa Xaa Xaa
1               5                   10                  15

Xaa Cys

<210> SEQ ID NO 49
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 49

Glu Glu Thr Gly Glu Thr Gly Gln Leu Val Xaa Xaa Xaa Xaa Xaa Xaa
1               5                   10                  15

Cys

<210> SEQ ID NO 50
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 50

Glu Glu Glu Thr Gly Glu Thr Gly Gln Leu Xaa Xaa Xaa Xaa Xaa Xaa
1               5                   10                  15

Cys

<210> SEQ ID NO 51
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0

-continued to 6 residues selected to promote solubility of the peptide (where
Xaa may be any naturally occurring amino acid)

<400> SEQUENCE: 51

Glu Thr Gly Glu Thr Gly Gln Leu Val His Xaa Xaa Xaa Xaa Xaa Xaa
1               5                   10                  15

Cys

<210> SEQ ID NO 52
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 52

Ser Pro Pro Arg Arg Ala Arg Val Thr Xaa Xaa Xaa Xaa Xaa Xaa Cys
1               5                   10                  15

<210> SEQ ID NO 53
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (17)..(22)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 53

Tyr Arg Tyr Arg Tyr Thr Pro Lys Glu Lys Thr Gly Pro Met Lys Glu
1               5                   10                  15

Xaa Xaa Xaa Xaa Xaa Xaa Cys
            20

<210> SEQ ID NO 54
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 54

Trp Gln Pro Pro Arg Ala Arg Ile Xaa Xaa Xaa Xaa Xaa Xaa Cys
1               5                   10                  15

<210> SEQ ID NO 55
<211> LENGTH: 17
<212> TYPE: PRT
<213> ORGANISM: Artificial sequence
<220> FEATURE:
<223> OTHER INFORMATION: Synthetic peptide

```
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide (where
      Xaa may be any naturally occurring amino acid)

<400> SEQUENCE: 55

Thr Ile Thr Gly Leu Glu Pro Gly Thr Glu Xaa Xaa Xaa Xaa Xaa Xaa
1               5                   10                  15
Cys
```

FUNCTIONAL LIPID CONSTRUCTS

This application is a continuation-in-part of application Ser. No. 14/172,346 filed Feb. 4, 2014 (U.S. Pat. No. 9,802,981), which is a continuation of application Ser. No. 12/734,072 filed May 18, 2011 (U.S. Pat. No. 8,669,084) which is a 371 of PCT/NZ2008/000266 filed Oct. 13, 2008, which claims priority to New Zealand Patent Application Nos. 562475 filed Oct. 12, 2007, 569024 filed Jun. 6, 2008, 569059 filed Jun. 10, 2008, 569912 filed Jul. 7, 2008, 569964 filed Jul. 18, 2008, and which claims benefit of Australian Provisional Application No. 2015904655 filed Nov. 11, 2015, the entire contents of each of which are hereby incorporated by reference.

TECHNICAL FIELD

The invention relates to methods for effecting qualitative and quantitative changes in the functional moieties expressed at the surface of cells and multi-cellular structures, and functional lipid constructs for use in such methods. In particular, the invention relates to functional lipid constructs and their use in diagnostic and therapeutic applications, including serodiagnosis, where the functional moiety is a carbohydrate, peptide, chemically reactive group, conjugator or fluorophore.

BACKGROUND ART

The ability to effect qualitative and quantitative changes in the functional moieties expressed at the surface of liposomes, cells and multi-cellular structures provides for a range of diagnostic and therapeutic applications. A functional moiety may be a carbohydrate, peptide, chemically reactive group (e.g. maleimide), conjugator (e.g. biotin) or fluorophore (e.g. fluorescein).

The specification accompanying international application number PCT/NZ2005/000052 (publication number WO 2005/090368) describes the preparation of carbohydrate-lipid constructs for use in methods of effecting qualitative and quantitative changes in the level of carbohydrates expressed at the surface of cells and multi-cellular structures. The use of the constructs to prepare quality control cells for use in blood grouping and diagnostics is described.

The specification accompanying international application number PCT/NZ2006/000245 (publication number WO 2007/035116) describes another method for the preparation of carbohydrate-lipid constructs where the carbohydrate is the polymer hyaluronic acid. The use of the constructs to modify embryos to promote association with endometrial cells is described.

The specification accompanying international application number PCT/NZ2007/000256 (publication number WO 2008/030115) describes the preparation of fluorophore-lipid constructs. The use of the constructs in methods of fluorescently labeling cells is described.

Known methods of effecting changes in the peptides expressed at the surface of cells include gene manipulation, chemical modification of membrane peptides, and "cell surface painting" using lipid anchors such as GPI (Legler et al (2004), McHugh et al (1995), Medof et al (1996), Metzner et al (2008), Morandat et al (2002), Premkumar et al (2001), Ronzon et al (2004), Skountzou et al (2007)).

In addition to these methods of effecting changes of endogenously expressed peptides, exogenously prepared peptides may be coupled to lipids of the membrane utilising biotin-avidin conjugation. Biotin binds to the tetrameric protein avidin with a dissociation constant ($K_D$) of the order $10^{-15}$ mol/L. This strong binding is exploited in a number of laboratory applications.

In these laboratory applications biotin is linked to a molecule such as a carbohydrate or a peptide. The preferential binding of avidins to biotin is exploited in a number of isolation or separation applications in addition to the coupling of peptides to the lipids of membranes.

The specification accompanying international application no. PCT/NZ02/00214 (publication no. WO 03/039074) describes a "two-step method" of localizing an antigen such as a peptide to the surface of cells. In the method the biotinylated glycoside (BioG) is contacted with a suspension of cells for a time and at a temperature sufficient to allow the BioG molecules to incorporate via their diacyl lipid tails into the cell membrane of the cells.

An exogenously prepared avidinylated peptide may then be localized to the surface of the BioG modified cells by contacting the peptide with the modified cells. Alternatively, an exogenously prepared biotinylated peptide may be localized to the surface of the modified cells via a biotin-avidin bridge.

In either alternative of the "two-step method" the amount of peptide localized to the surface of the cells may be controlled by controlling the concentration, time and temperature at which the BioG molecules are contacted with the suspension of cells to provide the modified cells. However, the utility of the method is limited by the availability and dispersibility of BioG in biocompatible media such a saline.

The specification accompanying international application no. PCT/NZ2005/000052 (publication no. WO 2005/090368) describes a "one-step method" of localizing carbohydrate antigen to the surface of cells. The "one-step method" utilizes carbohydrate-lipid constructs that are dispersible in biocompatible media and can therefore be used to prepare modified cells without loss of vitality. However, a method of preparing peptide-lipid constructs with comparable dispersibility in biocompatible media and of general applicability to peptides has not been described.

Relatively little work has been performed on the coupling of peptides to phospholipids as individual components prior to their incorporation in self assembling lipid structures, such as liposomes. However, a variety of standard techniques have been described for the covalent coupling of peptides to liposome surfaces.

Martin et al (1990) has reviewed methods of attaching moieties including peptides, to the surface of liposomes.

Blume et al (1993) describes the coupling of the water soluble Glu-plasminogen to liposomes by the method described by Kung and Redemann (1986). The chemical ECDI (1-ethyl-(3-dimethylaminopropyl) carbodiimide hydrochloride) is used to activate the liposomes prior to incubation of the activated liposome suspension with Glu-plasminogen. Proteo-PEG-coated liposomes with Glu-plasminogen covalently attached to the ends of the distearyly-phosphatidylethanolamine (DSPE)-PEG-COOH are provided.

Haselgrübler et al (1995) describes a heterobifunctional crosslinker used to facilitate the preparation of immunoliposomes. The crosslinker is synthesised from a diamine derivative of poly(ethylene glycol) (PEG, average molecular weight 800 dalton (18 mer)). The crosslinker has 2-(pyridylthio)propronyl (PDP) and N-hydroxysuccinimide ester (NHS) as functional groups.

Ishida et al (2001) describes the preparation of liposomes bearing polyethylene glycol-coupled trasnferrin. Transferrin was conjugated via the terminal carboxyl residue of DSPE-PEG-COOH. The liposomes were proposed as having utility in in vivo cytoplasmic targeting of chemotherapeutic agents or plasmid DNAs to target cells.

Massaguer et al (2001) describes the incorporation of a peptide sequence (GGRGRS) and hydrophobic derivatives to the surface of chemically activated liposomes. The incorporation was carried out through the carboxyl group of N-glutaryl dipalmitoyl phosphatidyl choline (NGPE).

Massaguer et al (2001) noted that considering potential in vivo applications, where sterility and simplicity would be some of the most important requirements, processes based on chemical reactions on the surface of liposomes involving extra steps would be more difficult to be scaled up at the industrial level. A hydrophobic derivative of the peptide sequence was identified as providing optimal properties for incorporation to the surface of liposomes.

Chung et al (2004) describe the antigenic determinant shielding effect of DOPE-PEG incorporated into the membranes of cells and speculated concerning the potential of lipid-PEG(n)(s) to regulate biological cell responses and the extension of this concept to the introduction of functional molecules at the end of the PEG chain.

Kato et al (2004) describe a method for anchoring of macromolecular proteins into the membranes of living mammalian cells. A dioleylphosphatidylethanolamine (DOPE) derivative coupled with hydrophilic poly(ethylene glycol) (PEG80) was used as the synthetic membrane anchor. Peptides were conjugated at the distal terminal of the PEG moiety via an amino-reactive N-hydroxysuccinimide derivative of the synthetic membrane anchor.

The PEG80 moiety facilitated solublisation of the synthetic membrane anchor in water. As noted by Kato et al (2004) if the anchor is insoluble in water, undesirable and complicated processes such as liposome preparation and the fusion of liposomes with the cell membrane may be required to anchor the conjugates into the cell membrane.

An additional advantage noted by Kato et al (2004) was that synthetic membrane anchors with high hydrophile-lipophile balance values (attributable to PEG spacer with a high number of oxyethylene units) were concluded to have no cytolytic activity. However, difficulties arise in the use of synthetic membrane anchors including a PEG spacer with a high number of oxyethylene units.

Firstly, the expression of the conjugative peptide or other endogenous cell surface peptides may be masked by the PEG spacer. Secondly, a PEG spacer with a high number of oxyethylene units may elicit non-specific adherence of protein (including antibodies in certain individuals) and/or the non-specific activation of the complement cascade.

Winger et al (1996) describes the conjugation of bromoacetylated DSPE with a thiol terminated decapeptide comprising at its C-terminus the minimal human thrombin-receptor peptide agonist (HS-SerPheLeuLeuArgAsn).

Hashimoto et al (1986) describes the conjugation of iodoacetylated DSPE with thiolated compounds.

A need exists for a general method of preparing peptide-lipid constructs that may be incorporated as individual components in self assembling lipid structures, such as liposomes, by a "one-step method". The method should desirably provide peptide-lipid constructs that are readily dispersible in biocompatible media and spontaneously incorporate in to the membranes of cells and multi-cellular structures.

Peptide-lipid constructs with these characteristics are anticipated to have utility in a range of therapeutic and diagnostic applications, especially serodiagnosis, in addition to the preparation of functionalized liposomes.

It is an object of this invention to provide functional-lipid constructs that are dispersible in biocompatible media and spontaneously incorporate into the membranes of cells and multi-cellular structures.

It is an object of this invention to provide functional-lipid constructs for use in the preparation of peptide-lipid constructs that are dispersible in biocompatible media and spontaneously incorporate into the membranes of cells and multi-cellular structures.

It is an object of this invention to provide peptide-lipid constructs that are dispersible in biocompatible media and spontaneously incorporate into the membranes of cells and multi-cellular structures.

These objects are to be read disjunctively with the object to at least provide the public with a useful choice.

DISCLOSURE OF INVENTION

In a first aspect the invention provides a functional lipid construct of the structure F-S-L where F is a functional moiety, L is a diacyl or a dialkyl lipid, and S is a spacer covalently linking F to L including the substructure:

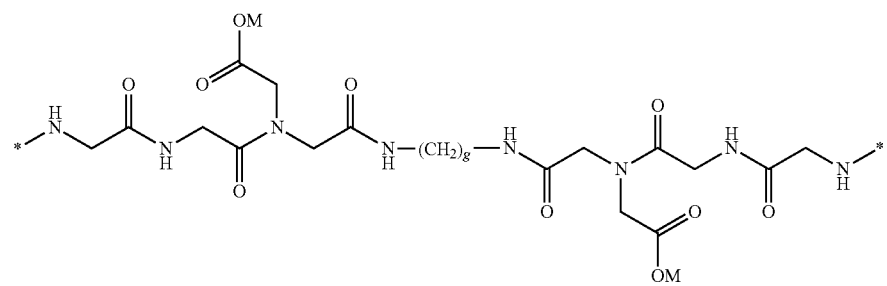

where g is the integer 1, 2 or 3, M is a monovalent cation or substituent, and * is other than H.

Preferably, the substructure is:

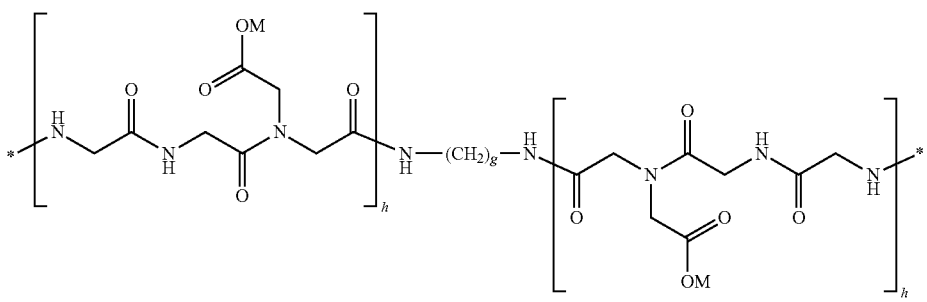

where h is the integer 1, 2, 3 or 4.

Preferably, g is the integer 2 and h is the integer 1, 2 or 4.

Preferably, M is H or $CH_3$.

Preferably, L is a diacylglycerophospholipid. More preferably, L is phosphatidylethanolamine.

Preferably, the structure of the functional lipid construct includes the partial structure:

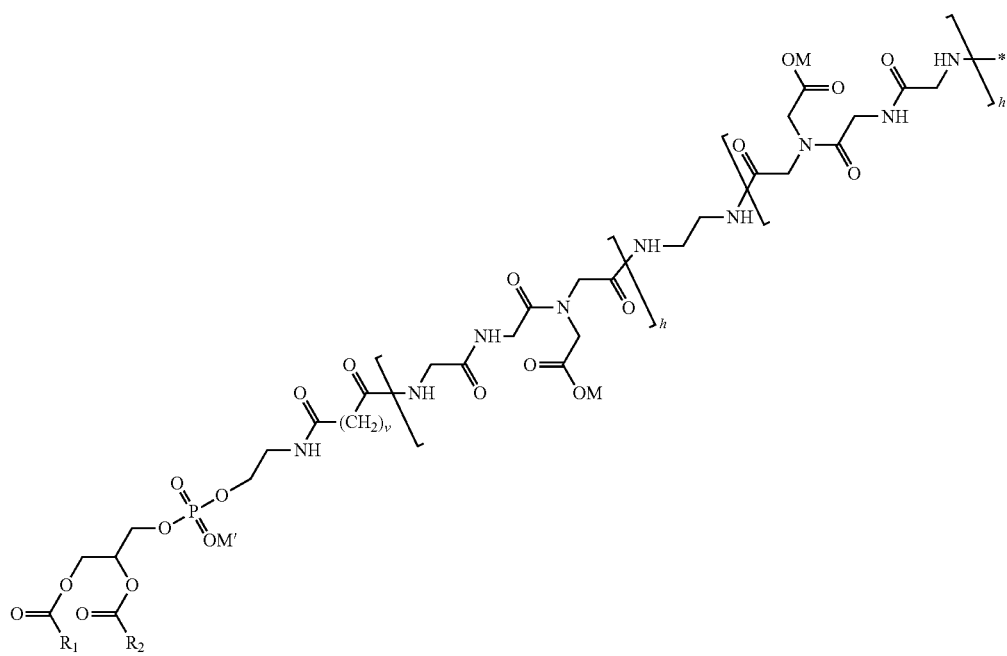

where v is the integer 3, 4 or 5, M' is a monovalent cation, and $R_1$ and $R_2$ are independently selected from the group consisting of: alkyl or alkenyl substituents of the fatty acids trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid.

Preferably, F is a functional moiety selected from the group consisting of: carbohydrate (glycan), peptide, chemically reactive group, conjugator or fluorophore.

In a first alternative of the first aspect the invention provides a functional lipid construct of the structure:

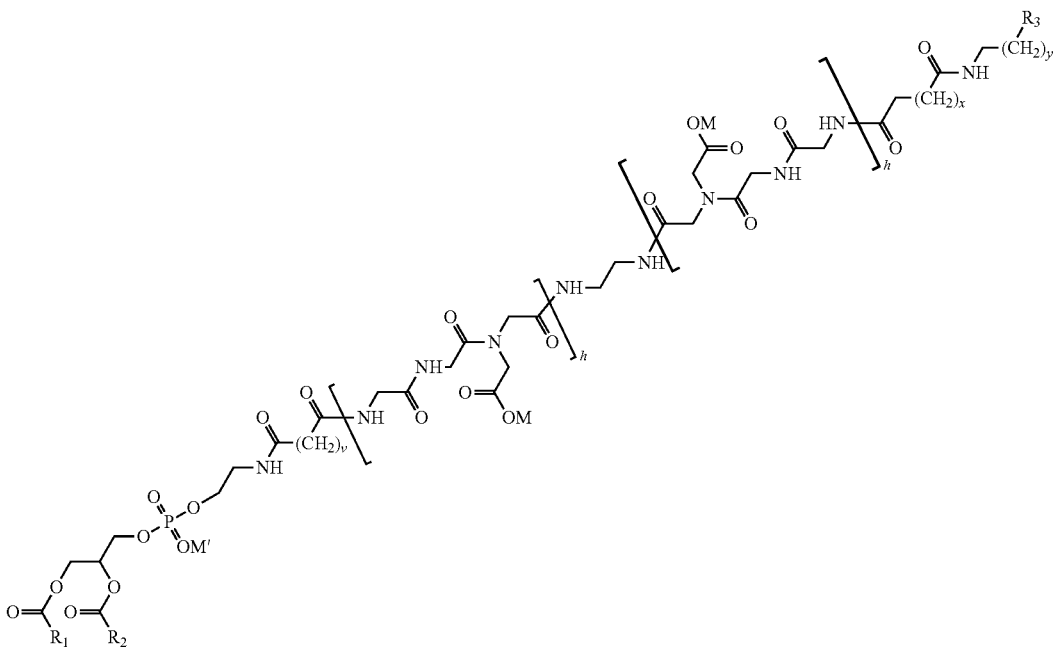

where F is a carbohydrate, x is the integer 2, 3 or 4, y is the integer 1, 2 or 3, and $R_3$ is O of a substituted hydroxyl of the carbohydrate.

Preferably, the carbohydrate is a glycan selected from the group consisting of: GalNAcα1-3(Fucα1-2)Galβ–; Galα1-3(Fucα1-2)Galβ–; Xylα1-3Glcβ–; Xylα1-3Xylα1-3Glcβ–; Neu5Acα2-3Galβ1-4(Fucα1-3)GlcNAcβ–; Galβ1-4(Fucα1-3)GlcNAcβ–; Fucα1-2Galβ1-4(Fucα1-3)GlcNAcβ–; Neu5Acα2-3Galβ1-3GalNAcα–; Neu5Acα2-3Galβ1-3(6-HSO$_3$)GalNAcα–; Neu5Acα2-3Galβ1-3GlcNAcβ–; Neu5Acα2-3Galβ1-3(6-HSO$_3$)GlcNAcβ–; Neu5Acα2-3Galβ–; GalNAcα1-3Galβ1-4GlcNAc–; Galα1-3Galβ1-4GlcNAc–; Galα1-4Galβ1-4Glc–; Neu5Acα2-3Galβ1-3(Fucα1-4)GlcNAcβ–; GalNAcα1-3(Fucα1-2)Galβ1-4GlcNAcβ–; Galα1-3(Fucα1-2)Galβ1-4GlcNAcβ–; Fucα1-2Galβ1-4GlcNAcβ–; Galα1-3Galβ1-4GlcNAcβ–; Galα1-4Galβ1-4GlcNAcβ–; Neu5Acα2-3Galβ1-4GlcNAcβ–; Neu5Acα2-3Galβ1-4(6-HSO$_3$)GlcNAcβ–; Neu5Acα2-3Galβ1-3(Fucα1-4)GlcNAcβ; Galβ1-4GlcNAcβ1-3Galβ1-4GlcNAcβ1-3Galβ1-4GlcNAcβ–; Neu5Ac-α-(2-6')-Galβ1-4GlcNAcβ–; and Neu5Gc-α-(2-6')-Galβ1-4GlcNAcβ–.

In a second alternative of the first aspect the invention provides a functional lipid construct of the structure:

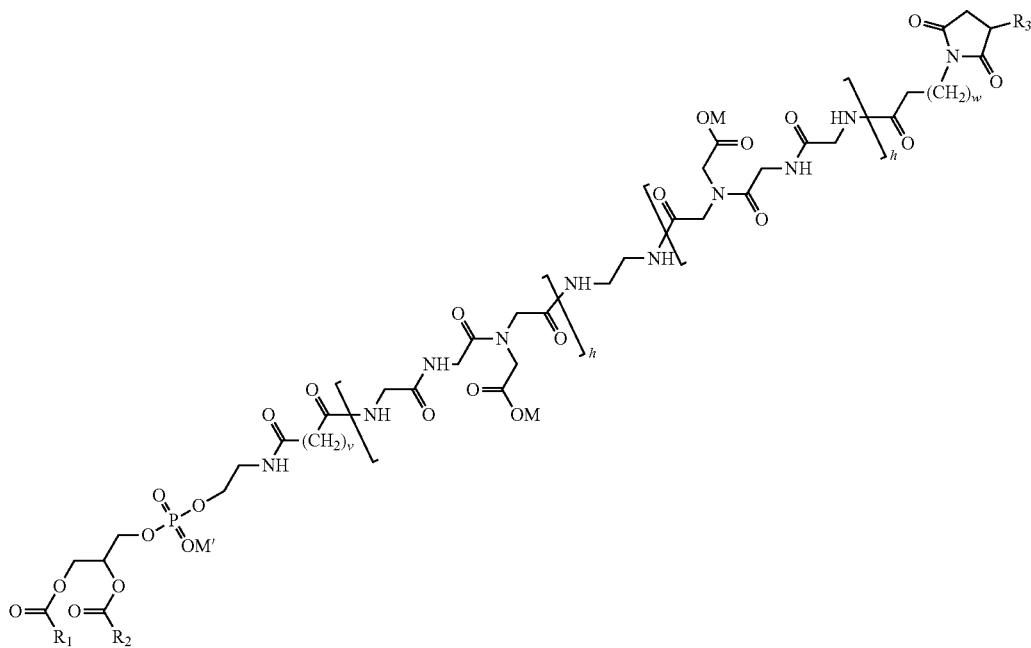

where F is a peptide, w is the integer 1 or 2, and $R_3$ is S of a substituted sulfhydryl of a Cys residue of the peptide.

In a third alternative of the first aspect the invention provides a functional lipid construct of the structure:

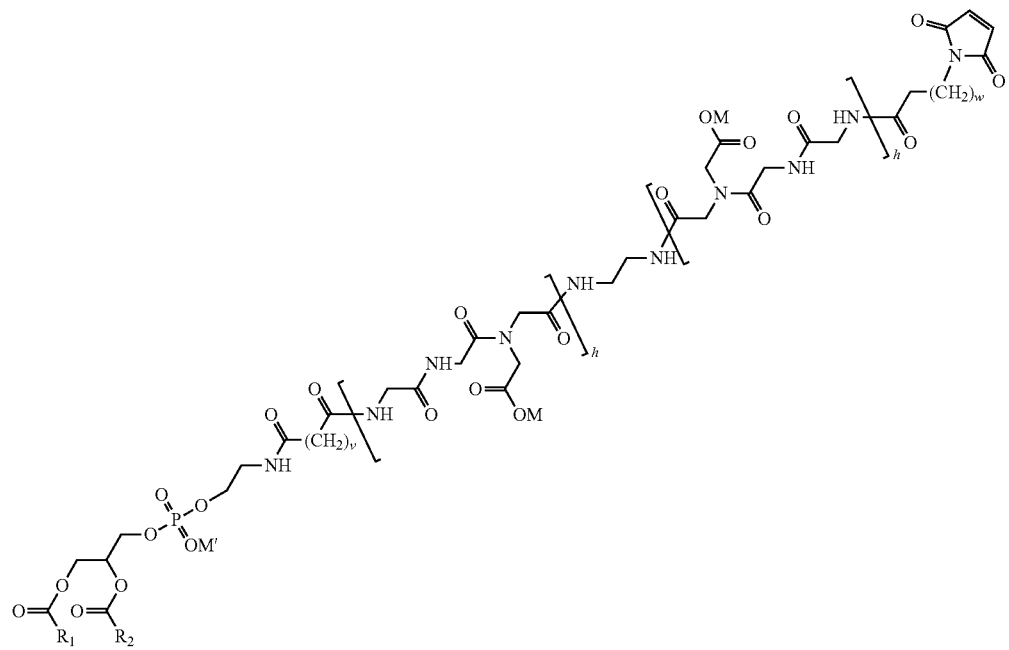

where F is the chemically reactive group maleimide and w is the integer 1 or 2.

In a fourth alternative of the first aspect the invention provides a functional lipid construct of the structure:

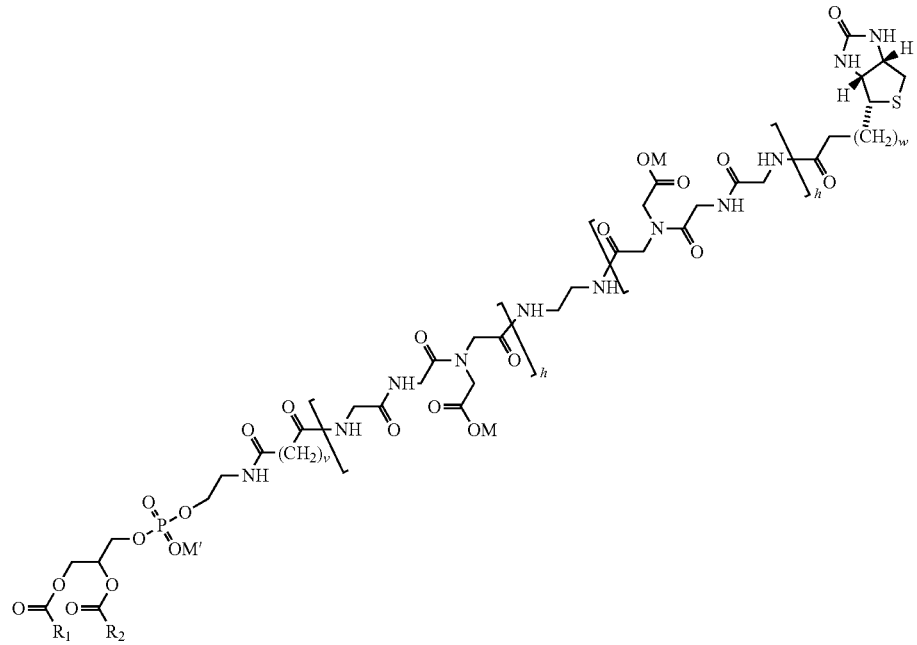

where F is the conjugator biotin and k is the integer 2, 3 or 4.

In a fifth alternative of the first aspect the invention provides a functional lipid construct of the structure:

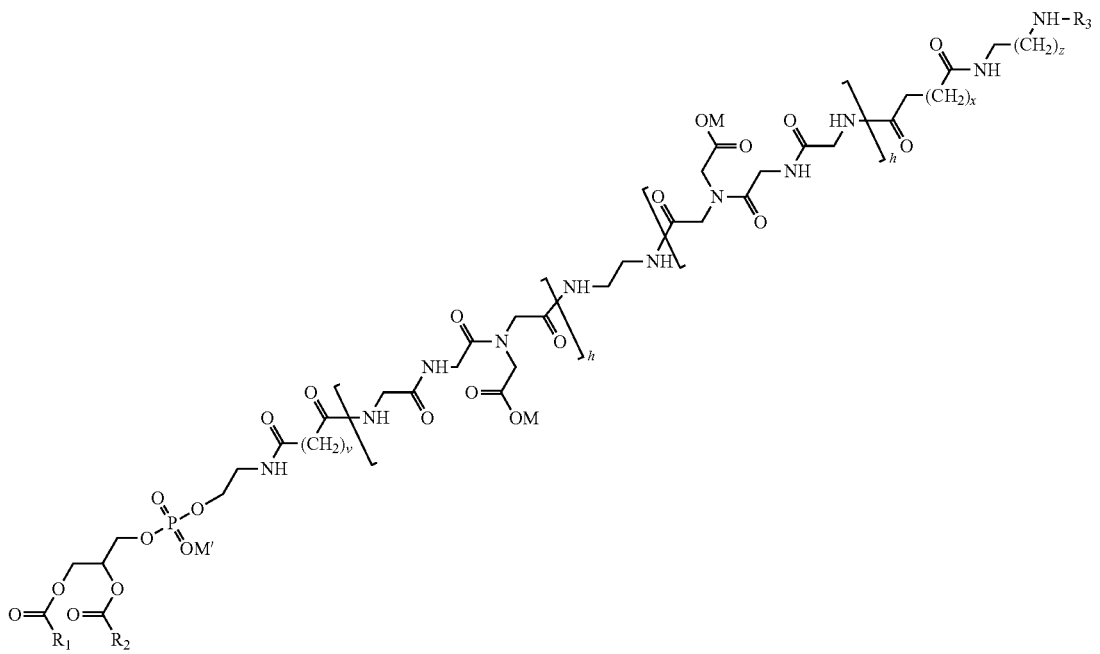
where F is the fluorophore of fluorescein (or one of its derivatives), z is the integer 3, 4 or 5, and $R_3$ is C of the thiocyanate substituent of the isothiocyanate derivative of fluorescein (or one of its derivatives).
Preferably, the substructure is:
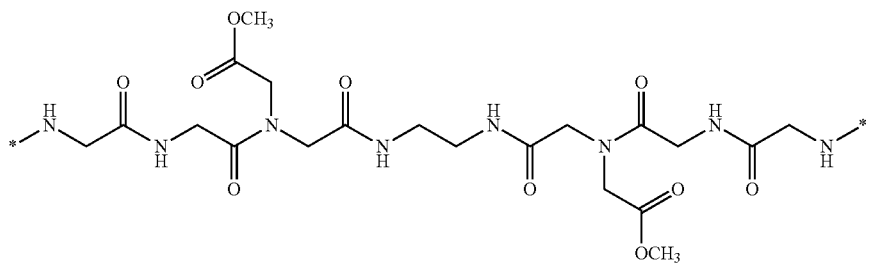 [SMILES: *NCC(=O)NCC(=O)N(CC(=O)NCCNC(=O)CN(CC(=O)OC)C(=O)CNC(=O)CN*)CC(=O)OC]
designated MCMG(1);
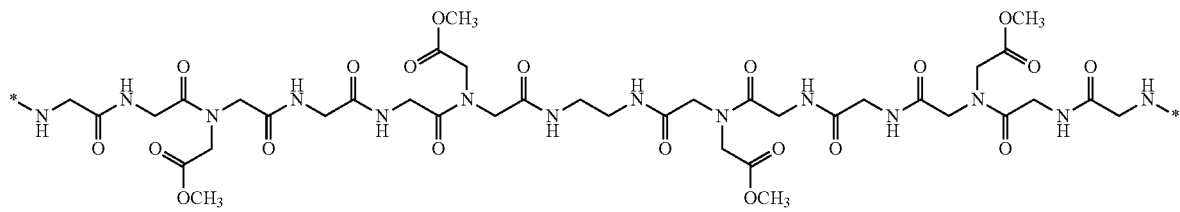 [SMILES: *NCC(=O)NCC(=O)N(CC(=O)NCC(=O)NCC(=O)N(CC(=O)NCCNC(=O)CN(CC(=O)OC)C(=O)CNC(=O)CNC(=O)CN(CC(=O)OC)C(=O)CNC(=O)CN*)CC(=O)OC)CC(=O)OC]
designated MCMG(2);

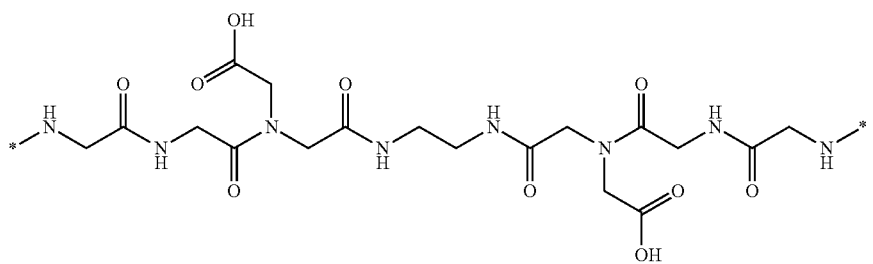 [SMILES: *NCC(=O)NCC(=O)N(CC(=O)O)CC(=O)NCCNC(=O)CN(CC(=O)O)C(=O)CNC(=O)CN*]

designated CMG(1); or

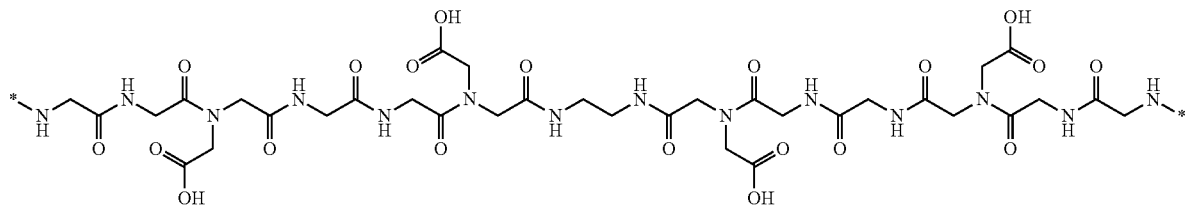 [SMILES: *NCC(=O)NCC(=O)N(CC(=O)O)CC(=O)NCC(=O)NCC(=O)N(CC(=O)O)CC(=O)NCCNC(=O)CN(CC(=O)O)C(=O)CNC(=O)CNC(=O)CN(CC(=O)O)C(=O)CNC(=O)CN*]

designated CMG(2).

In a second aspect the invention provides a water soluble peptide-lipid construct of the structure F-S-L where S is a spacer linked to F via a sulphide bond and includes the substructure:

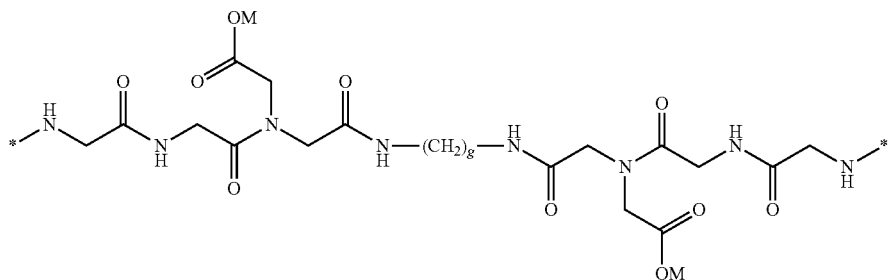

where g is the integer 1, 2 or 3, M is a monovalent cation or substituent, and * is other than H.

Preferably, the substructure is:

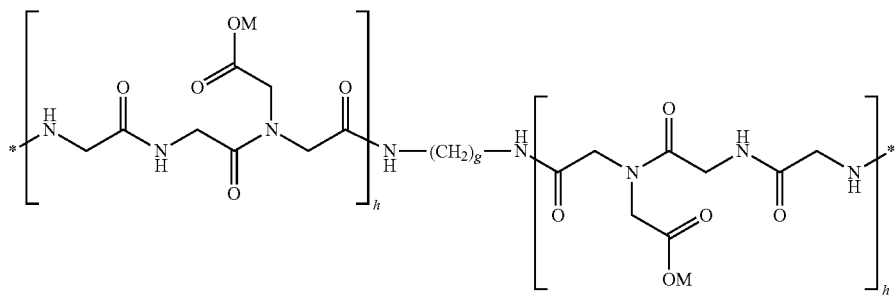

where h is the integer 1, 2, 3 or 4.

Preferably, g and h are the integer 2.

Preferably, M is H or $CH_3$.

Preferably, L is a diacylglycerophospholipid. More preferably, L is phosphatidylethanolamine.

Preferably, the structure of the peptide-lipid construct includes the partial structure:

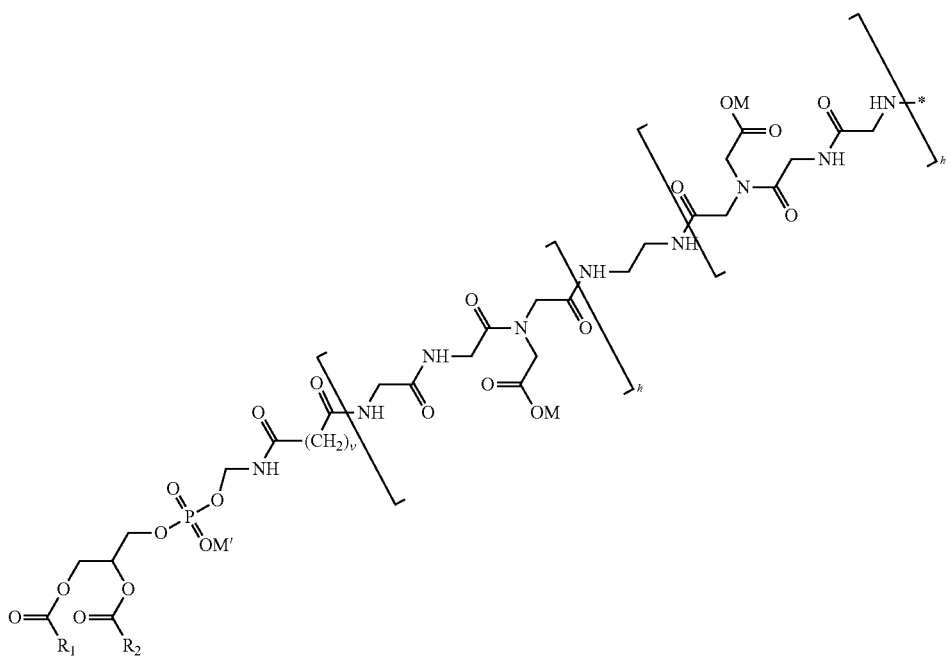

where v is the integer 3, 4 or 5, M' is a monovalent cation, and $R_1$ and $R_2$ are independently selected from the group consisting of: alkyl or alkenyl substituents of the fatty acids trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid.

Preferably, the structure of the peptide-lipid construct includes the partial structure:

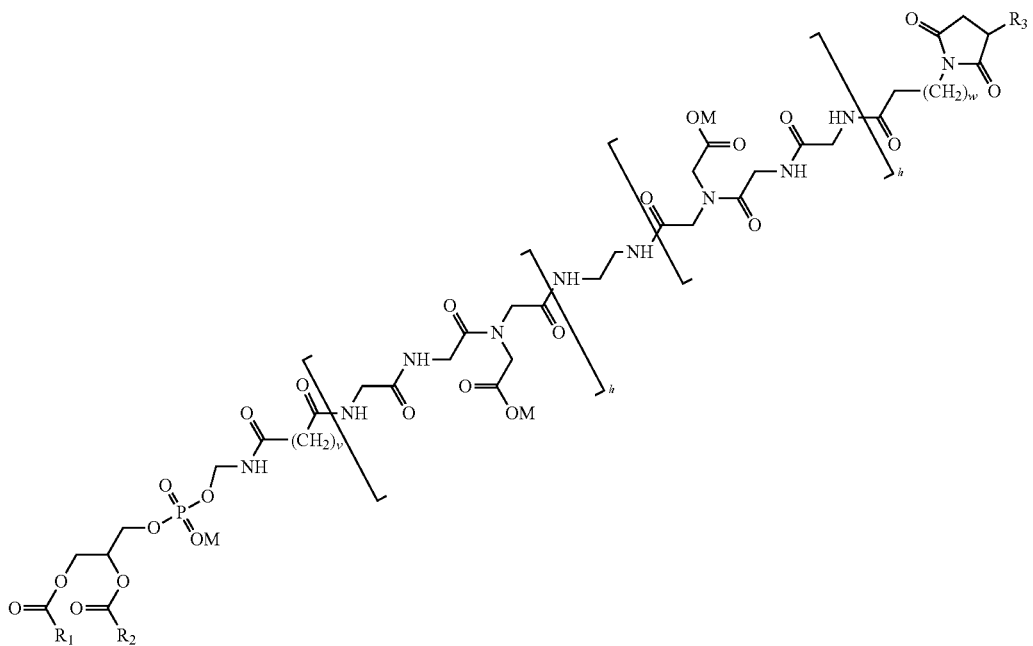

where w is the integer 1 or 2, and $R_3$ is S of a substituted sulfhydryl of a Cys residue of the peptide.

In an embodiment of the second aspect the invention provides a peptide-lipid construct of the structure:

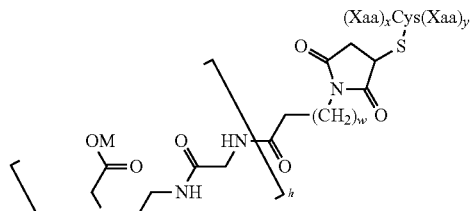
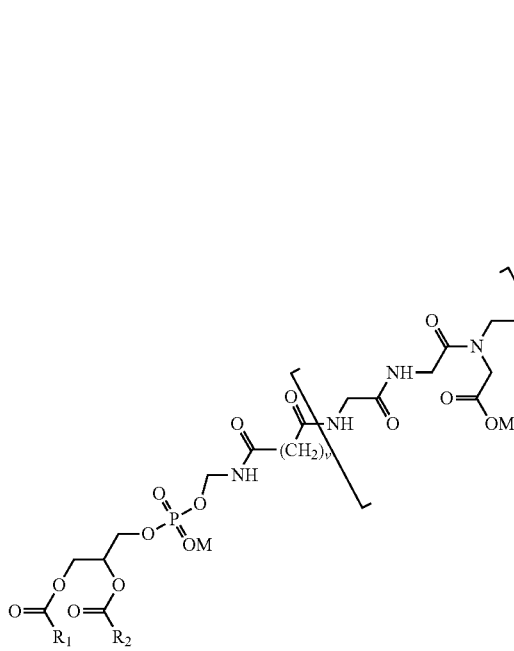

where the sum of x and y is greater than 5. Optionally, F is a peptide including a proximal terminal sequence (PTS) selected to promote solubility of the peptide.

In a preferment of this option, the PTS of the peptide is selected from the group consisting of:

SerLysLysLysLysGly (SEQ ID NO: 01)

AlaAlaAlaAla (SEQ ID NO: 02)

GlySerGlySerGly (SEQ ID NO: 03)

Preferably, the Cys residue is a terminal Cys residue of the peptide (Cys).

Preferably, the terminal sequence of the peptide is selected from the group consisting of:

GlyLysLysLysLysSerCys (SEQ ID NO: 04)

AlaAlaAlaAlaCys (SEQ ID NO: 05)

GlySerGlySerGlyCys (SEQ ID NO: 06)

CysSerLysLysLysLysGly (SEQ ID NO: 07)

CysAlaAlaAlaAla (SEQ ID NO: 08)

CysGlySerGlySerGly (SEQ ID NO: 09)

Preferably, the Cys residue is a terminal Cys residue of the peptide at the carboxy-terminus of the peptide.

Preferably, F is a peptide comprising an epitope of antigens selected from the group consisting of: Glycophorin A, Glycophorin B, or mutations thereof (including the MNS blood group system). More preferably, F is a peptide selected from the List of Peptides. Most preferably, F is a peptide selected from the group consisting of:

GlnThrAsnAspLysHisLysArgAspThrTyrAlaAlaAlaAlaAla Cys (SEQ ID NO: 10)

GlnThrAsnAspLysHisLysArgAspThrTyrGlySerGlySerGly Cys (SEQ ID NO: 11)

GlnThrAsnAspMetHisLysArgAspThrTyrGlySerGlySerGly Cys (SEQ ID NO: 12)

SerSerGlnThrAsnAspLysHisLysArgAspThrTyrCys (SEQ ID NO: 13)

ThrTyrProAlaHisThrAlaAsnGluValCys (SEQ ID NO: 14)

ThrTyrProAlaHisThrAlaAsnGluCys (SEQ ID NO: 15)

ProAlaHisThrAlaAsnGluValCys (SEQ ID NO: 16)

SerGlnThrAsnAspLysHisLysArgAspCys (SEQ ID NO: 17)

CysThrTyrProAlaHisThrAlaAsnGlu (SEQ ID NO: 18)

Preferably, L is a glycerophospholipid selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In an exemplifying first embodiment of the second aspect the invention provides a peptide-lipid construct of the structure:

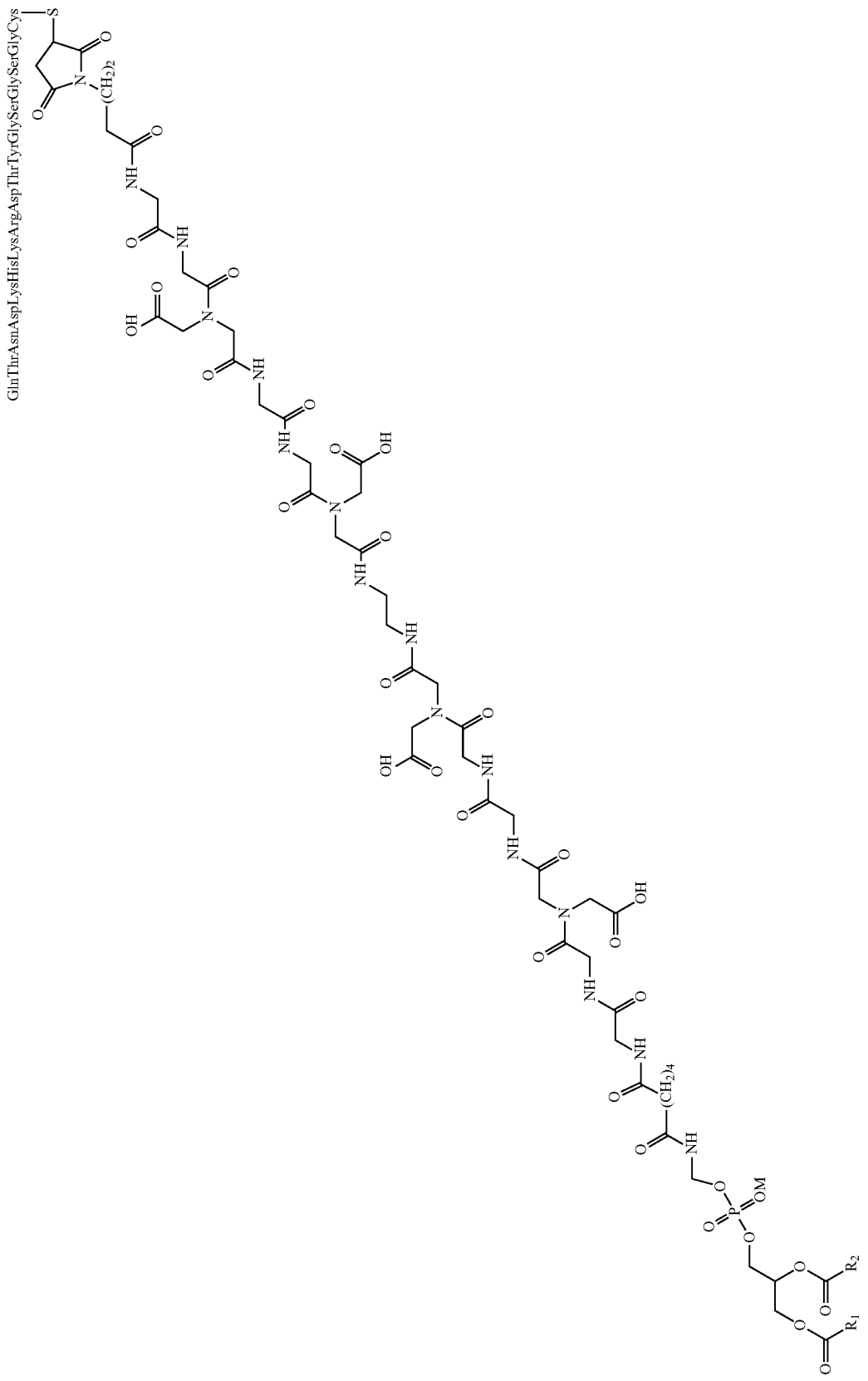

designated DOPE-Ad-CMG(2)-βAla-Mal-PTS-Milt(K) (IX).

In an exemplifying second embodiment of the second aspect the invention provides a peptide-lipid construct of the structure:

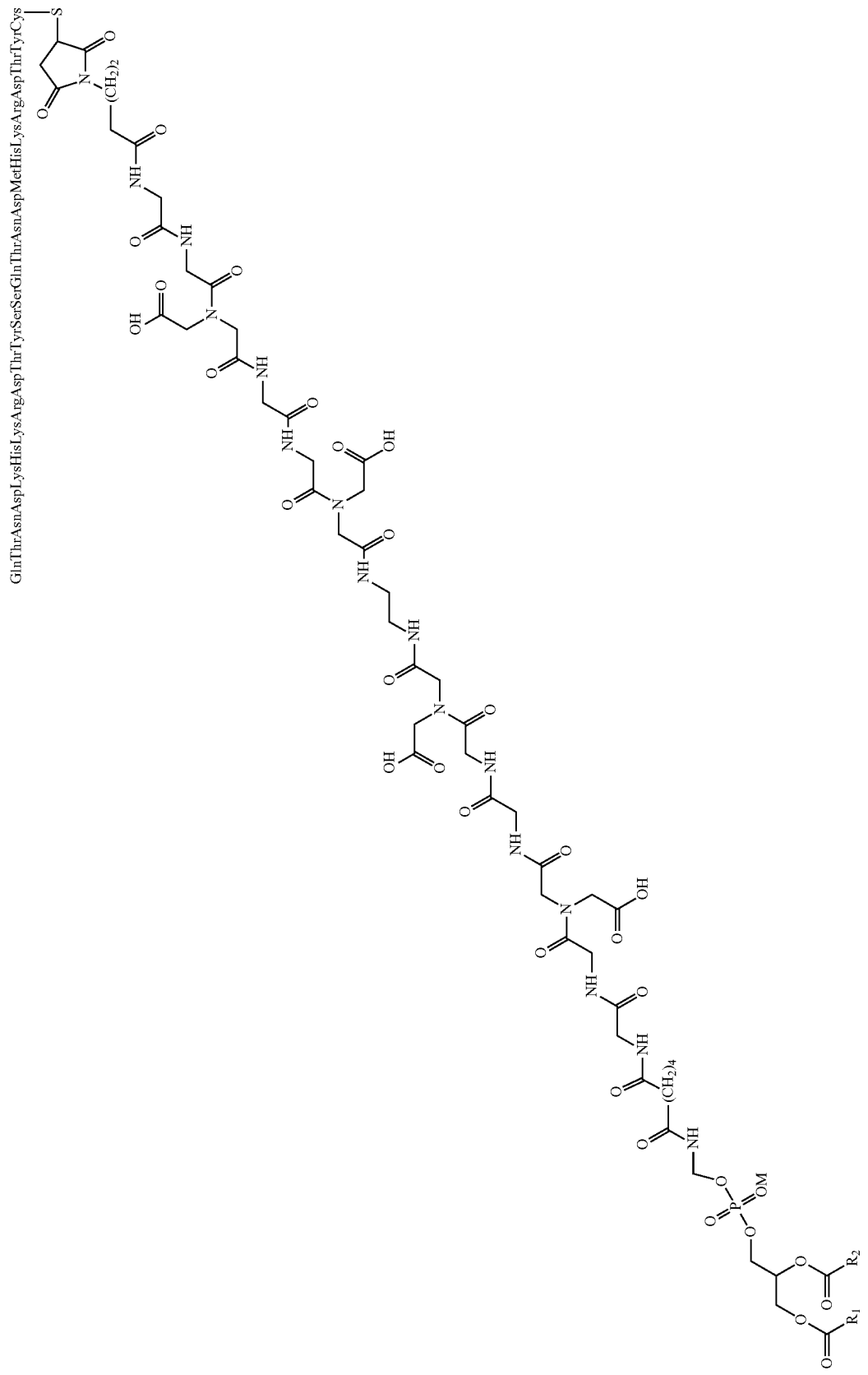

designated DOPE-Ad-CMG(2)-βAla-Mal-Milt(K,M) (X).

In an exemplifying third embodiment of the second aspect the invention provides a peptide-lipid construct of the structure:

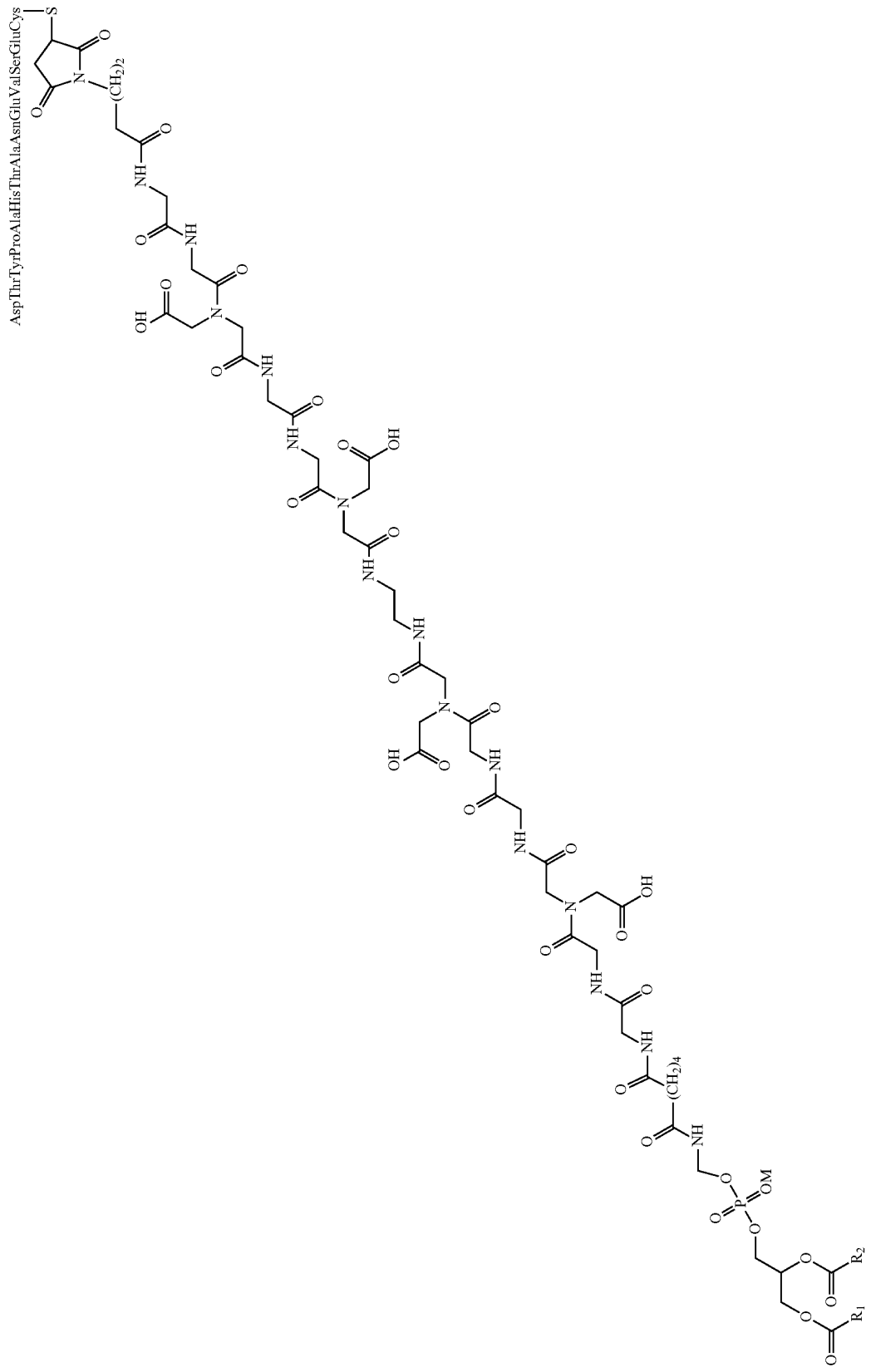

where $R_1$ and $R_2$ are both $(CH_2)_7CHCH(CH_2)_7$ and designated DOPE-Ad-CMG(2)-βAla-Mal-Mur(Dl4C) (XI).

In an exemplifying fourth embodiment of the second aspect the invention provides a peptide-lipid construct of the structure:

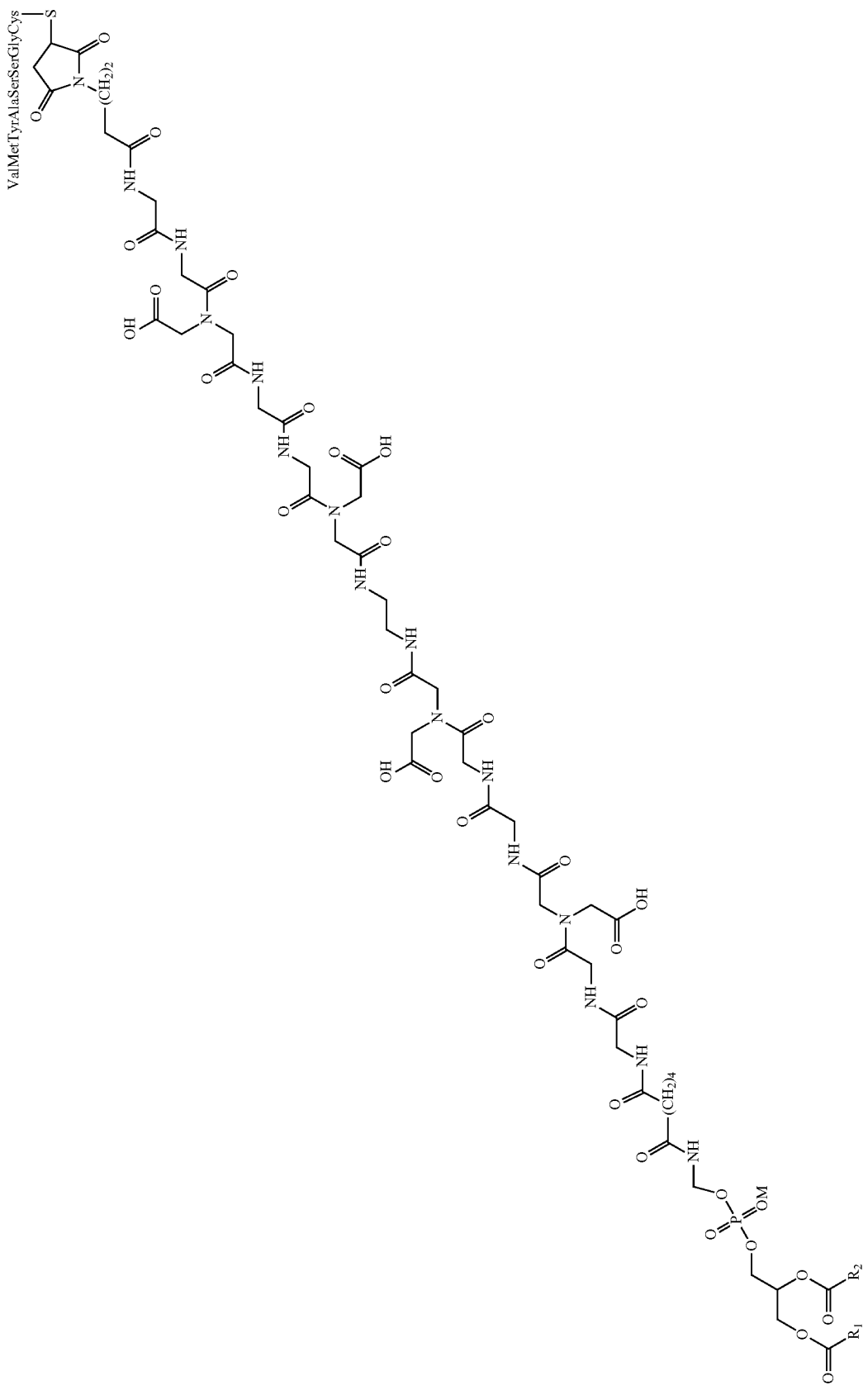

where $R_1$ and $R_2$ are both $(CH_2)_7CHCH(CH_2)_7$ and designated DOPE-Ad-CMG(2)-βAla-Mal-Syph(V8C) (XII).

In a third aspect the invention provides a method of detecting reactive antibody in the serum of a subject including the steps of:

Contacting a sample of the serum with a suspension of cells modified to incorporate a functional lipid construct (F-S-L) of the first or second alternatives of the first aspect of the invention or a peptide-lipid construct of the second aspect of the invention to provide a mixture;

Incubating the mixture for a time and at a temperature sufficient to allow agglutination; and Determining the degree of agglutination of the cells in the mixture;

where:

F is a carbohydrate or peptide comprising an epitope for the reactive antibody.

Optionally, the method includes the intermediate step of:

Adding an anti-subject globulin antibody to the mixture prior to determining the degree of agglutination of the cells of the mixture.

Preferably, the anti-subject globulin antibody is anti-human globulin (AHG) antibody.

Optionally, where F is a peptide, the method includes the preliminary step of:

Adding an amount of the peptide to the sample of the serum;

where the amount of the peptide is sufficient to neutralize non-specific agglutination or confirm specificity of the reactive antibody.

Preferably, the reactive antibody is reactive to an antigen selected from the group consisting of: Glycophorin A, Glycophorin B, or mutations thereof (including the MNS blood group system).

Preferably, the subject is a human.

Preferably, the cells are red blood cells.

In a third aspect the invention provides a method of preparing a peptide-lipid construct of the second aspect of the invention including the step of:

Reacting a peptide including a Cys residue with a functional lipid construct of the third alternative of the first aspect of the invention.

In a fourth aspect the invention provides a method of effecting qualitative and quantitative changes in the functional moieties expressed at the surface of a cell or a multi-cellular structure including the step of:

contacting the cell or multi-cellular structure with a solution of a functional lipid construct of the first aspect of the invention for a time and at a temperature sufficient to allow the construct to incorporate into the cell or multi-cellular structure.

In a fifth aspect the invention provides a method of immobilizing one or more cells or multi-cellular structures including the steps of:

Contacting the cells or multi-cellular structures with a solution of constructs of the fourth alternative of the first aspect of the invention for a time and at a temperature sufficient to allow an effective amount of the constructs to incorporate into the cells or multi-cellular structures to provide modified cells or multi-cellular structures; and Contacting the modified cells or multi-cellular structures with an avidin-coated substrate capable of being reversibly localized to a surface.

Preferably, the avidin-coated substrate is selected from the group consisting of: avidin-coated magnetic beads.

Preferably, the being reversibly localized to a surface is by application of a magnetic field.

In an embodiment of the fifth aspect the invention provides a method of immobilizing one or more cells or multi-cellular structures including the steps of:

Contacting the cells or multi-cellular structures with a dispersion of constructs of the structure:

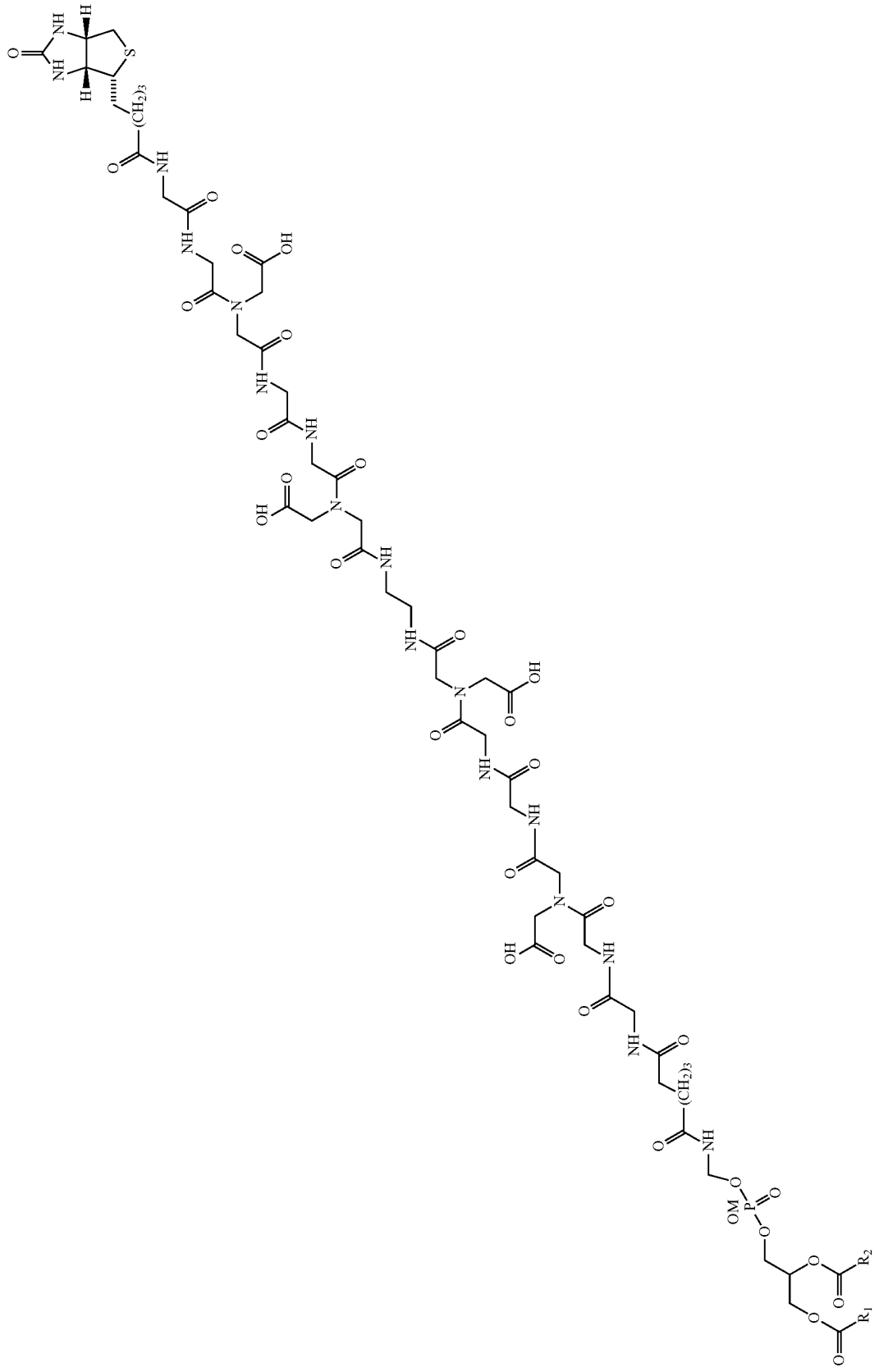

for a time and at a temperature sufficient to allow an effective amount of the construct to incorporate into the cells or multi-cellular structures to provide modified cells or multi-cellular structures;

Contacting the modified cells or multi-cellular structures with avidin-coated magnetic beads; and Applying a magnetic field to localize the beads to a surface;

where $R_1$ and $R_2$ are both $(CH_2)_7CHCH(CH_2)_7$.

In a sixth aspect the invention provides a method of promoting the aggregation of a first and second population of cells including the steps of:

Contacting the first population of cells with a solution of constructs of the fourth alternative of the first aspect of the invention for a time and at a temperature sufficient to allow an effective amount of the constructs to incorporate into the cells to provide modified cells of the first population;

Contacting the second population of cells with a solution of constructs of the fourth alternative of the first aspect of the invention for a time and at a temperature sufficient to allow an effective amount of the constructs to incorporate into the cells to provide modified cells of the first population;

Contacting the modified cells of one of the populations with an excess of avidin; and then Contacting the modified cells of the first and second populations. In an embodiment of the sixth aspect the invention provides a method of promoting the aggregation of a first and second population of cells including the steps of:

Contacting the first population of cells with a solution of constructs of the structure

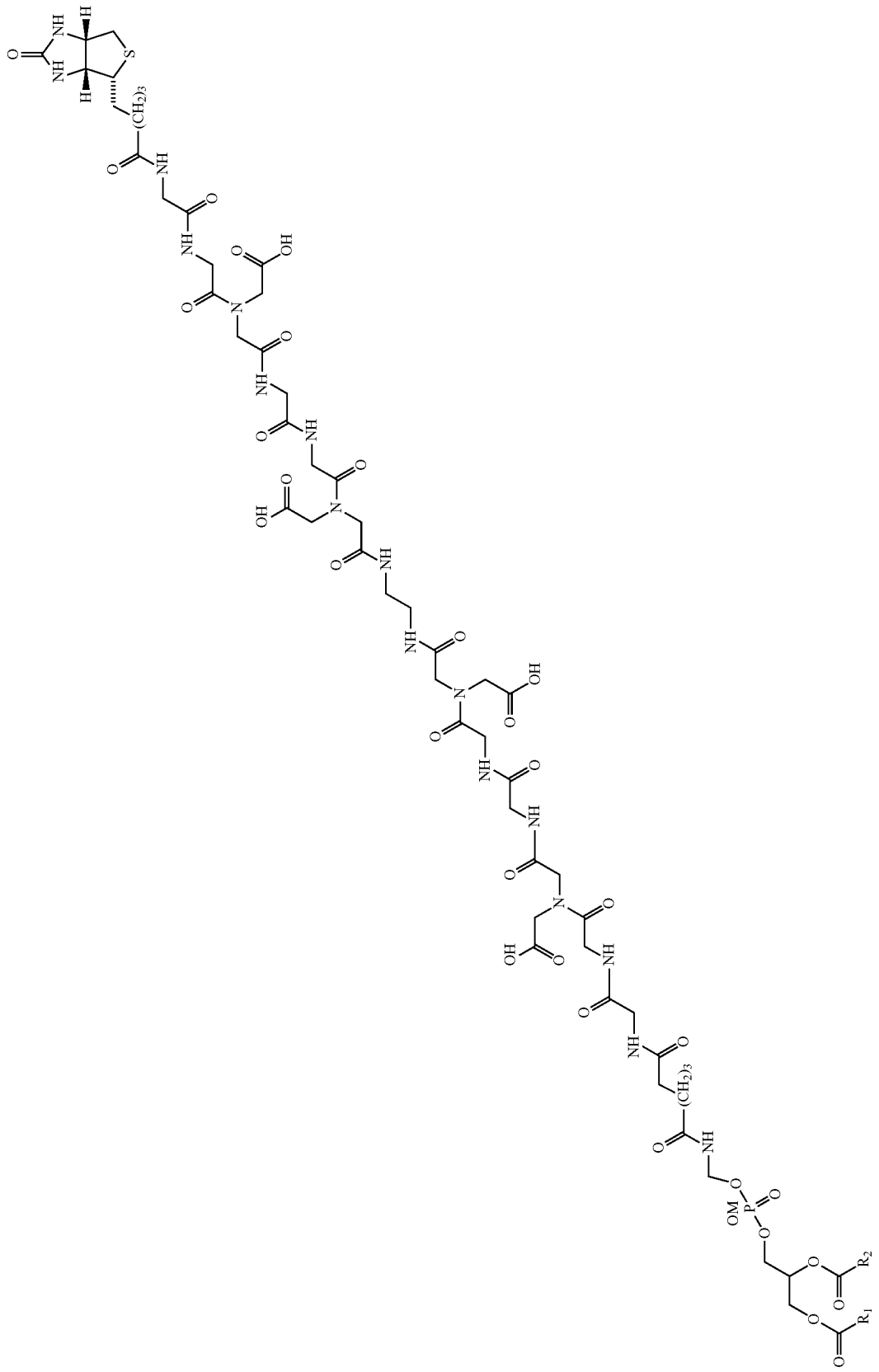

for a time and at a temperature sufficient to allow an effective amount of the constructs to incorporate into the cells to provide modified cells of the first population;

Contacting the second population of cells with a solution of the constructs for a time and at a temperature sufficient to allow an effective amount of the constructs to incorporate into the cells to provide modified cells of the first population;

Contacting the modified cells of one of the populations with an excess of avidin; and then Contacting the modified cells of the first and second populations.

In all aspects of the invention M is typically $H^+$, but may be replaced by another cation such as $Na^+$, $K^+$ or $NH_4^+$ or monovalent substituent such as $CH_3$. The notation M' excludes M being a monovalent substituent such as $CH_3$.

For the most part amino acid residues of peptides are identified according to Table 3 of Appendix 2 of Annex C of the *Administrative Instructions under the Patent Cooperation Treaty* dated 7 Feb. 2007 and in accordance with the convention:

H$_2$N-XaaXaaXaa . . . XaaXaaXaa-COOH

In Tables the corresponding one-letter codes for amino acid residues may be employed to provide Tables of acceptable dimensions.

In the description and claims of the specification the following acronyms, terms and phrases have the meaning provided:

"Avidins" means the biotin-binding tetrameric protein produced in the oviducts of birds, reptiles and amphibians and deposited in the whites of their eggs, its biotin-binding homomers and biotin-binding modified forms thereof including EXTRAVIDIN™, NEUTRAVIDIN™ and NEUTRALITE™.

"Biotin-binding" means non-covalent binding to the biotin moiety with a dissociation constant ($K_D$) under biocompatible conditions of the order $10^{-15}$ M.

"Diagnostic marker" means a molecule, the presence of which in a body fluid of a subject is diagnostic of a phenotype or pathological condition of the subject.

"Dispersible in biocompatible media" means capable of forming a stable, single phase system in a medium at a concentration sufficient to effect qualitative and quantitative changes in the functional moieties expressed at the surface of a cell or a multi-cellular structure without loss of vitality.

"(or one of its derivatives)" means a chemical modification of the chemical structure to provide a fluorophore with substantially equivalent physico-chemical properties, but modified spectral characteristics.

"MNS blood group system" means blood group antigens or epitopes of those antigens and mutations which are present on either glycophorin A, glycophorin B or mutations which result in glycophorin A/B hybrids.

"pcv" means packed cell volume.

"Proximal terminal sequence" means that portion of the peptide sequence proximal to the amino- or carboxy-terminus of the peptide (F).

"Reactive antibody" means an immunoglobulin, the presence of which in a body fluid of a subject is diagnostic of a phenotype or pathological condition of the subject.

"RBC" means red blood cells.

"Water soluble" means a stable, single phase system is formed when the construct is contacted with water or saline (such as PBS) at a concentration of at least 100 µg/ml and in the absence of organic solvents or detergents. The terms "soluble" and "dispersible" are used synonymously.

Exemplifying embodiments of the invention will now be described in detail with reference to the Figures of the accompanying drawings pages.

DETAILED DESCRIPTION

Figure 1:
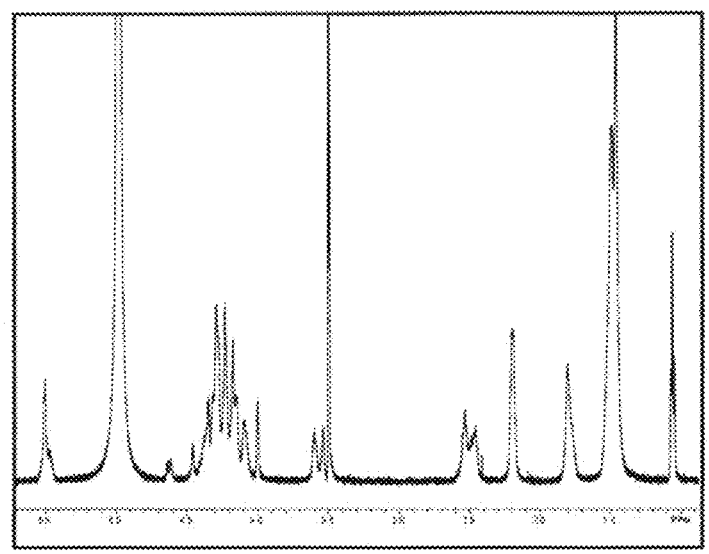
FIG. 1. $^1$H-NMR spectrum of the construct DOPE-Ad-CMG(I)amine (11) (5 mg/ml in D$_2$O/CD$_3$OD 2:1 δ ppm).
Figure 2:
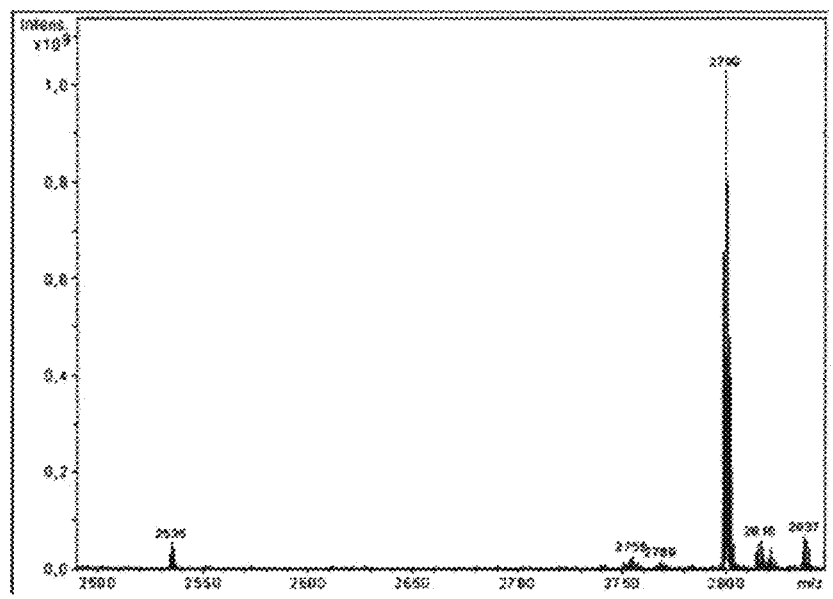
FIG. 2. MALDI-TOF MS spectrum of DOPE-Ad-CMG (I)-βAla-Mal-Syph(V8C) (XII) (FLEX-PC (Bruker), DHB).
Figure 3:
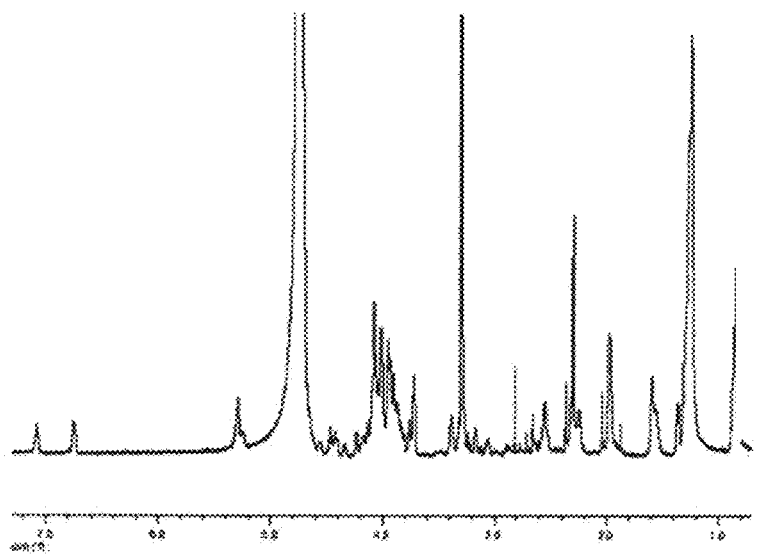
FIG. 3. $^1$H-NMR spectrum of the construct DOPE-Ad-CMG(I)-βAla-Mal-Syph(V8C) (XII) (7 mg/ml in D$_2$O/CD$_3$OD 4:1, pH c. 7.5; 600 MHz, 30° C., δ ppm).

The invention resides primarily in conjugating functional moieties to a diacyl or dialkyl lipid (L) via a spacer (S) to provide a construct (F-S-L) that is dispersible in biocompatible media, but will also spontaneously incorporate into the lipid bilayer of a cell membrane or multi-cellular structure.

The invention resides secondarily in the use of the selected structural motif (CMG) in the applications described and the advantages that accrue from using this structural motif and derivatives thereof.

Despite the advances in cell surface modification described in the specifications accompanying the international PCT applications referred to under the heading Background Art, the availability of constructs for use in the "one-step method", in particular peptide-lipid constructs, and the availability of BioG for use in the "two-step method", places a limitation on the broad application of these methods.

For example, a two-step method of localizing peptide antigen to the surface of cells or multi-cellular structures that avoids the use of BioG, or other conjugates obtained from biological sources, is desirable.

Although it was recognized that the biotinylation of the carbohydrate-lipid constructs described in the specification accompanying international application no. PCT/NZ2005/000052 provided a substitute for BioG in the "two-step method", it remains desirable to be able to use a biotin-lipid construct that has the favourable properties of these biotinylated carbohydrate-lipid constructs and could be used in the "one-step method".

In contrast with the preparation of constructs where the function (F) is a carbohydrate, the preparation of constructs where F is a peptide presents additional technical problems.

Firstly, it is desirable for the peptide (F) ligated to the L-S or S-L moiety to be dispersible in water such as a buffered solution of solutes, e.g. PBS, or at least a biocompatible solvent.

Overcoming this difficulty may require the selection of a proximal terminal sequence (PTS) to promote solubility without modifying the desired biological properties of the construct.

Secondly, it is desirable for the peptide-lipid construct to be dispersible in water, or at least a biocompatible buffered solution or serum, according to the requirements of the proposed application (i.e. it is desirable for the construct to be "water soluble" as defined herein).

Overcoming this difficulty requires the selection of a spacer (S) to promote solubility of the construct.

Thirdly, where the proposed application is the modification of cells such as red blood cells (RBCs) for use in diagnostic applications, or as quality controls in blood group typing, it is required for the construct to be dispersible in a biocompatible buffered solution without participating in antigen-antibody cross reactivity not specific to the diagnostic peptide or blood group type antigen.

Satisfying this requirement requires the identification of suitable structural motifs for the spacer (S) and/or proximal terminal sequence (PTS) when the latter is present.

Where the application is for use in the modification of the surface of cells or multi-cellular structures (e.g. an embryo) with a view to promoting the association of the modified cell or modified multi-cellular structure with a target surface (e.g. the endometrium) exposing the cell or multi-cellular structure to solvents or buffered solutions that are not biocompatible must be avoided.

Fourthly, the presentation of the peptide of the peptide lipid construct at the surface of the modified cell or multi-cellular structure will have an influence on the extent of cross reactivity with diagnostic markers.

The ability to localise peptides to the surface of cells or multi-cellular structures via a residue proximal to either the N- or C-terminus of the peptide may allow the naturally occurring configuration of the peptide sequence relative to the cell surface to be approximated.

The presentation of the peptide sequence in the tertiary (or quaternary) structure of the parent polypeptide (or protein) may therefore be mimicked. It is contemplated that peptides may be localised to the surface of cells via multiple residues. For example, where both a residue proximal to the amino terminus and a residue proximal to the carboxyl terminus are used to localise the peptide a "looped" configuration of the peptide may be promoted at the surface.

The poly-ethylene glycol (PEG) spacer of known peptide-lipid constructs is selected to provide solubility. However, polymers of PEG may interfere with the expression and function of the peptide at the surface.

The as yet unpublished specification accompanying international application number PCT/NZ2008/000239 describes the preparation of peptide-lipid constructs for use in methods of effecting qualitative and quantitative changes in the level of peptides expressed at the surface of cells and multi-cellular structures where an oligomer of ethylene glycol is used as a spacer covalently linking lipid of the construct to the peptide moiety. The use of the constructs to prepare cells for use in serodiagnosis is described.

In the peptide-lipid constructs of the present invention the structural motif designated CMG is used as a component $(S_1)$ of the spacer (S) covalently linking the lipid (L) and peptide (F). Inclusion of this structural motif provides a degree of rigidity to the spacer, distancing the functional moiety (peptide) of the peptide-lipid construct from the surface of the modified cell or multi-cellular structure.

It will be recognized that this attribute of the invention may be favourably applied to the development of other functional lipid constructs as demonstrated here with reference to the use of constructs including this structural motif where the functional moiety is a carbohydrate, such as the glycotope of the antigens of the ABO blood grouping, a fluorophore such as fluorescein (or one of its derivatives), or a conjugator, such as biotin.

Biotin ([3aS-(3aα, 4β, 6aα)]-hexahydro-2-oxo-1H-thieno[3,4-d]imidazole-4-pentanoic acid) is a water soluble vitamin of the B complex, also referred to as vitamin H. Biotin is a growth factor present in minute amounts in every living cell. The compound plays an indispensible role in numerous naturally occurring carboxylation reactions, including the production of fatty acids.

Biotin has a solubility (25° C.) in water of approximately 22 mg/100 mL and approximately 80 mg/100 mL in 95% alcohol. The compound has increased solubility in hot water and in dilute alkali, but is relatively insoluble in other common organic solvents. The ability to localize this functional moiety to the surface of cells and multi-cellular structures provides a number of applications as demonstrated.

Whilst not wishing to be bound by theory it is believed that the properties of the functional lipid constructs may be modified and refined to suit particular applications by by selection of the cation $(M^+)$ or derivation of the free carboxyl groups of the structural motif to provide modified structural motifs, e.g. by substitution with methyl $(CH_3$; MCMG).

The properties of the functional-lipid constructs for use in the claimed methods must be such that they can be readily dispersed in biologically compatible media in the absence of solvents or detergents, but incorporate into the lipid bilayer of a membrane when a solution of the construct is contacted with a suspension of cells or multi-cellular.

Peptide-lipid constructs with these potentially conflicting properties are prepared by selection of other components of the spacer (S) in addition to the inclusion of the unmodified (CMG) or modified (e.g. MCMG) structural motif and/or the inclusion of a proximal terminal sequence (PTS) in the peptide (F).

The preparation of the peptide-lipid constructs where S is linked to F via a sulphide bond formed with a terminal Cys (Cys) residue of the peptide at the carboxy-terminus of the peptide is preferred as the peptide is less prone to oxidation.

A range of peptides may therefore be prepared as peptide-lipid constructs for use in methods of effecting qualitative and quantitative changes in the levels of peptide expressed at the surface of cells and multi-cellular structures.

A particular advantage of the biotin-lipid constructs is that they permit cells or multi-cellular structures to be localized to surfaces with minimal detriment to the biological activity and viability of the cells or multi-cellular structure.

Examples of the localization of cells to a surface are provided. It will be noted that where the localization to a surface is achieved by means of avidin-coated magnetic beads the localization is reversible, thereby providing the opportunity to control the selection and positioning of cells on a surface.

The utility of the constructs in sub-cellular fractionation and localization of membrane bound organelles to surfaces is contemplated. The utility of the constructs in promoting the aggregation of populations of cells as may be required in the generation of hybridomas is also contemplated.

It will be understood that for a non-specific interaction, such as the interaction between diacyl- or dialkyl-glycero-lipids or glycerophospholipids and a membrane, structural and stereo-isomers of naturally occurring lipids can be functionally equivalent.

For example, it is contemplated that diacylglycerol 2-phosphate could be substituted for phosphatidate (diacylglycerol 3-phosphate). Furthermore it is contemplated that the absolute configuration of phosphatidate can be either R or S.

The structural motif (CMG) may be prepared by the method summarized in Scheme I and Scheme II to provide the substructures designated MCMG(1) and CMG(2).

Chemistry

The preparation of the structural motif, the preparation of functional-lipid constructs utilizing this structural motif, and the use of these constructs in chemical and biological applications is described below Preparation of the Structural Motif Designated CMG Materials and Methods Acetone, benzene, chloroform, ethylacetate, methanol, toluene and o-xylene were from Chimmed (Russian Federation). Acetonitrile was from Cryochrom (Russian Federation). DMSO, DMF, $CF_3COOH$, $Et_3N$, N,N'-dicyclohexylcarbodiimide and N-hydroxysuccinimide were from Merck (Germany). Iminodiacetic acid dimethyl ester hydrochloride was from Reakhim (Russian Federation).

Dowex 50×4-400 and Sephadex LH-20 were from Amersham Biosciences AB (Sweden). Silica gel 60 was from Merck (Germany). Tetraamine $(H_2N-CH_2)_4C \times 2H_2SO_4$ was synthesized as described by Litherland et al. (1938). Thin-layer chromatography was performed using silica gel 60 $F_{254}$ aluminium sheets (Merck, 1.05554) with detection by charring after 7% $H_3PO_4$ soaking.

Preparation of {[2-(2-tert-butoxycarbonylamino-acetylamino)-acetyl]-methoxycarbonylmethyl-amino}-acetic acid methyl ester (SCHEME I)

To a stirred solution of (methoxycarbonylmethyl-amino)-acetic acid methyl ester hydrochloride (988 mg, 5 mmol) in DMF (15 ml) were added Boc-GlyGlyNos (3293 mg, 10 mmol) and $(CH_3CH_2)_3N$ (3475 µL, 25 mmol) were added. The mixture was stirred overnight at room temperature and then diluted with o-xylene (70 ml) and evaporated.

Flash column chromatography on silica gel (packed in toluene, and eluted with ethyl acetate) resulted in a crude product. The crude product was dissolved in chloroform and washed sequentially with water, 0.5 M $NaHCO_3$ and saturated KCl.

The chloroform extract was evaporated and the product purified on a silica gel column (packed in chloroform and eluted with 15:1 (v/v) chloroform/methanol). Evaporation of the fractions and drying under vacuum of the residue provided a colourless thick syrup. Yield 1785 mg, (95%). TLC: $R_f$=0.49 (7:1 (v/v) chloroform/methanol).

$^1$H NMR (500 MHz, [$D_6$]DMSO, 30° C.) δ, ppm: 7.826 (t, J=5.1 Hz, 1H; NHCO), 6.979 (t, J=5.9 Hz, 1H; NHCOO), 4.348 and 4.095 (s, 2H; NCH$_2$COO), 3.969 (d, J=5.1 Hz, 2H; COCH$_2$NH), 3.689 and 3.621 (s, 3H; OCH$_3$), 3.559 (d, J=5.9 Hz, 2H; COCH$_2$NHCOO), 1.380 (s, 9H; C(CH$_3$)$_3$).

Preparation of {[2-(2-tert-butoxycarbonylamino-acetylamino)-acetyl]-methoxycarbonylmethyl-amino}-acetic acid To a stirred solution of {[2-(2-tert-butoxycarbonylamino-acetylamino)-acetyl]-methoxycarbonylmethyl-amino}-acetic acid methyl ester (1760 mg, 4.69 mmol) in methanol (25 ml) 0.2 M aqueous NaOH (23.5 ml) was added and the solution kept for 5 min at room temperature. The solution was then acidified with acetic acid (0.6 ml) and evaporated to dryness.

Column chromatography of the residue on silica gel (packed in ethyl acetate and eluted with 2:3:1 (v/v/v) i-PrOH/ethyl acetate/water) resulted in a recovered {[2-(2-tert-butoxycarbonylamino-acetylamino)-acetyl]-methoxycarbonylmethyl-amino}-acetic acid methyl ester (63 mg, 3.4%) and target compound (1320 mg). The intermediate product was then dissolved in methanol/water/pyridine mixture (20:10:1, 30 ml) and passed through an ion exchange column (Dowex 50×4-400, pyridine form, 5 ml) to remove residual sodium cations.

The column was then washed with the same solvent mixture, the eluant evaporated, the residue dissolved in chloroform/benzene mixture (1:1, 50 ml) and then evaporated and dried under vacuum. Yield of 10 was 1250 mg (74%), white solid. TLC: $R_f$=0.47 (4:3:1 (v/v/v) i-PrOH/ethyl acetate/water).

$^1$H NMR (500 MHz, [$D_6$]DMSO, 30° C.), mixture of cis- and trans-conformers of N-carboxymethylglycine unit c.3:1. Major conformer; δ, ppm: 7.717 (t, J=5 Hz, 1H; NHCO), 7.024 (t, J=5.9 Hz, 1H; NHCOO), 4.051 (s, 2H; NCH$_2$COOCH$_3$), 3.928 (d, J=5 Hz, 2H; COCH$_2$NH), 3.786 (s, 2H; NCH$_2$COOH), 3.616 (s, 3H; OCH$_3$), 3.563 (d, J=5.9 Hz, 2H; COCH$_2$NHCOO), 1.381 (s, 9H; C(CH$_3$)$_3$) ppm; minor conformer, δ=7.766 (t, J=5 Hz, 1H; NHCO), 7.015 (t, J=5.9 Hz, 1H; NHCOO), 4.288 (s, 2H; NCH$_2$COOCH$_3$), 3.928 (d, J=5 Hz, 2H; COCH$_2$NH), 3.858 (s, 2H; NCH$_2$COOH), 3.676 (s, 3H; OCH$_3$), 3.563 (d, J=5.9 Hz, 2H; COCH$_2$NHCOO), 1.381 (s, 9H; C(CH$_3$)$_3$).

Preparation of {[2-(2-tert-Butoxycarbonylamino-acetylamino)-acetyl]-methoxycarbonylmethyl-amino}-acetic acid N-oxysuccinimide ester (Boc-Gly$_2$(MCMGly)Nos)

To an ice-cooled stirred solution of {[2-(2-tert-butoxycarbonylamino-acetylamino)-acetyl]-methoxycarbonylmethyl-amino}-acetic acid (1200 mg, 3.32 mmol) and N-hydroxysuccinimide (420 mg, 3.65 mmol) in DMF (10 ml) was added N,N'-dicyclohexylcarbodiimide (754 mg, 3.65 mmol). The mixture was stirred at 0° C. for 30 min, then for 2 hours at room temperature.

The precipitate of N,N'-dicyclohexylurea was filtered off, washed with DMF (5 ml), and filtrates evaporated to a minimal volume. The residue was then agitated with $(CH_3CH_2)_2O$ (50 ml) for 1 hour and an ether extract removed by decantation. The residue was dried under vacuum providing the active ester (1400 mg, 92%) as a white foam. TLC: $R_f$=0.71 (40:1 (v/v) acetone/acetic acid).

$^1$H NMR (500 MHz, [$D_6$]DMSO, 30° C.), mixture of cis- and trans-conformers of N-carboxymethylglycine unit c. 3:2.

Major conformer; δ, ppm: 7.896 (t, J=5.1 Hz, 1H; NHCO), 6.972 (t, J=5.9 Hz, 1H; NHCOO), 4.533 (s, 2H; NCH$_2$COON), 4.399 (s, 2H; NCH$_2$COOCH$_3$), 3.997 (d, J=5.1 Hz, 2H; COCH$_2$NH), 3.695 (s, 3H; OCH$_3$), 3.566 (d, J=5.9 Hz, 2H; COCH$_2$NHCOO), 1.380 (s, 9H; C(CH$_3$)$_3$).

Minor conformer; δ, ppm: 7.882 (t, J=5.1 Hz, 1H; NHCO), 6.963 (t, J=5.9 Hz, 1H; NHCOO), 4.924 (s, 2H; NCH$_2$COON), 4.133 (s, 2H; NCH$_2$COOCH$_3$), 4.034 (d, J=5.1 Hz, 2H; COCH$_2$NH), 3.632 (s, 3H; OCH$_3$), 3.572 (d, J=5.9 Hz, 2H; COCH$_2$NHCOO), 1.380 (s, 9H; C(CH$_3$)$_3$).

The active ester (1380 mg) was dissolved in DMSO to provide a volume of 6 ml and used as a 0.5 M solution (stored at −18° C.).

Preparation of CMG(2) diamine

A solution of ethylenediamine (808 mg, 13.47 mmol) and Et$_3$N (1.87 ml, 13.5 mmol) in DMSO (5 ml) was added to a stirred solution of Boc-Gly$_2$-(MCM)Gly-OSu (15.42 g, 33.68 mmol) in DMSO (50 ml). The reaction mixture was stirred for 30 min at ambient temperature and acidified with acetic acid (1.2 ml), then fractionated with Sephadex LH-20 column (column volume 1200 ml, eluent-MeOH/water 2:1+ 0.2% AcOH). Fractions containing compound Boc$_2$MCMG were combined, solvents evaporated and the residue was concentrated in vacuum. The product was additionally purified by silica

SCHEME I

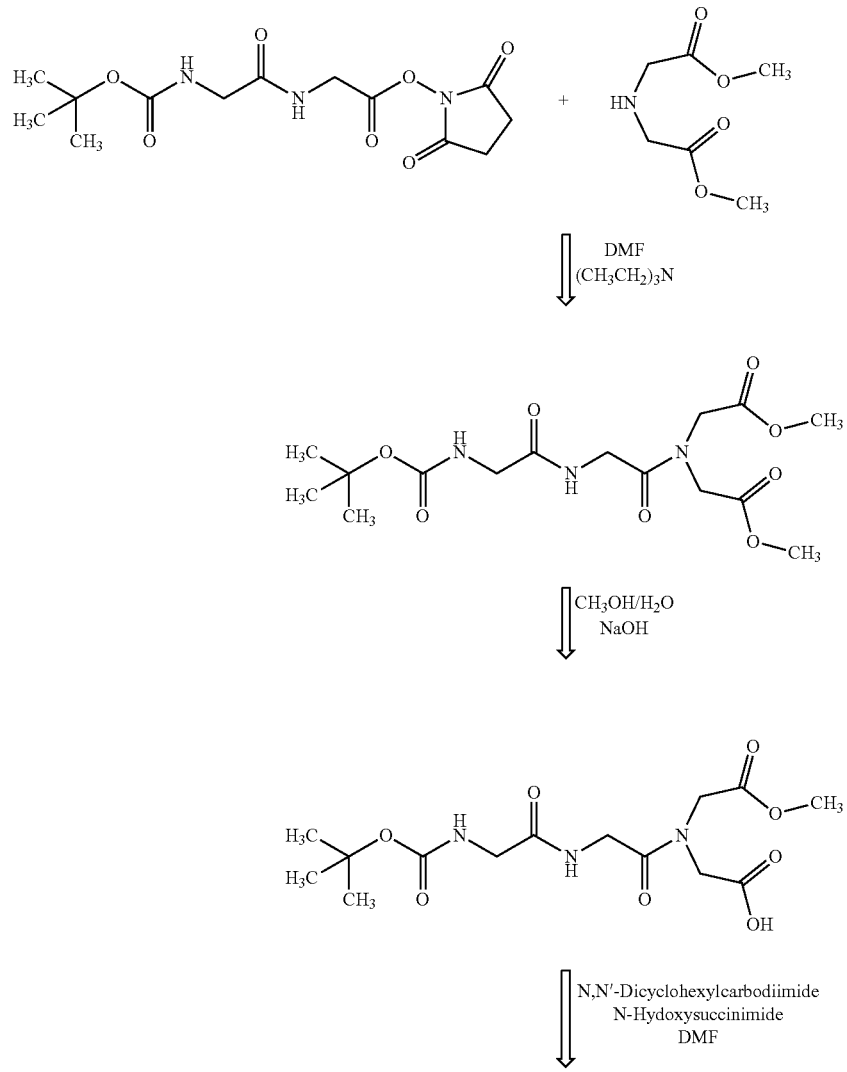

-continued
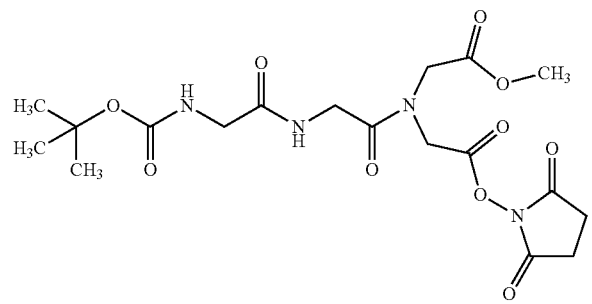
SCHEME II
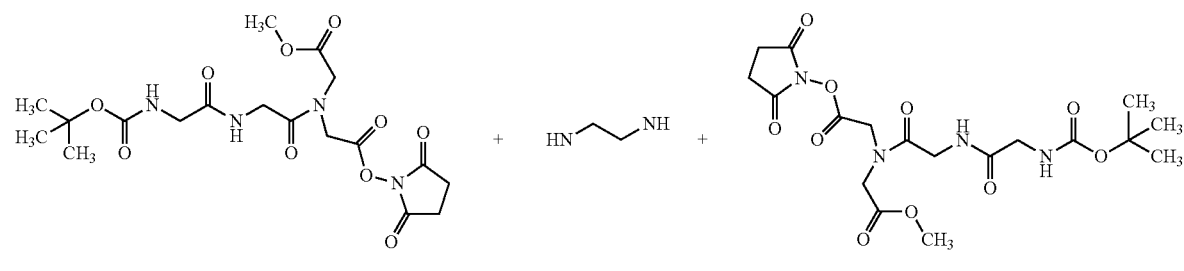
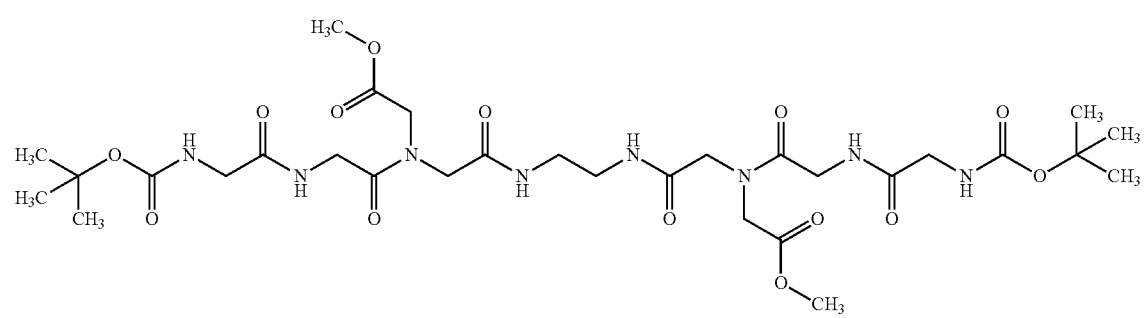
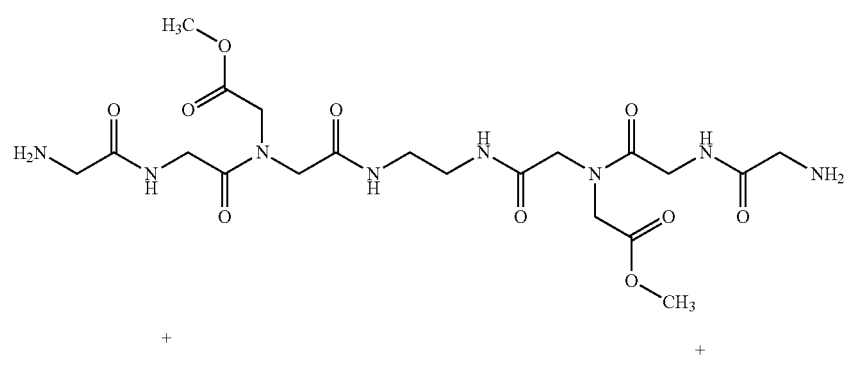
+                                          +

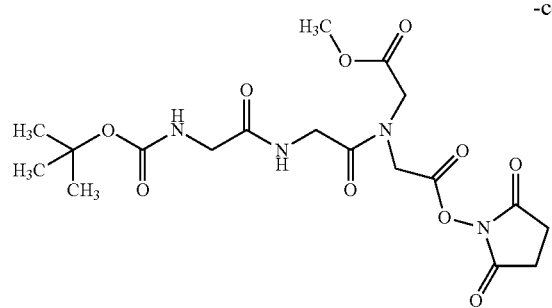
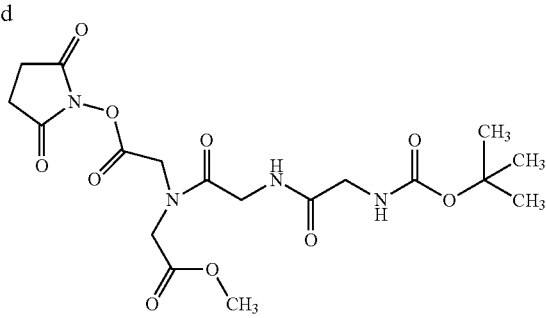
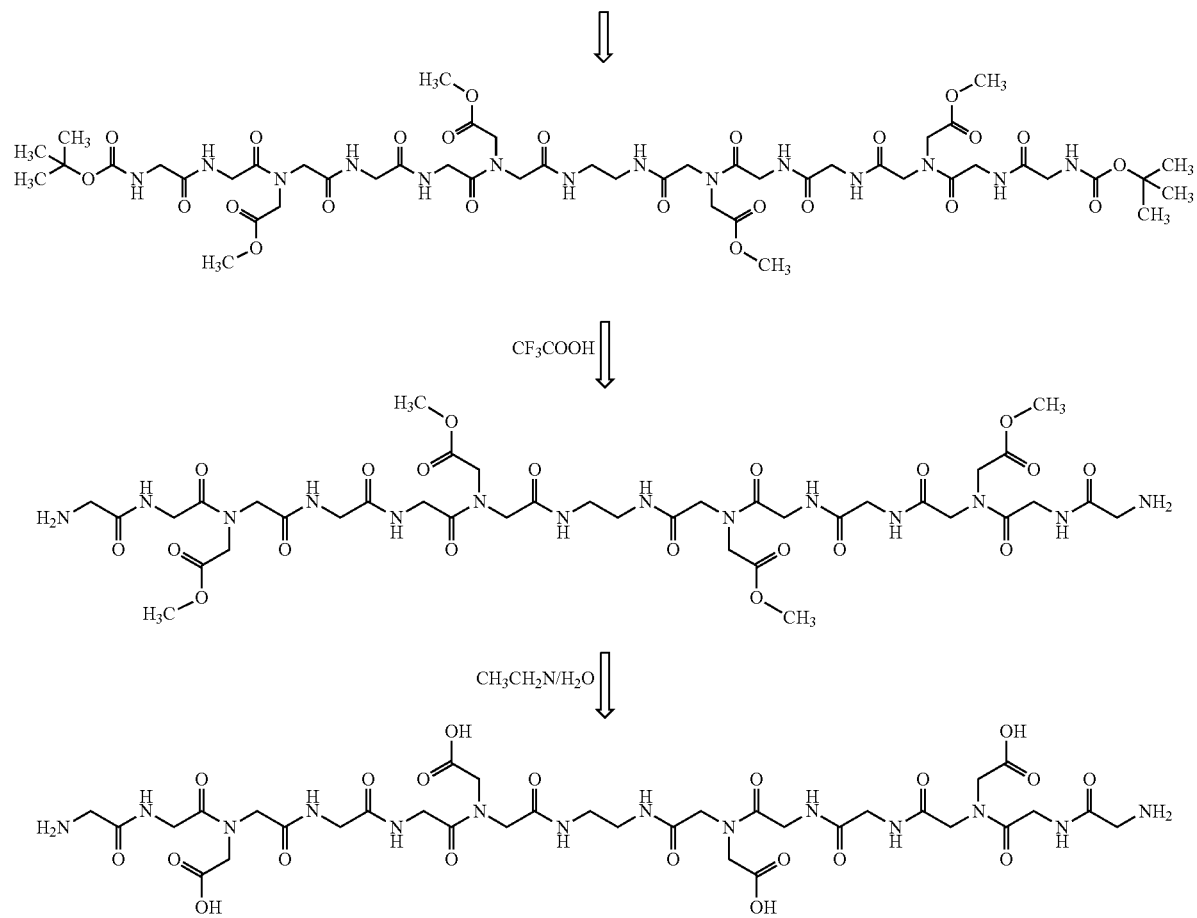

gel column chromatography using 2-propanol/ethyl acetate/water (2:6:1) as eluent. Fractions containing pure Boc₂MCMG were combined, solvents evaporated and a residue was dried in vacuum to give target Boc₂MCMG as colourless foam (8.41 g, 84%). TLC: $R_f$=0.48 (ⁱPrOH/ethyl acetate/water 2:3:1).

¹H NMR (500 MHz, [D₆]DMSO, 30° C.), mixture of conformers ~3:2: 8.166, 8.125, 7.917 and 7.895 (m, total 2H; 2 CONHCH₂), 7.793 (m, 2H; NHCH₂CH₂NH), 7.001 (br. t, 2H; 2 NHCOO), 4.277-3.893 (total 12H; 2 CH₂COO, 4 NCH₂CO), 3.690 and 3.635 (s, total 6H; 2 COOCH₃), 3.567 (d, J=5.8 Hz, 4H; 2 CH₂NHCOO), 3.131 (m, 4H; NHCH₂CH₂NH), 1.379 (s, 18H; 2 C(CH₃)₃) ppm.

MS, m/z: 769 [M+Na], 785 [M+K].

Trifluoroacetic acid (25 ml) was added to a stirred solution of Boc₂MCMG (4.88 g, 6.535 mmol) in methylene chloride (25 ml) and the solution was kept for 1 h at ambient temperature. Then a reaction mixture was concentrated and the residue was evaporated three times with anhydrous MeOH (50 ml), then a residue was extracted three times with Et₂O (100 ml) to remove traces of trifluoroacetic acid. The resulted precipitate (as a white solid) was dried to give 5.06 g (~100%) of MCMG as bis-trifluoroacetic salt. TLC: $R_f$=0.23 (ethanol/water/pyridine/acetic acid 5:1:1:1).

¹H NMR (500 MHz, D₂O, 30° C.), mixture of conformers ~5:4: 4.400-4.098 (total 12H; 2 CH₂COO, 4 NCH₂CO), 3.917 (s, 4H; 2 COCH₂NH₂), 3.829 and 3.781 (s, total 6H; 2 COOCH₃), 3.394 (m, 4H; NHCH₂CH₂NH) ppm.

MS, m/z: 547 [M+H], 569 [M+Na], 585 [M+K].

A solution of Boc-Gly₂-(MCM)Gly-OSu (7.79 g, 16.994 mmol) in DMSO (17 ml) and Et₃N (2.83 ml, 20.4 mmol) was added to the stirred solution of MCMG (13) (5.06 g, 6.796 mmol) in DMSO (13 ml). The reaction mixture after stirring for 2 h at ambient temperature was acidified with acetic acid (4.0 ml) and fractionated with Sephadex LH-20 column chromatography (column volume 1200 ml, eluent-MeOH/water 2:1+0.2% AcOH). Fractions containing pure Boc$_2$MCMG were combined, solvents evaporated and the residue was dried in vacuum to give target Boc$_2$MCMG as colourless foam (8.14 g, 97%). TLC: R$_f$=0.25 ($^i$PrOH/ethyl acetate/water 2:3:1).

$^1$H NMR (500 MHz, [D$_6$]DMSO, 30° C.), mixture of conformers: 8.393-7.887 (total 6H; 6 CONHCH$_2$), 7.775 (m, 2H; NHCH$_2$CH$_2$NH), 6.996 (br. t, 2H; 2 NHCOO), 4.299-3.730 (total 28H; 4 CH$_2$COO, 10 NCH$_2$CO), 3.691 and 3.633 (s, total 12H; 4 COOCH$_3$), 3.564 (d, J=5.8 Hz, 4H; 2 CH$_2$NHCOO), 3.129 (m, 4H; NHCH$_2$CH$_2$NH), 1.380 (s, 18H; 2 C(CH$_3$)$_3$) ppm.

MS, m/z: 1256 [M+Na], 1271 [M+K].

Boc$_2$MCMG (606 mg, 0.491 mmol) was dissolved in CF$_3$COOH (2 ml) and the solution was kept for 30 min at r.t. Trifluoroacetic acid was evaporated in vacuum and the residue was extracted three times with Et$_2$O (trituration with 25 ml of Et$_2$O followed by filtration) to remove residual CF$_3$COOH and the obtained white powder was dried in vacuum. The powder was dissolved in 4 mL of water and then was freeze-dried. Yield of MCMG (TFA salt) was estimated as quantitative (actual weight was larger than theoretical by ~10% due to stability of hydrates). TLC: R$_f$=0.21 (ethanol/water/pyridine/acetic acid 5:1:1:1).

$^1$H NMR (500 MHz, [D$_2$]H$_2$O, 30° C.), mixture of conformers: 4.430-4.014 (total 28H; 4 CH$_2$COO, 10 NCH$_2$CO), 3.911 (s, 4H; 2 COCH$_2$NH$_2$), 3.823 and 3.772 (s, total 12H; 4 COOCH$_3$), 3.386 (m, 4H; NHCH$_2$CH$_2$NH) ppm.

MS, m/z: 1034 [M+H], 1056 [M+Na].

To the solution of MCMG (~0.49 mmol) in water (20 mL) Et$_3$N (0.5 mL) was added, and the solution was kept for 15 h at r.t. The reaction mixture was evaporated to dryness and the residue was desalted on Sephadex LH-20 column (two methods):

Method A. The residue was dissolved in water (3 ml) and the solution was desalted on Sephadex LH-20 column (column volume 250 mL, eluent-MeOH/water 1:1+0.05 M pyridine acetate). Fractions, containing CMG contaminated with salts were combined separately, evaporated and the residue was desalted again. Combined fractions, containing pure CMG, were evaporated to ~4 ml volume and freeze dried. Yield of CMG (internal salt) was 431 mg (90%).

Method B. The residue was dissolved in water (3 ml) and the solution was desalted on Sephadex LH-20 column (column volume 250 mL, eluent-MeOH/water 1:1+1% conc. aq. NH$_3$). Fractions, containing pure CMG, were evaporated to ~4 ml volume and freeze dried. The residue (ammonia salt of CMG (16)) was dissolved in $^i$PrOH/water 1:1 mixture (10 mL), Et$_3$N (0.2 mL) was added, and the solution was evaporated to dryness. This procedure was repeated twice; the residue was dissolved in 4 mL of water and freeze-dried. Yield of the di-Et$_3$N salt of CMG was 549 mg (95%).

TLC: R$_f$=0.50 ($^i$PrOH/MeOH/acetonitrile/water 4:3:3:4+ 3% conc. aq. NH$_3$), or R$_f$=0.43 ($^i$PrOH/EtOH/MeOH/water 1:1:1:1, 0.75M NH$_3$).

$^1$H NMR of CMG internal salt (500 MHz, [D$_2$]H$_2$O, 30° C.), mixture of conformers: 4.328-4.006 (total 28H; 4 CH$_2$COO, 10 NCH$_2$CO), 3.907 (s, 4H; 2 COCH$_2$NH$_2$), 3.381 (m, 4H; NHCH$_2$CH$_2$NH) ppm.

MS, m/z: 977 [M+H], 999 [M+Na], 1015 [M+K].

Preparation of DOPE-Ad-CMG(I)amine

DOPE-Ad-CMG(2)amine was prepared from {[2-(2-tert-butoxycarbonylamino-acetylamino)-acetyl]-methoxycarbonylmethyl-amino}-acetic acid N-oxysuccinimide ester Boc-Gly$_2$(MCMGly)Nos according to Scheme III.

Preparation of H$_2$N-CMG-DOPE

To the intensively stirred solution of CMG (16) (425 mg, 0.435 mmol of internal salt) in i-PrOH/water mixture (i-PrOH/water 3:2, 10 mL) the 1 M aq. solution of NaHCO$_3$ (0.435 mL, 0.435 mmol) and then the solution of DOPE-Ad-OSu (211 mg, 0.218 mmol) in dichloroethane (0.4 mL) were added. The reaction mixture was stirred for 2 h and then acidified with 0.2 mL of AcOH and evaporated to minimal volume at 35° C. The solid residue was dried in vacuum (solid foam) and then thoroughly extracted with CHCl$_3$/MeOH mixture (CHCl$_3$/MeOH 4:1, several times with 10 mL, TLC control). The extracted residue consisted of unreacted CMG(2) and salts (about 50% of CMG was recovered by desalting of combined the residue and a fractions after chromatography on silica gel according to procedure described in the CMG synthesis.). The combined CHCl$_3$/MeOH extracts (solution of CMG-Ad-DOPE amine, DOPE-Ad-CMG-Ad-DOPE, N-oxysuccinimide and some CMG) were evaporated in vacuum and dried. The obtained mixture was separated on silica gel column (2.8×33 cm, ~200 mL of silica gel in CHCl$_3$/MeOH 5:1). The mixture was placed on column in MeOH/CHCl$_3$/water mixture (MeOH/CHCl$_3$/water 6:3:1+0.5% of pyridine) and the components were eluted in a stepwise ternary gradient: MeOH/CHCl$_3$/water composition from 6:3:1 to 6:2:1 and then to 6:2:2 (all with 0.5% of pyridine). DOPE-Ad-CMG-Ad-DOPE was eluted first (R$_f$=0.75, MeOH/CHCl$_3$/water 3:1:1), followed by desired DOPE-Ad-CMG amine (R$_f$=0.63, MeOH/CHCl$_3$/water 3:1:1), last eluted was CMG (R$_f$=0.31, MeOH/CHCl$_3$/water 3:1:1). Fractions, containing pure CMG-Ad-DOPE amine (20) were combined and evaporated to dryness. To remove any low molecular weight impurities and solubilised silica gel the residue was dissolved in $^i$PrOH/water 1:2 mixture (2 mL), and was passed through Sephadex LH-20 column (column volume 130 mL, eluent-$^i$PrOH/water 1:2+0.25% of pyridine). Fractions containing pure CMG-Ad-DOPE amine were combined and evaporated (~20% of 2-propanol was added to prevent foaming) to dryness, the residue was dissolved in water (~4 mL) and freeze-dried. Yield of CMG-Ad-DOPE amine was 270 mg (68% on DOPE-Ad-OSu or 34% on CMG(16)).

$^1$H NMR (500 MHz, [D$_2$]H$_2$O/[D4]CH$_3$OH 2:1, 30° C.): 5.505 (m, 4H; 2 CH$_2$CH=CHCH$_2$), 5.476 (m, 1H; OCH$_2$C HCH$_2$O), 4.626 (dd, J$_{gem}$=11.6 Hz, 1H; OCHCHCH$_2$O), 4.461-4.084 (total 37H; 4 CH$_2$COO, 11 NCH$_2$CO, OC HCHCH$_2$O, OCH$_2$CH$_2$N), 4.002 (s, 2H; COCH$_2$NH$_2$), 3.573 (m, 4H; NHCH$_2$CH$_2$NH), 2.536-2.463 (m, total 8H; 4 CH$_2$CO), 2.197 (m, 8H; 2 CH$_2$CH=CHCH$_2$), 1.807 (m, 8H; 4 CH$_2$CH$_2$CO), 1.480 (m, 40H; 20 CH$_2$), 1.063 (~t, J≈6 Hz, 6H; 2 CH$_3$) ppm.

MS, m/z: 1831 [M+H].

Preparation of Functional Lipid Constructs (F-S-L) where F is a Peptide

Preparation of DOPE-Ad-CMG(2)-βAla-Mal-Milt(K,M) (X)

The construct DOPE-Ad-CMG(2)-βAla-Mal-Milt(K,M) (X) was prepared according to Scheme IV.

DOPE-Ad-CMG(2) amine was treated with 5-fold excess of 3-maleimidopropionic acid oxybenztriazol ester in i-PrOH-water.

Conversion of DOPE-Ad-CMG(2) into was somewhat low maleimido-derivative (about 70%), presumably due to fast hydrolysis of the intermediate promoted by the amount of organic base, diisopropylethylamine, required to be added to keep DOPE-Ad-CMG(2) in solution.

The maleimido-derivative was isolated in 40% yield after gel-permeation chromatography on Sephadex LH-20 (i-PrOH-water, 1:2).

Initially, the conjugation of the maleimido-derivative with peptide was attempted using i-PrOH-TRIS buffer, pH 8 (1:2), but the intermediate appeared to be almost insoluble in this medium. However, addition of pyridin (1 μl/mg of intermediate) resulted in immediate dissolution of reactants and a surprisingly clean and substantially complete conversion.

Notably, although no reducing agent was used to prevent oxidative deactivation of the peptide, MS analysis of the whole reaction mixture revealed no traces of S-S dimer.

The desired construct (X) was purified on a Sephadex LH-20 column. A solubility problem was again encountered as fractions containing (X) were slightly opaque.

This would appear to indicate that the amount of base added to the eluent was insufficient to keep compounds properly charged and soluble in the concentration range of 1-5 mg/ml.

The structure of purified construct (X) was unambiguously established by NMR and MS spectra.

NMR spectrum revealed the expected peptide: DOPE ratio as deduced from the signal ratio for the most characteristic aromatic and olefin protons.

According to MS data, almost half of the final product (X) spontaneously formed pyroglutamyl derivative ($[M-17]^+$ ion).

In MALDI MS spectra of (X) peaks corresponding to unmodified peptide are present while the related peaks are absent in ESI-MS spectrum of the same substance. This is ascribed to facile fragmentation at the thiosuccinimide bond (retro-Michael reaction) under MALDI ionization conditions (destructive technique).

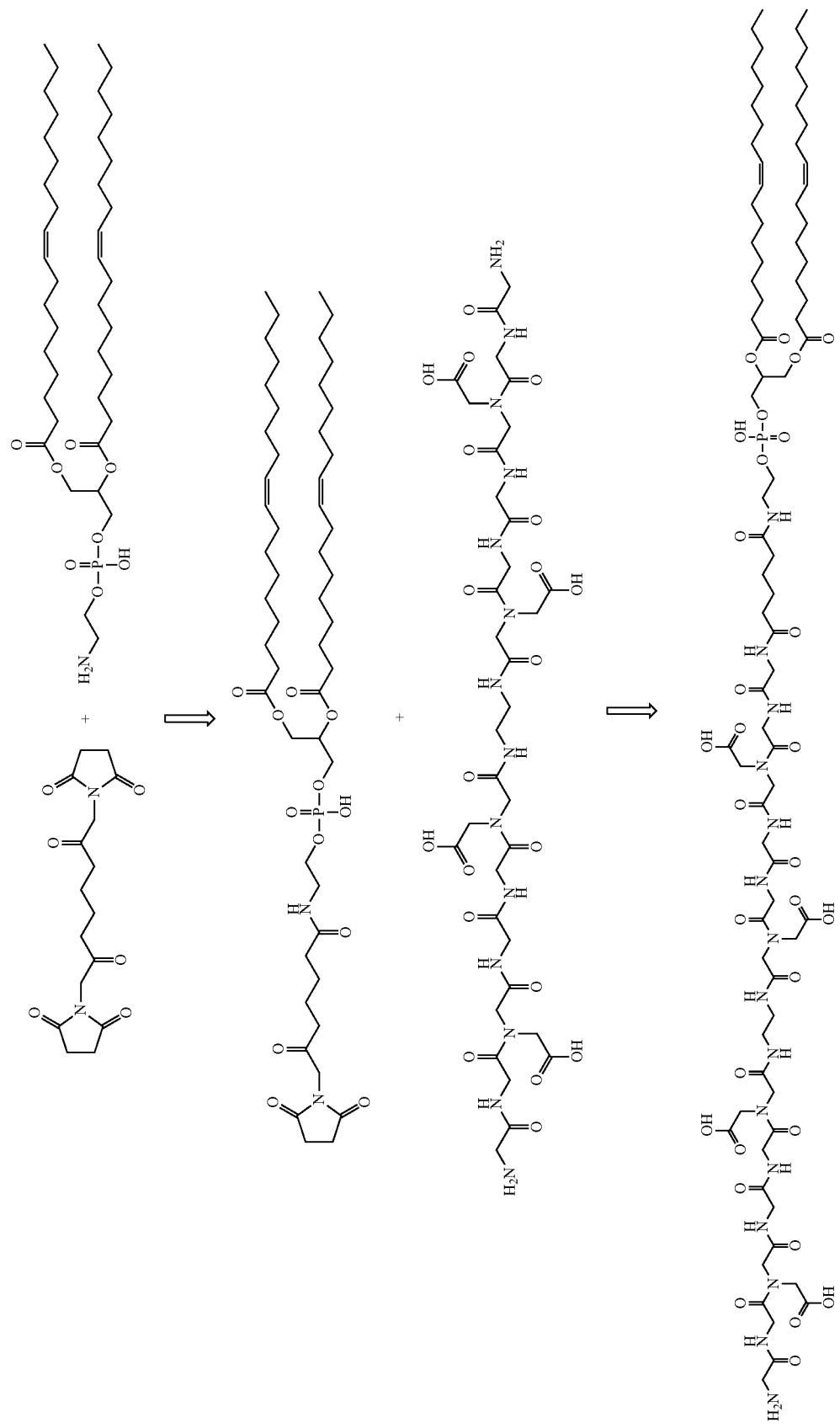

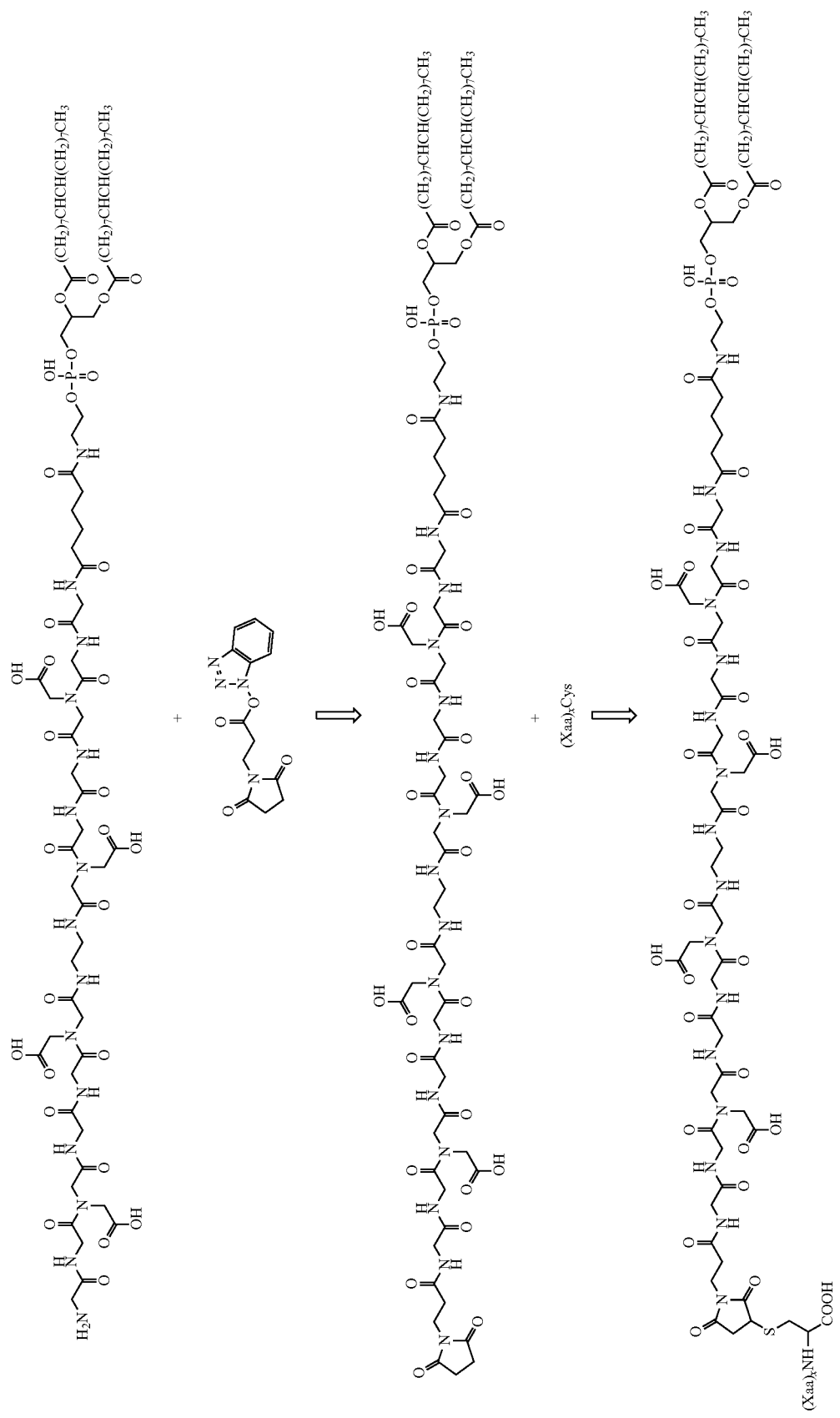

The general method of preparing peptide-lipid constructs was applied with minor modification to the preparation of constructs including peptides (F) selected from the following List of Peptides:

| List of Peptides | |
|---|---|
| Cys(Xaa)$_z$TrpThrProProArgAlaGlnIleThrGlyTyrLeuThrValGlyLeuThrArgArg | (SEQ ID NO: 19) |
| Cys(Xaa)$_z$TrpThrProProArgAlaGlnIleThrGlyTyrArgLeuThrValGlyLeuThrArgArg | (SEQ ID NO: 20) |
| Cys(Xaa)$_z$ValMetTyrAlaSerSerGly | (SEQ ID NO: 21) |
| Cys(Xaa)$_z$TyrProAlaHisThrAlaAsnGlu | (SEQ ID NO: 22) |
| ValMetTyrAlaSerSerGly(Xaa)$_z$Cys | (SEQ ID NO: 23) |
| AspTyrHisArgValMetTyrAlaSerSerGly(Xaa)$_z$Cys | (SEQ ID NO: 24) |
| ThrAsnGlyGluThrGlyGlnLeuValHisArgPhe(Xaa)$_z$Cys | (SEQ ID NO: 25) |
| ThrAsnGlyGluMetGlyGlnLeuValHisArgPhe(Xaa)$_z$Cys | (SEQ ID NO: 26) |
| AspThrTyrProAlaHisThrAlaAsnGluValSerGlu(Xaa)$_z$Cys | (SEQ ID NO: 27) |
| ThrTyrProAlaHisThrAlaAsnGluVal(Xaa)$_z$Cys | (SEQ ID NO: 28) |
| ProAlaHisThrAlaAsnGluVal(Xaa)$_z$Cys | (SEQ ID NO: 29) |
| TyrProAlaHisThrAlaAsnGlu(Xaa)$_z$Cys | (SEQ ID NO: 30) |
| ThrTyrProAlaHisThrAlaAsn(Xaa)$_z$Cys | (SEQ ID NO: 31) |
| ThrTyrProAlaHisThrAlaAsnGlu(Xaa)$_z$Cys | (SEQ ID NO: 32) |
| TyrProAlaHisThrAlaAsnGluVal(Xaa)$_z$Cys | (SEQ ID NO: 33) |
| TyrProAlaHisThrAlaAsnGlu(Xaa)$_z$Cys | (SEQ ID NO: 34) |
| ProAlaHisThrAlaAsnGluValSer(Xaa)$_z$Cys | (SEQ ID NO: 35) |
| AspThrTyrProAlaHisThrAlaAsnGlu(Xaa)$_z$Cys | (SEQ ID NO: 36) |
| TyrProAlaHisThrAlaAsnGluValSer(Xaa)$_z$Cys | (SEQ ID NO: 37) |
| SerGlnThrAsnAspLysHisLysArgAsp(Xaa)$_z$Cys | (SEQ ID NO: 38) |
| GlnThrAsnAspLysHisLysArgAspThrTyr(Xaa)$_z$Cys | (SEQ ID NO: 39) |
| GlnThrAsnAspLysHisLysArgAspThrTyrSerSerGlnThrAsnAspMetHisLysArgAspThrTyr(Xaa)$_z$Cys | (SEQ ID NO: 40) |
| GlnThrAsnAspMetHisLysArgAspThrTyr(Xaa)$_z$Cys | (SEQ ID NO: 41) |
| SerSerGlnThrAsnAspLysHisLysArg(Xaa)$_z$Cys | (SEQ ID NO: 42) |
| | (SEQ ID NO: 43) |

-continued

| List of Peptides |
|---|
| SerSerGlnThrAsnAspLysHisLysArgAspThrTyr(Xaa)$_z$Cys |
| (SEQ ID NO: 44) |
| SerSerGlnThrAsnAspMetHisLysArgAspThrTyr(Xaa)$_z$Cys |
| (SEQ ID NO: 45) |
| SerSerGlnThrAsnAspLysHisLysArgAspThrTyrSerSerGlnThrAsnAspMetHisLysArgAspThrTyr(Xaa)$_z$Cys |
| (SEQ ID NO: 46) |
| GlnThrAsnAspLysHisLysArgAspThr(Xaa)$_z$Cys |
| (SEQ ID NO: 47) |
| SerGlnThrAsnAspLysHisLysArgAspThr(Xaa)$_z$Cys |
| (SEQ ID NO: 48) |
| ThrAsnAspLysHisLysArgAspThrTyrPro(Xaa)$_z$Cys |
| (SEQ ID NO: 49) |
| GluGluThrGlyGluThrGlyGlnLeuVal(Xaa)$_z$Cys |
| (SEQ ID NO: 50) |
| GluGluGluThrGlyGluThrGlyGlnLeu(Xaa)$_z$Cys |
| (SEQ ID NO: 51) |
| GluThrGlyGluThrGlyGlnLeuValHis(Xaa)$_z$Cys |
| (SEQ ID NO: 52) |
| SerProProArgArgAlaArgValThr(Xaa)$_z$Cys |
| (SEQ ID NO: 53) |
| TyrArgTyrArgTyrThrProLysGluLysThrGlyProMetLysGlu(Xaa)$_z$Cys |
| (SEQ ID NO: 54) |
| TrpGlnProProArgAlaArgIle(Xaa)$_z$Cys |
| (SEQ ID NO: 55) |
| ThrIleThrGlyLeuGluProGlyThrGlu(Xaa)$_z$Cys |

Preparation of Functional Lipid Constructs (F-S-L) where F is a Glycan

Materials and General Methods

Acetone, benzene, chloroform, ethylacetate, methanol, o-xylene, toluene, and 2-propanol were from Khimed (Russian Federation). Acetonitrile was from Cryochrom (Russian Federation). DMSO, DMF, $CF_3COOH$, $Et_3N$, N,N'-dicyclohexylcarbodiimide and N-hydroxysuccinimide were from Merck (Germany). N-methylmorpholin (NMM), 2-maleimidopropionic acid and disuccimidilcarbonate were from Fluka. Iminodiacetic acid dimethyl ester hydrochloride was from Reakhim (Russian Federation). Molecular sieves (MS 3 Å and 4 Å), trimethylsilyl trifluoromethanesulfonate, and triphenylphosphine were from Aldrich (Germany). All hydrides, 1,8-diazabicyclo[5,4,0]undec-7-ene (DBU), and trichloroacetonitrile were from Merck (Germany).

Anhydrous tetrahydrofuran (THF) and diethyl ether ($Et_2O$) were obtained by distillation from lithium aluminium hydride ($H_4AlLi$). Dichloromethane for glycoside synthesis was dried by distillation from phosphorous pentoxide and calcium hydride and stored over molecular sieves MS 4 Å. Solid reagents were dried for 2 h in vacuo (0.1 mm Hg) at 20 to 40° C. Deacetylation was performed according to Zemplen in anhydrous methanol. The solution of the acetylated compound was treated with 2 M sodium methylate in methanol up to pH 9. When the reaction was completed, $Na^+$ ions were removed with cation exchange resin Dowex 50X-400 ($H^+$) (Acros, Belgium). The solution was concentrated in vacuo.

Column chromatography was carried out on Silica gel 60 (0.040-0.063 mm, Merck, Germany). Gel chromatography was performed on Sephadex LH-20 (Pharmacia, Sweden). Solvents were removed in vacuo at 30 to 40° C. Thin-layer chromatography was performed on Silica gel 60 (Merck, Germany) precoated plates. Spots were visualized by treating with 5% aqueous orthophosphoric acid and subsequent heating to 150° C. in the case of carbohydrates or by soaking in ninhydrin solution (3 g/l in 30:1 (v/v) butanol-acetic acid) in the case of amines.

Optical rotation was measured on a Jasco DIP-360 digital polarimeter at 25° C. Mass spectra were recorded on a Vision-2000 (Thermo Bioanalysis, UK) MALDI-TOF mass spectrometer using dihydroxybenzoic acid as a matrix. $^1H$ NMR spectra were recorded on a Bruker WM spectrometer (500 MHz) at 25° C. Chemical shifts (δ, ppm) were recorded relative to $D_2O$ (δ=4.750), $CDCl_3$ (δ=7.270), and $CD_3OD$ (δ=3.500) as internal standards. The values of coupling constants (Hz) are provided. The signals in the $^1H$ NMR spectra were assigned by suppression of spin-spin interaction (double resonance) and 2D-1H, 1H-COSY experiments.

Preparation of 3-aminopropyl 2-acetamido-2-deoxy-α-D-galactopyranosyl-(1→3)-β-D-galactopyranosyl-(1→4)-2-acetamido-2-deoxy-β-D-glucopyranoside (GalNAcα1-3Galβ1-4GlcNAc-$S_1$) (5)

The glycosyl chloride 3,4,6-tri-O-acetyl-2-azido-2-desoxy-β-D-galactopyranosylchloride (1) was prepared according to the method disclosed in the publication of Paulsen et al (1978). The glycosyl acceptor (3-trifluoroacetamidopropyl)-2-acetamido-3-O-acetyl-6-O-benzyl-2-deoxy-4-O-(2,4-di-O-acetyl-6-O-benzyl-β-D-galactopyranosyl)-β-D-glucopyranoside (2) was prepared according to the method disclosed in the publication of Pazynina et al (2008).

A solution of the glycosyl acceptor (420 mg, 0.5 mmol), silver triflate (257 mg, 1.0 mmol), tetramethylurea (120 μl, 1.0 mmol) and freshly calcinated molecular sieves 4 Å in dry dichloromethane (20 ml), were stirred at room temperature in darkness for 30 min. Another portion of sieves 4 Å was added, and a solution of glycosyl chloride (350 mg, 1.0 mmol) in dry dichloromethane (3 ml) was added. The mixture was stirred for 20 h at room temperature. The resin was filtered and washed with methanol (4×10 ml), then solvent was evaporated. Chromatography on silica gel (elution with 5-7% isopropanol in chloroform) yielded 407 mg (70%) of the product 3 as a mixture of anomers ($\alpha/\beta$=3.0 as determined by $^1$H-NMR spectroscopy).

A solution of the product 3 (407 mg, 0.352 mmol) in methanol (30 ml) was subjected to hydrogenolysis over 400 mg 10% Pd/C for 16 h. Then the resin was filtered off, washed with methanol (4×10 ml) and the product concentrated in vacuum. The dry residue was acetylated with 2:1 pyridine-acetic anhydride mixture (6 ml) at 20° C. for 16 h, the reagents being co-evaporated with toluene. Two chromatography steps on silica gel (elution with 10% isopropanol in ethyl acetate and with 5-10% methanol in chloroform) resulted in 160 mg (42%) of the product 4 and 39 mg (10%) of the product 4$\beta$.

A solution of 2 M sodium methylate in methanol (200 μl) was added to a solution of the product 4 (160 mg, 0.149 mmol) in dry methanol (4 ml). The solution was evaporated after 1 h, 4 ml water added and the solution kept for 16 h before being chromatographed on a Dowex-H' column (elution with 1 M ammonia). The eluate was evaporated, lyophilized to yield 87.2 mg (91%) of the 3-aminopropyltrisaccharide (5).

$^1$H NMR spectra were recorded on a Bruker BioSpin GmbH spectrometer at 303K. Chemical shifts ($\delta$) for characteristic protons are provided in ppm with the use of HOD (4.750), CHCl$_3$ ($\delta$ 7.270) as reference. Coupling constants (J) are provide in Hz. The signals in $^1$H NMR spectra were assigned using a technique of spin-spin decoupling (double resonance) and 2D-$^1$H,$^1$H-COSY experiments.

The values of optical rotation were measured on a digital polarimeter Perkin Elmer 341 at 25° C.

Mass spectra were registered on a MALDI-TOF Vision-2000 spectrometer using dihydroxybenzoic acid as a matrix.

4: $^1$H-NMR (700 MHz, CDCl$_3$): 1.759-1.834 (m, 1H, CH sp); 1.853-1.927 (m, 1H, CH sp); 1.972, 1.986, 1.996, 2.046, 2.053, 2.087, 2.106, 2.115, 2.130, 2.224 (10s, 10×3H, COCH$_3$); 3.222-3.276 (m, 1H, NCH sp); 3.544-3.583 (m, 1H, OCH sp); 3.591-3.661 (m, 2H, NCH sp, H-5a); 3.764 (dd≈t, 1H, H-4a, J 8.8); 3.787 (dd, 1H, H-3b, $J_{3,4}$ 3.7, $J_{2,3}$ 9.9); 3.836 (br. t, 1H, H-5b, J 7.3); 3.882-3.920 (m, 1H, OCH sp); 3.950 (dd, 1H, H-6'c, $J_{6',6''}$ 10.6, $J_{5,6'}$ 5.2); 4.009 (ddd, 1H, H-2a, $J_{1,2}$ 7.9, $J_{2,3}$ 10.0, $J_{2,NH}$ 9.0); 4.076-4.188 (m, 5H, H-6'a, H-6'b, H-6''b, H-5c, H-6''c); 4.415 (d, 1H, H-1a, $J_{1,2}$ 7.9); 4.443 (d, 1H, H-1b, $J_{1,2}$ 7.9); 4.529 (dd, 1H, H-6''a, $J_{6',6''}$ 12.0, $J_{5,6''}$ 2.5); 4.548 (ddd, 1H, H-2c, $J_{1,2}$ 3.4, $J_{2,3}$ 11.6, $J_{2,NH}$ 9.4); 4.893 (dd, 1H, H-3c, $J_{3,4}$ 3.1, $J_{2,3}$ 11.6); 5.021 (d, 1H, H-1c, $J_{1,2}$ 3.4); 5.039-5.075 (m, 2H, H-3a, H-2b); 5.339 (dd≈d, 1H, H-4b, J 2.9); 5.359 (dd, 1H, H-4c, $J_{3,4}$ 2.7, $J_{4,5}$ 0.9); 5.810 (d, 1H, NHAc a, $J_{2,NH}$ 9.0); 6.184 (d, 1H, NHAc c, $J_{2,NH}$ 9.4); 7.310-7.413 (m, 1H, NHCOCF$_3$ sp). $R_f$ 0.31 (EtOAc-iPrOH, 10:1). MS, m/z calculated for [C$_{43}$H$_{60}$N$_3$F$_3$O$_{25}$]H$^+$: 1076.35, found 1076.

4$\beta$: $^1$H-NMR (700 MHz, CDCl$_3$): 1.766-1.832 (m, 1H, CH sp); 1.850-1.908 (m, 1H, CH sp); 1.923, 1.969, 1.982, 2.059, 2.071, 2.099 (2), 2.120, 2.136, 2.148 (10s, 10×3H, COCH$_3$); 3.230-3.289 (m, 1H, NCH sp); 3.521 (ddd, 1H, H-2c, $J_{1,2}$ 8.2, $J_{2,3}$ 11.2, $J_{2,NH}$ 7.8); 3.548-3.591 (m, 1H, OCH sp); 3.591-3.648 (m, 2H, NCH sp, H-5a); 3.743 (dd≈t, 1H, H-4a, J 8.6); 3.795 (br. t, 1H, H-5b, J 6.5); 3.852 (dd, 1H, H-3b, $J_{3,4}$ 3.6, $J_{2,3}$ 9.9); 3.873-3.923 (m, 2H, H-5c, OCH sp); 4.002 (ddd, 1H, H-2a, $J_{1,2}$ 8.0, $J_{2,3}$ 9.5, $J_{2,NH}$ 8.9); 4.039 (dd, 1H, H-6'b, $J_{6',6''}$ 11.6, $J_{5,6'}$ 6.9); 4.087-4.144 (m, 3H, H-6'a, H-6''b, H-6'c); 4.160 (dd, 1H, H-6''c, $J_{6',6''}$ 11.2, $J_{5,6''}$ 6.0); 4.409, 4.417 (2d≈t, 2×1H, H-1a, H-1b, J 7.6); 4.519 (dd, 1H, H-6''a, $J_{6',6''}$ 11.8, $J_{5,6''}$ 2.5); 4.992 (d, 1H, H-1c, $J_{1,2}$ 8.2); 5.043 (dd, 1H, H-3a, $J_{3,4}$ 8.6, $J_{2,3}$ 9.5); 5.066 (dd, 1H, H-2b, $J_{1,2}$ 8.0, $J_{2,3}$ 9.8); 5.350 (dd≈d, 1H, H-4c, J 3.2); 5.372 (dd≈d, 1H, H-4b, J 3.4); 5.399 (d, 1H, NHAc c, $J_{2,NH}$ 7.8); 5.449 (dd, 1H, H-3c, $J_{3,4}$ 3.4, $J_{2,3}$

SCHEME V

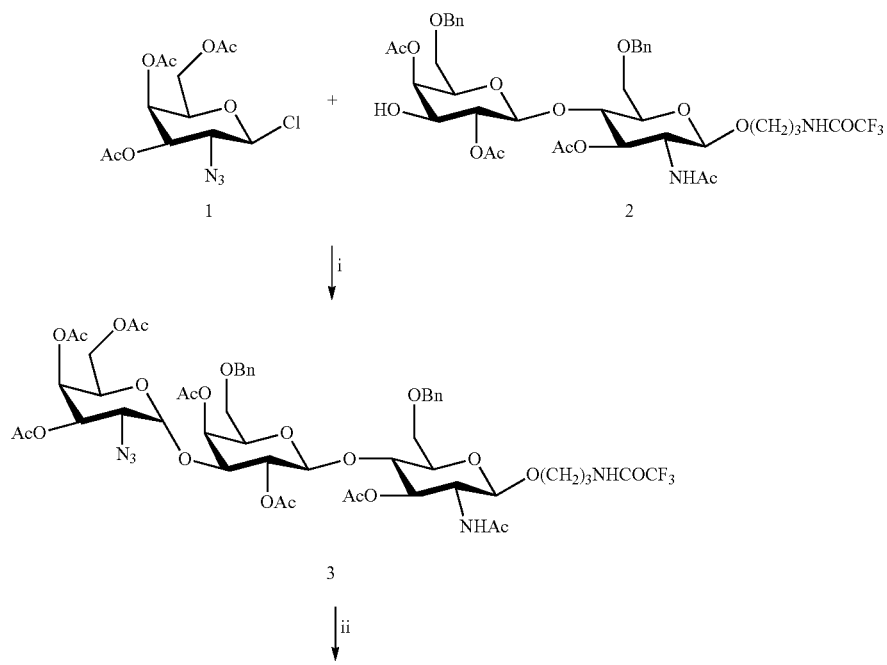

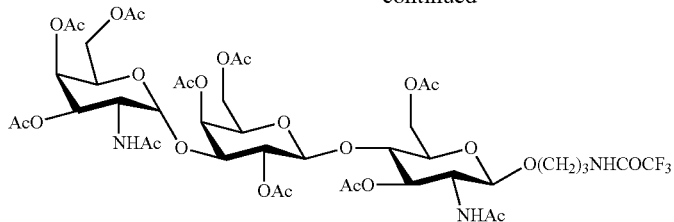

4

↓ iii

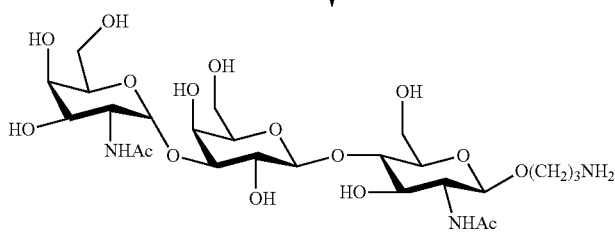

5

11.3); 5.856 (d, 1H, NHAc a, $J_{2,NH}$ 8.9); 7.361-7.466 (m, 1H, NHCOCF$_3$ sp). $R_f$ 0.24 (EtOAc-iPrOH, 10:1). MS, m/z calculated for [C$_{43}$H$_{60}$N$_3$F$_3$O$_{25}$]H$^+$: 1076.35, found 1076.

5: $^1$H-NMR (700 MHz, D$_2$O): 1.924-2.002 (m, 2H, CH$_2$ sp); 2.060, 2.064 (2s, 2×3H, NCOCH$_3$); 3.102 (m≈t, 2H, NCH$_2$ sp, J 6.8); 3.592-3.644 (m, 1H, H-5a); 3.655 (dd, 1H, H-2b, $J_{1,2}$ 7.9, $J_{2,3}$ 9.9); 3.702 (br. dd, 1H, H-5b, $J_{5,6'}$ 3.8, $J_{5,6''}$ 8.2, $J_{4,5}$≤1); 3.713-3.815 (m, 9H); 3.846 (dd, 1H, H-6'a, $J_{6',6''}$ 12.3, $J_{5,6'}$ 5.3); 3.984-4.062 (m, 4H, OCH sp, H-6''a, H-4b, H-3c); 4.123 (dd≈d, 1H, H-4c, J 2.9); 4.206 (br. t, 1H, H-5c, J 6.3); 4.248 (dd, 1H, H-2c, $J_{1,2}$ 3.6, $J_{2,3}$ 11.0); 4.542 (2d≈t, 2H, H-1a, H-1b, J 7.4); 5.100 (d, 1H, H-1c, $J_{1,2}$ 3.5). $R_f$ 0.55 (MeOH-1M aq. Py.AcOH, 5:1). MS, m/z calculated for [C$_{25}$H$_{45}$N$_3$O$_{16}$]H$^+$: 644.28; found 644. [α]$_{546\ nm}$+128 (c 0.3; MeCN-H$_2$O, 1:1).

5β: $^1$H-NMR (700 MHz, D$_2$O): 1.938-1.991 (m, 2H, CH$_2$ sp); 2.055, 2.062 (2s, 2×3H, NCOCH$_3$); 3.100 (m≈t, 2H, NCH$_2$ sp, J 6.9); 3.610 (dd, 1H, H-2b, $J_{1,2}$ 7.9, $J_{2,3}$ 9.9); 3.603-3.636 (m, 1H, H-5a); 3.682 (br. dd, 1H, H-5b, $J_{5,6'}$ 4.9, $J_{5,6''}$ 7.8, $J_{4,5}$≤1); 3.693-3.826 (m, 11H); 3.842 (dd, 1H, H-6'a, $J_{6',6''}$ 12.1, $J_{5,6'}$ 5.2); 3.934-3.972 (m, 2H, H-4b, H-2c); 4.012 (dd, 1H, H-6''a, $J_{6',6''}$ 12.2, $J_{5,6''}$ 2.0); 4.023-4.057 (m, 1H, OCH sp); 4.175 (dd≈d, 1H, H-4c, J 2.9); 4.478 (d, 1H, H-1b, $J_{1,2}$ 7.9); 4.531 (d, 1H, H-1a, $J_{1,2}$ 8.1); 4.638 (d, 1H, H-1c, $J_{1,2}$ 8.4). $R_f$ 0.48 (MeOH-1M aq. Py.AcOH, 5:1). MS, m/z calculated for [C$_{25}$H$_{45}$N$_3$O$_{16}$]H$^+$: 644.28; found 644. [α]$_{546\ nm}$+6 (c 0.3; MeCN—H$_2$O, 1:1).

Preparation of 3-aminopropyl-α-D-galactopyranosyl-(1→3)-β-D-galactopyranosyl-(1→4)-2-acetamido-2-deoxy-β-D-glucopyranoside (Galα1-3Galβ1-4GlaNAc-S$_1$; Galili) (9)

A mixture of the glycosyl acceptor 2 (500 mg, 0.59 mmol), thiogalactopyranoside 6 (576 mg, 1.18 mmol), NIS (267 mg, 1.18 mmol), anhydrous CH$_2$Cl$_2$ (25 ml) and molecular sieves 4 Å (500 mg) was stirred at −45° C. for 30 min under an atmosphere of Ar. A solution of TfOH (21 μl, 0.236 mmol) in anhydrous CH$_2$Cl$_2$ (0.5 ml) was then added. The reaction mixture was stirred for 2 h at −45° C. and the temperature was then increased to −20° C. over 4 h. The mixture was kept at −20° C. overnight. Then extra amounts of thiogalactopyranoside 6 (144 mg, 0.295 mmol), NIS (66 mg, 0.295 mmol) and TfOH (5 μl, 0.06 mmol) were added and the stirring maintained at −20° C. for 2 h before being allowed to slowly warm up to r.t. (1 h). A saturated aqueous solution of Na$_2$S$_2$O$_3$ was then added and the mixture filtered. The filtrate was diluted with CHCl$_3$ (300 ml), washed with H$_2$O (2×100 ml), dried by filtration through cotton wool, and concentrated. Gel filtration on LH-20 (CHCl$_3$-MeOH) afforded the product 3-trifluoroacetamidopropyl-3,4-di-O-acetyl-2,6-di-O-benzyl-α-D-galactopyranosyl-(1-3)-2,4-di-O-acetyl-6-O-benzyl-β-D-galactopyranosyl-(1-4)-2-acetamido-3-O-acetyl-6-O-benzyl-2-deoxy-β-D-glucopyranoside (7) (600 mg, 80%), as a white foam.

$^1$H NMR (700 MHz, CDCl$_3$, characteristic signals), δ, ppm: 1.78-1.82 (m, 4H, CHCHC, OC(O)CH$_3$), 1.84-1.90 (m, 1H, CHCHC), 1.91, 1.94, 1.97, 1.98, 2.06 (5 s, 5×3H, 4 OC(O)CH$_3$, NH(O)CH$_3$), 3.23-3.30 (m, 1H, NCHH), 3.59-3.65 (m, 1H, NCHH), 4.05 (m, 1H, H-2$^I$), 4.33 (d, 1H, $J_{1,2}$ 7.55, H-1$^I$), 4.40 (d, 1H, J 12.04, PhCHH), 4.42 (d, 1H, $J_{1,2}$ 8.07, H-1$^{II}$), 4.45 (d, 1H, J 11.92, PhCHH), 4.48 (d, 1H, J 12.00, PhCHH), 4.50 (d, 1H, J 12.00, PhCHH), 4.52 (d, 1H, J 12.04, PhCHH), 4.54 (d, 1H, J 12.00, PhCHH), 4.57 (d, 1H, J 12.00, PhCHH), 4.64 (d, 1H, J 11.92, PhCHH), 4.99 (dd≈t, 1H, J 8.24, H-2$^{II}$), 5.08-5.13 (m, 2H, H-3$^I$, H-3$^{III}$), 5.23 (d, 1H, $J_{1,2}$ 3.31, H-1$^{III}$), 5.46 (d, 1H, $J_{3,4}$ 2.25, H-4$^{II}$), 5.54 (d, 1H, $J_{3,4}$ 3.11, H-4$^{III}$), 7.20-7.40 (m, 20H, ArH); 7.49-7.54 (m, 1H, NHC(O)CF$_3$). $R_f$ 0.4 (PhCH$_3$—AcOEt, 1:2).

The product 7 (252 mg, 0.198 mmol) was deacetylated according to Zemplen (8 h, 40° C.), neutralized with AcOH and concentrated. The TLC (CH$_3$Cl-MeOH, 10:1) analysis of the obtained product showed two spots: the main spot with $R_f$ 0.45, and another one on the start line (ninhydrin positive spot) that was an indication of partial loss of trifluoroacetyl. Therefore, the product was N-trifluoroacetylated by treatment with CF$_3$COOMe (0.1 ml) and Et$_3$N (0.01 ml) in MeOH (10 ml) for 1 h, concentrated and subjected to column chromatography on silica gel (CHCl$_3$-MeOH, 15:1) to afford the product 8 as a white foam (163 mg, 77%), $R_f$ 0.45 (CH$_3$Cl-MeOH, 10:1). The product 8 was subjected to hydrogenolysis (200 mg Pd/C, 10 ml MeOH, 2 h), filtered, N-defluoroacetylated (5% Et₃N/H₂O, 3 h) and concentrated. Cation-exchange chromatography on Dowex 50×4-400 (H⁺) (elution with 5% aqueous ammonia) gave the product 9 (90 mg, 98%) as a white foam.

¹H NMR (D₂O, characteristic signals), δ, ppm: 1.94-1.98 (m, 2H, CCH₂C), 2.07 (s, 3H, NHC(O)CH₃), 3.11 (m, J 6.92, 2H, NCH₂), 4.54 and 4.56 (2d, 2H, $J_{1,2}$ 8.06, $J_{1,2}$ 7.87, H-1$^I$ and H-1$^{II}$), 5.16 (d, 1H, $J_{1,2}$ 3.87, H-1$^{III}$). $R_f$ 0.3 (EtOH—BuOH—Py-H₂O—AcOH; 100:10:10:10:3).

(21) and 2-aminoethyl α-D-galactopyranosyl-(1→4)-β-D-galactopyranosyl-(1→4)-β-D-glucopyranoside (28) (Galα1-4Galβ1-4Glc-S₁; Gb₃-S₁)

The title primary aminoalkyl variants of Gb₃-S₁ were prepared according SCHEME VII, SCHEME VIII and SCHEME IX.

Preparation of (2,3,4,6-tetra-O-acetyl-β-D-galactopyranosyl)-(1→4)-2,3,6-tri-O-acetyl-α-D-glucopyranosyl trichloroacetimidate (10)

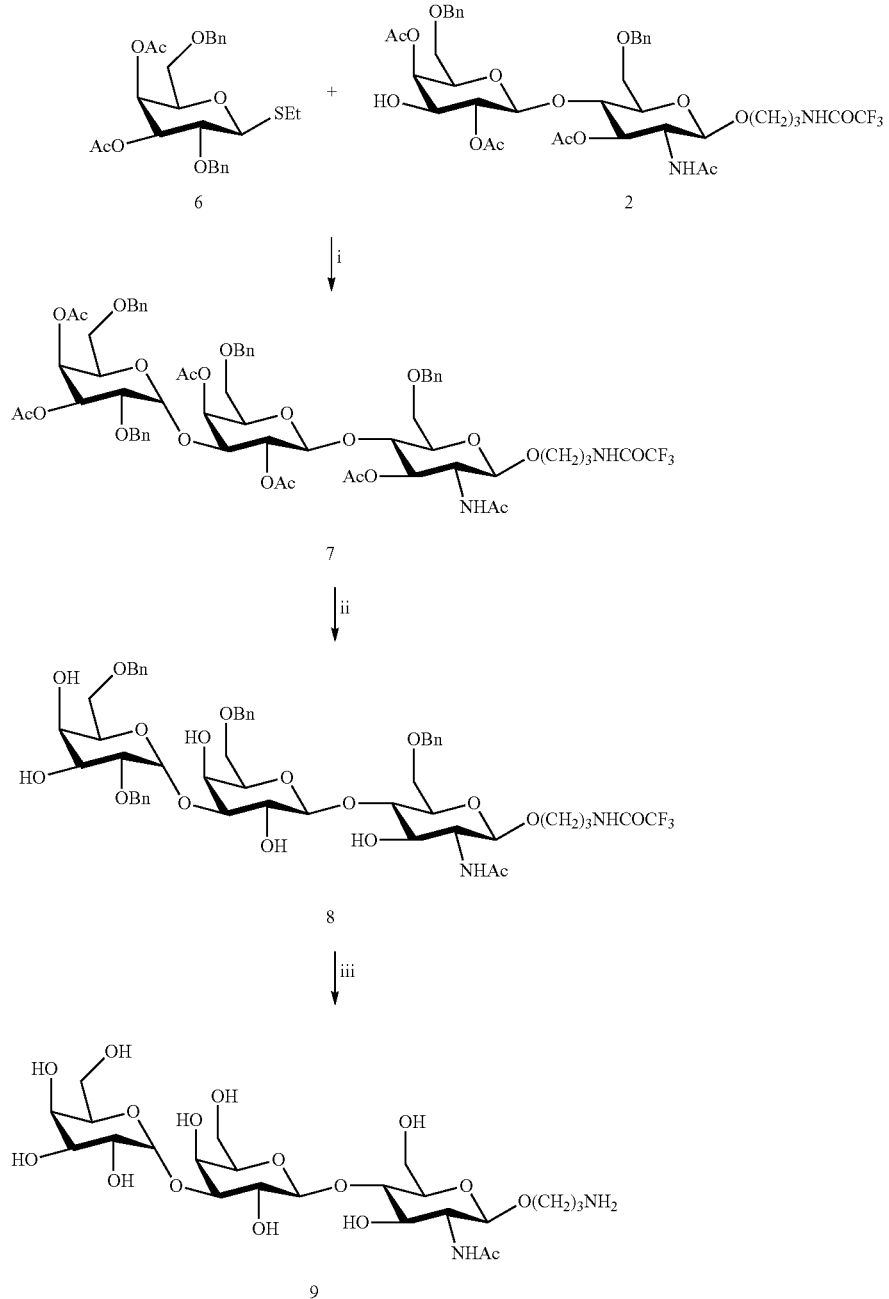

SCHEME VI

Preparation of 3-aminopropyl α-D-galactopyranosyl-(1→4)-β-D-galactopyranosyl-(1→4)-β-D-glucopyranoside Trichloroacetonitrile (12.1 ml, 121 mmol) and DBU (0.45 ml, 3 mmol) were added to a solution of 10a (7.68 g, 12.1 mmol) in dry dichloromethane (150 ml) at −5° C. The reaction mixture was stirred at −5° C. for 3.5 h and concentrated in vacuo.

Flash chromatography (2:1 to 1:2 (0.1% Et$_3$N) toluene-ethyl acetate) of the residue provided 10 (6.01 g, 63.9%) as a light yellow foam, R$_f$ 0.55 (2:1 toluene-acetone).

$^1$H NMR, CDCl$_3$: 1.95-2.2 (7s, 21H, 7Ac), 4.49 (d, 1H, J$_{1,2}$=8.07, H-1b), 4.91 (dd, 1H, J$_{3,2}$=10.3, J$_{3,4}$=2.8, H-3b), 5.05 (dd, 1H, J$_{2,1}$=3.5, J$_{2,3}$=9.3, H-2a), 5.12 (dd, 1H, J$_{2,1}$=8.07, J$_{2,3}$=10.3, H-2b), 5.32 (d, 1H, J$_{4,3}$=3, J$_{4,5}$<1, H-4b), 5.52 (t, 1H, J$_{3,2}$=J$_{3,4}$=9.29, H-3a), 6.48 (d, 1H, J$_{1,2}$=3.5, H-1a), 8.64 (s, 1H, HN=CCl$_3$).

Preparation of 3-chloropropyl-(2,3,4,6-tetra-O-acetyl-β-D-galactopyranosyl)-(1→4)-2,3,6-tri-O-acetyl-β-D-glucopyranoside (11)

A mixture of 2.94 g (3.8 mmol) of trichloroacetimidate 10, 0.66 ml (7.5 mmol) 3-chloropropanol, 50 ml dichloromethane, and 3 g of molecular sieves MS 4 Å was cooled to −5° C. An 8% solution of BF$_3$.Et$_2$O (0.4 mmol) in anhydrous dichloromethane was added drop wise with stirring.

After 30 min, the reaction mixture was filtered, diluted with chloroform (500 ml), and washed with water, saturated sodium hydrocarbonate solution, and water to pH 7. The washed reaction mixture was dried by filtration through a cotton layer and concentrated in vacuo.

Column chromatography on Silica gel (elution with 2.5:1 (v/v) toluene-ethyl acetate) resulted in 1.75 g (65%) of lactose derivative (11) as white foam. R$_f$ 0.54 (2:1 toluene-acetone), R$_f$ 0.50 (4:2:1 hexane-chloroform-isopropanol), [α]$_D$−4° (c 1.0, CHCl$_3$), m/z 712.2 (M$^+$).

$^1$H NMR, CDCl$_3$: 1.95 (br. s, 5H, Ac, —CH$_2$—), 2.0-2.2 (6s, 18H, 6Ac), 3.52 (m, 2H, —CH$_2$Cl), 3.63 (m, 1H, H-5a), 3.68 (m, 1H, OCHH—), 3.79 (t, 1H, J=9.3, H-4a), 3.88 (m, 1H, H-5b), 3.93-3.98 (m, 1H, OCHH—), 4.05-4.15 (m, 3H, H-6a', H-6b, H-6b'), 4.45 (d, 2H, H-1a, H-1b, J$_{2,1}$=7.83) 4.47 (m, 1H, H-6a), 4.89 (dd, 1H, J$_{2,3}$=9.3, J$_{2,1}$=7.82, H-2a), 4.96 (dd, 1H, J$_{3,2}$=10.5, J$_{3,4}$=3.42, H-3b), 5.11 (dd, 1H, J$_{2,3}$=10.5, J$_{2,1}$=7.83, H-2b), 5.21 (t, 1H, J=9.3, H-3a), 5.35 (dd, 1H, J$_{4,3}$=3.42, J$_{4,5}$<1).

Preparation of 3-azidopropyl (2,3,4,6-tetra-O-acetyl-β-D-galactopyranosyl)-(1→4)-2,3,6-tri-O-acetyl-β-D-glucopyranoside (12)

A mixture of 2.15 g (3 mmol) of trichloropropylglycoside 11, 0.59 g (9 mmol) NaN$_3$, and 30 ml DMSO was maintained at 80° C. with stirring for 20 h. The mixture was then diluted with chloroform (500 ml), washed with water (4×100 ml), dried by filtration through a cotton layer, and concentrated in vacuo.

Column chromatography on Silica gel (elution with 8:2:1 hexane-chloroform-isopropanol) resulted in 1.96 g (91%) of glycoside (12) as a white foam, R$_f$ 0.54 (2:1 (v/v) toluene-acetone), R$_f$ 0.50 (4:2:1 (v/v/v) hexane-chloroform-isopropanol), [α]$_D$−5.4° (c 1.0, CHCl$_3$), m/z 718.8 (M$^+$).

$^1$H NMR, CDCl$_3$: 1.85 (m, 2H, —CH$_2$—), 1.98-2.2 (7s, 21H, 7Ac), 3.36 (m, 2H, —CH$_2$N$_3$), 3.61 (m, 2H, H-5a, OCHH—CH$_2$—), 3.8 (t, 1H, J$_{3,4}$=J$_{4,5}$=9.29, H-4a), 3.85-3.94 (m, 2H, OCHH—CH$_2$; H-5b), 4.05-4.17 (m, 3H, H-6a, H-6a', H-6b), 4.49 (d, 1H, J$_{1,2}$=8.07, H-1a), 4.5 (m, 1H, H-6b'), 4.51 (d, 1H, J$_{1,2}$=8.07, H-1b), 4.9 (dd, 1H, J$_{2,1}$=8.07, J$_{2,3}$=9.29, H-2a), 4.97 (dd, 1H, J$_{3,2}$=10.27, J$_{3,4}$=3, H-3b), 5.12 (dd, 1H, J$_{2,1}$=8.07, J$_{2,3}$=10.27, H-2b), 5.2 (t, 1H, J$_{3,2}$=J$_{3,4}$=9.29, H-3a), 5.36 (dd, 1H, J$_{4,3}$=3, J$_{4,5}$<1).

Preparation of 3-azidopropyl (4,6-O-benzylidene-β-D-galactopyranosyl)-(1→4)-β-D-glucopyranoside (13)

The lactoside 12 (1.74 g, 2.4 mmol) was deacetylated according to Zemplen and co-evaporated with toluene (2×30 ml). The residue was treated with α,α-dimethoxytoluene (0.65 ml, 3.6 mmol) and p-toluenesulfonic acid (50 mg, to pH 3) in DMF (20 ml) for 3 h. The reaction mixture was then quenched with pyridine, concentrated, and co-evaporated with o-xylene.

Column chromatography on Silica gel (elution with 9:1 (v/v) chloroform-isopropanol) and recrystalization (chloroform-methanol) resulted in 0.756 mg (62%) of benzylidene derivative (13). R$_f$ 0.6 (5:1 chloroform-isopropanol), [α]$_D$−25.7° (c 1.0, methanol), m/z 513.4 (M$^+$).

$^1$H NMR, CD$_3$OD: 2.06 (m, 2H, —CH$_2$—), 3.45 (dd, 1H, J$_{2,1}$=J$_{2,3}$=9, H-2a), 3.61 (m, 1H, H-5a), 3.64 (m, 2H, —CH$_2$N$_3$), 3.74-3.9 (m, 6H, OCHH—; H-3a, H-4a; H-2b, H-3b, H-5b), 4.08-4.18 (m, 3H, H-6, H-6a', OCHH—), 4.34-4.44 (m, 3H, H-6b, H-6b', H-4b), 4.5 (d, 1H, J$_{1,2}$=7.9, H-1a), 4.68 (d, 1H, J$_{1,2}$=8, H-1b), 5.82 (s, 1H, CHPh), 7.55-7.72 (m, 5H, CHPh).

Preparation of 3-azidopropyl (4,6-O-benzylidene-3-O-benzyl-β-D-galactopyranosyl)-(1→4)-2,3,6-tri-O-benzyl-β-D-glucopyranoside (14)

Sodium hydride in mineral oil (290 mg, 12 mmol) was slowly added in 4 to 5 portions to a solution of 13 (726 mg, 1.5 mmol) in DMF (15 ml) at 0° C. with stirring. After 1 h, the ice bath was removed and benzyl bromide was added drop wise. The mixture was stirred overnight. 10 ml of methanol was then added. After 1 h, the mixture was diluted with chloroform (500 ml), and washed with water (3×200 ml), dried by filtration through a cotton layer, concentrated, and co-evaporated in vacuo with o-xylene.

Column chromatography on Silica gel (elution with 10:1 toluene-ethyl acetate) resulted in 1.24 g (87%) of lactose derivative 14 as white foam, R$_f$ 0.56 (5:3 (v/v) hexane-ethyl acetate), [α]$_D$+10.8° (c 1.0, CHCl$_3$), m/z 963.8 (M$^+$).

$^1$H NMR, CDCl$_3$: 1.85 (m, 2H, —CH$_2$—), 2.91 (m, 1H, H-5b), 3.33 (m, 1H, H-5a), 3.34-3.42 (m, 4H, H-2a, H-3b, —CH$_2$N$_3$), 3.55-3.62 (m, 2H, OCHH—; H-3a), 3.73 (dd, 1H, J$_{2,1}$=8, J$_{2,3}$=10, H-2b), 3.92-3.97 (m, 2H, H-4a, OCH H—), 4.0 (br. d, 1H, J$_{4,3}$=3.6, H-4b), 4.34 (d, 1H, J$_{1,2}$=7.9, H-1a), 4.42 (d, 1H, J$_{1,2}$=8, H-1b), 5.43 (s, 1H, CH(Bd), 7.14-7.50 (m, 30H, Ph).

Preparation of 3-azidopropyl (2,3,6-O-tri-O-benzyl-β-D-galactopyranosyl)-(1→4)-2,3,6-tri-O-benzyl-β-D-glucopyranoside (15)

Hydrogen chloride in diethyl ether was added to a mixture of 14 (1.24 g, 1.3 mmol), sodium cyanoborohydride (0.57 g, 9.1 mmol), and freshly activated molecular sieves MS 3 Å (33 g) in anhydrous THF (20 ml) until the evolution of gas ceased.

The mixture was stirred for 2 h, diluted with chloroform (300 ml), washed with water, saturated sodium hydrocarbonate solution, and water to pH 7. The washed mixture was dried by filtration through a cotton layer and concentrated in vacuo.

Column chromatography on Silica gel (elution with 20:1 to 7:3 (v/v) toluene-ethyl acetate) resulted in 0.91 g (65%)

of lactose derivative 15 as a white foam, $R_f$ 0.42 (9:1 (v/v) toluene-acetone), $[\alpha]_D$+17.8° (c 1.0, CHCl$_3$), m/z 965.8 (M$^r$).

$^1$H NMR, CDCl$_3$: 1.85 (m, 2H, —CH$_2$—), 2.39 (d, 1H, J=2.2, OH), 4.04 (br. s, 1H, H-4b), 4.34 (d, 1H, J$_{1,2}$=7.9, H-1a), 4.42 (d, 1H, J$_{1,2}$=8, H-1b), 7.14-7.50 (m, 30H, Ph).

$^1$H NMR of acetylated analytical probe 15a, CDCl$_3$: 1.85 (m, 2H, —CH$_2$—), 4.34 (d, 1H, J$_{1,2}$=7.9, H-1a), 4.42 (d, 1H, J$_{1,2}$=8, H-1b), 5.5 (br. d, 1H, J$_{4,3}$=3.43, H-4b), 7.14-7.50 (m, 30H, Ph).

Preparation of 3-trifluoroacetamidopropyl (2,3,6-O-tri-O-benzyl-β-D-galactopyranosyl)-(1→4)-2,3,6-tri-O-benzyl-β-D-glucopyranoside (16)

A mixture of derivative 15 (0.914 g, 0.94 mmol), triphenylphosphine (0.5 g, 1.9 mmol) and THF (10 ml) was stirred for 0.5 h, 100 µl of water added, and the mixture stirred overnight. The reaction mixture was then concentrated and co-evaporated with methanol. The residue was dissolved in methanol (15 ml) and triethylamine (30 µl) and methyl trifluoroacetate (0.48 ml, 4.7 mmol) added. The solution was held for 30 min and then concentrated.

Column chromatography on Silica gel (elution with 5:1 to 1:1 (v/v) hexane-acetone) resulted in 0.87 g (84%) of lactose derivative 16 as white foam, $R_f$ 0.49 (9:1 (v/v) hexane-acetone), $[\alpha]_D$+17° (c 1.0, CHCl$_3$), m/z 1060.1 (M$^+$+Na).

$^1$H NMR, CDCl$_3$: 1.88 (m, 2H, —CH$_2$—), 2.40 (br. s, 1H, OH), 4.05 (br. s, 1H, H-4b), 4.36 (d, 1H, J$_{1,2}$=7.8, H-1a), 4.40 (d, 1H, J$_{1,2}$=7.6, H-1b), 7.10-7.35 (m, 30H, Ph).

Preparation of 2,3,4,6-tetra-O-benzyl-β-D-galactopyranosyl trichloroacetimidate (18)

A mixture of galactose derivative 17 (2 g, 3.65 mmol), trichloroacetonitrile (1.75 ml, 17.55 mmol), anhydrous potassium carbonate (2 g, 14.6 mmol), and dichloromethane (4 ml) was stirred for 22 h at room temperature under argon. The mixture was then filtered through a Celite layer and concentrated in vacuo. Column chromatography on Silica gel (elution with 4:1 (v/v) hexane-ethyl acetate (1% Et$_3$N) resulted in 1.5 g (60%) of 18 as white foam, $R_f$ 0.47 (7:3 (v/v) hexane-ethyl acetate containing 1% Et$_3$N) and 0.46 g (0.8 mmol, 23%) of the starting derivative 17, $R_f$ 0.27 (7:3 (v/v) hexane-ethyl acetate containing 1% Et$_3$N).

$^1$H NMR (CDCl$_3$): 3.60-3.70 (m, 3H, H-3, H-6, H-6'), 3.75 (t, 1H, J$_{5,6}$=6.30, H-5), 3.98 (d, 1H, J$_{4,3}$=2.19, H-4), 4.08 (dd, 1H, J$_{2,3}$=9.73, J$_{2,1}$=7.95, H-2), 4.42 and 4.47 (ABq, 2H, J=12.00, PhCH$_2$), 4.63 and 4.95 (ABq, 2H, J=11.51, PhCH$_2$), 4.72 (s, 2H, PhCH$_2$), 4.80 and 4.90 (ABq, 2H, J=10.95, PhCH$_2$), 5.74 (d, 1H, J$_{1,2}$=7.95, H-1), 7.22-7.35 (m, 20H, ArH), 8.62 (s, 1H, NH).

Preparation of 3-trifluoroacetamidopropyl (2,3,4,6-tetra-O-benzyl-α-D-galactopyranosyl)-(1→4)-(2,3,6-tri-O-benzyl-β-D-galactopyranosyl)-(1→4)-2,3,6-tri-O-benzyl-β-D-glucopyranoside (19)

A mixture of lactose derivative 16 (158 mg, 0.153 mmol), trichloroacetimidate 18 (120 mg, 0.175 mmol), molecular sieves MS 4 Å (0.5 g), and dichloromethane (5 ml) was stirred for 30 min at room temperature under argon. 0.1 ml of a 1% (v/v) solution of trimethylsilyl trifluoromethanesulfonate in dichloromethane was then added. After 2 h, another 50 mg (0.073 mmol) trichloroacetimidate 18 and 30 µl of a 1% (v/v) solution of trimethylsilyl trifluoromethanesulfonate in dichloromethane were added. The reaction mixture was stirred overnight at +4° C., quenched with triethylamine (5 µl), filtered, and concentrated in vacuo.

Column chromatography on Silica gel (elution with 12:1 to 1:1 (v/v) toluene-ethyl acetate) resulted in 170 mg (72%) of trisaccharide 19; $R_f$ 0.56 (4:1 (v/v) toluene-ethyl acetate); $[\alpha]_D$+30.8° (c 1.0, CHCl$_3$).

$^1$H NMR, CDCl$_3$: 1.78-1.89 (m, 2H, —CH$_2$—), 4.34 (d, 1H, J$_{1,2}$=7.8, H-1a), 4.43 (d, 1H, J$_{1,2}$=7.4, H-1b), 5.06 (d, 1H, J$_{1,2}$=3.0, H-1c), 7.14-7.48 (m, 50H, Ph).

Preparation of 3-trifluoroacetamidopropyl (2,3,4,6-tetra-O-acetyl-α-D-galactopyranosyl)-(1→4)-(2,3,6-tri-O-acetyl-β-D-galactopyranosyl)-(1→4)-2,3,6-tri-O-acetyl-β-D-glucopyranoside (20)

The catalyst 10% Pd/C (10 mg) was added to a solution of the protected oligosaccharide 19 (73 mg, 0.047 mmol) in methanol (7 ml), the mixture degassed, and the flask filled with hydrogen. The reaction mixture was stirred for 1 h, filtered off from the catalyst through a Celite layer, and concentrated in vacuo. The dry residue was dissolved in pyridine (2 ml), acetic anhydride (1 ml) added, and the mixture held for 3 h. The solvents were then evaporated and residue co-evaporated with toluene (4×2 ml).

Column chromatography on Silica gel (elution with 2:1 hexane-acetone) resulted in 43.5 mg (90%) of trisaccharide 20 as a white foam, $R_f$ 0.52 (2:1 hexane-acetone), $[\alpha]_D$+30.4° (c 1.0, CHCl$_3$).

$^1$H NMR, CDCl$_3$: 1.87 (2H, m, CH$_2$); 1.99, 2.05, 2.05, 2.06, 2.07, 2.07, 2.09, 2.09, 2.12, and 2.14 (10×3H, 10 s, 10 Ac); 3.37 and 3.52 (2×1H, 2 m, 2 CHN); 3.63 (1H, ddd, J$_{4,5}$=9.8, J$_{5,6}$=4.9, J$_{5,6'}$=2.0, H-5a); 3.72 (1H, m, OCH); 3.77 (1H, ddd≈br. T, J$_{4,5}$<1, J$_{5,6}$=6.8, J$_{5,6'}$=6.1, H-5b); 3.79 (1H, dd, J$_{3,4}$=9.3, J$_{4,5}$=9.8, H-4a); 3.87 (1H, m, OCH); 4.02 (1H, dd≈br. d, J$_{3,4}$=2.5, J$_{4,5}$<1, H-4b); 4.09 (1H, dd, J$_{5,6}$=4.9, J$_{6,6'}$=12.0, H-6a); 4.12 (1H, dd, J$_{5,6}$=5.6, J$_{6,6'}$=10.8, H-6c); 4.14 (1H, dd, J$_{5,6}$=6.8, J$_{6,6'}$=11.0, H-6b); 4.17 (1H, dd, J$_{5,6'}$=8.6, J$_{6,6'}$=10.8, H-6'c); 4.45 (1H, dd, J$_{5,6'}$=6.1, J$_{6,6'}$=11.0, H-6'b); 4.49 (1H, ddd□br. T, J$_{4,5}$<1, J$_{5,6}$=5.6, J$_{5,6'}$=8.6, H-5c); 4.50 (1H, d, J$_{1,2}$=7.8, H-1a); 4.55 (1H, d, J$_{1,2}$=7.8, H-1b); 4.59 (1H, dd, J$_{5,6'}$=2.0, J$_{6,6'}$=12.0, H-6'a); 4.76 (1H, dd, J$_{2,3}$=10.8, J$_{3,4}$=2.5, H-3b); 4.86 (1H, dd, J$_{1,2}$=8.1, J$_{2,3}$=9.5, H-2a); 4.10 (1H, d, J$_{1,2}$=3.4, H-1c); 5.12 (1H, dd, J$_{1,2}$=7.8, J$_{2,3}$=10.8, H-2b); 5.19 (1H, dd, J$_{1,2}$=3.4, J$_{2,3}$=11.0, H-2c); 5.22 (1H, dd≈T, J$_{2,3}$=9.5, J$_{3,4}$=9.3, H-3a); 5.40 (1H, dd, J$_{2,3}$=11.0, J$_{3,4}$=3.4, H-3c); 5.59 (1H, dd≈br. d, J$_{3,4}$=3.4, J$_{4,5}$<1, H-4c); 7.09 (1H, m, NHCOCF3).

Preparation of 3-aminopropyl α-D-galactopyranosyl-(1→4)-β-D-galactopyranosyl-(1→4)-β-D-glucopyranoside (Gb$_3$-sp3) (21)

Sodium methylate (30 µl of 2 M solution in methanol) was added to a solution of trisaccharide (20) (43 mg, 0.042 mmol) in anhydrous methanol (3 ml) and held for 2 h. The solution was then concentrated in vacuo, water (3 ml) added, and the mixture held for 3 h. The mixture was then applied to a column (10×50 mm) with Dowex 50×4-400 (H$^+$) cation exchange resin.

The target compound was eluted with 1 M aqueous ammonia and the eluant concentrated in vacuo. Lyophilization from water provided trisaccharide 21 (23 mg, quant.) as a colorless powder. $R_f$ 0.3 (100:10:10:10:2 (v/v/v/v/v) ethanol-n-butanol-pyridine-water-acetic acid), $[\alpha]_D$+42° (c 1; water), m/z 584.9 (H$^+$+Na).

$^1$H NMR, D$_2$O: 1.98-2.05 (m, 2H, —CH$_2$—), 3.17 (m, 2H, —CH$_2$NH$_2$), 3.33-3.35 (m, 1H, H-2a), 4.36 (m, 1H, H-5c), 4.53 (d, 2H, J=7.8, H-1a, H-1b), 4.97 (d, 1H, J$_{1,2}$=3.67, H-1c).

SCHEME VII
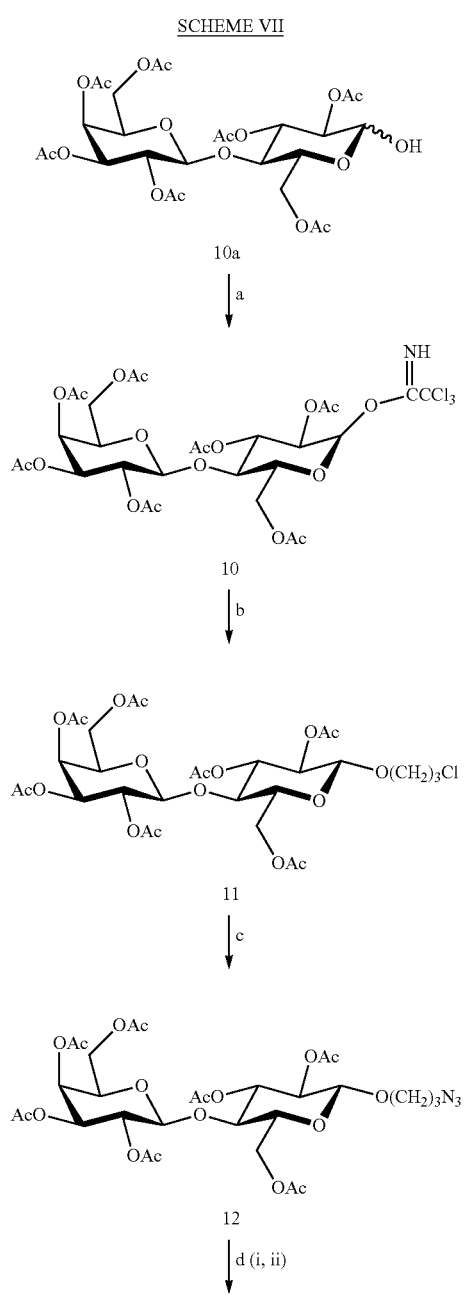
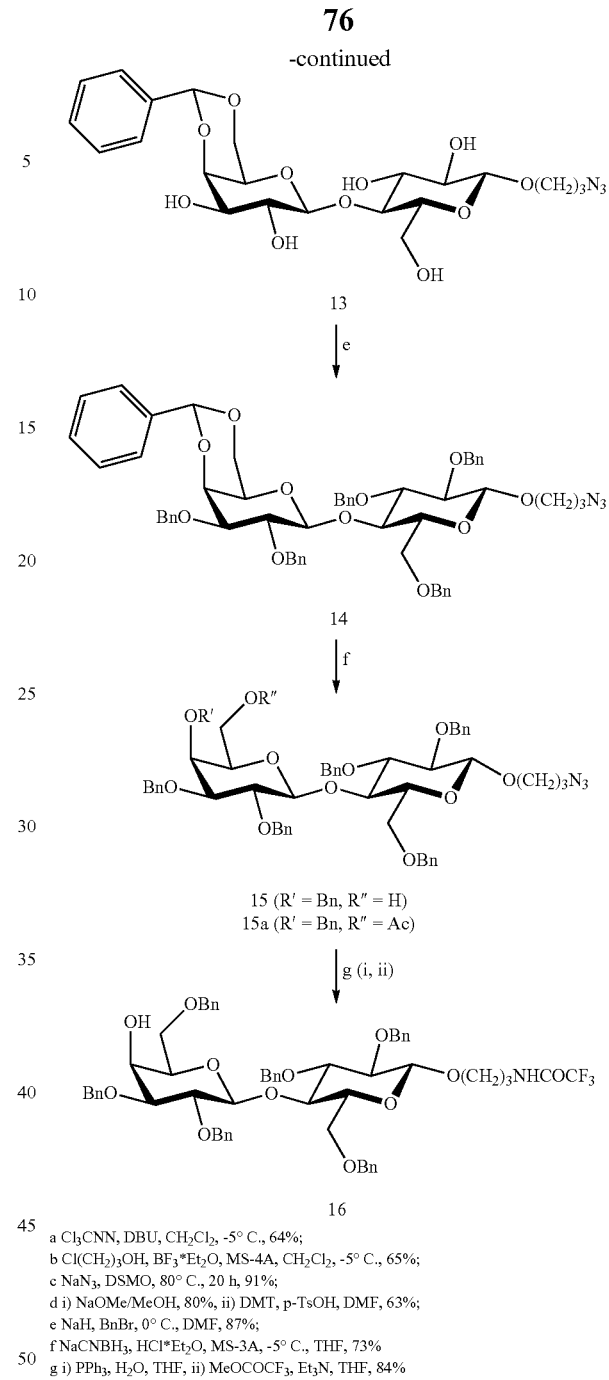
a Cl₃CNN, DBU, CH₂Cl₂, -5° C., 64%;
b Cl(CH₂)₃OH, BF₃*Et₂O, MS-4A, CH₂Cl₂, -5° C., 65%;
c NaN₃, DSMO, 80° C., 20 h, 91%;
d i) NaOMe/MeOH, 80%, ii) DMT, p-TsOH, DMF, 63%;
e NaH, BnBr, 0° C., DMF, 87%;
f NaCNBH₃, HCl*Et₂O, MS-3A, -5° C., THF, 73%
g i) PPh₃, H₂O, THF, ii) MeOCOCF₃, Et₃N, THF, 84%
SCHEME VIII
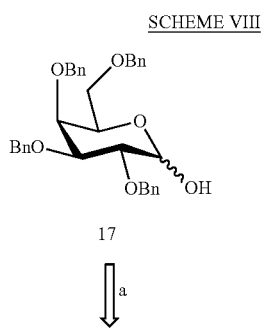

-continued
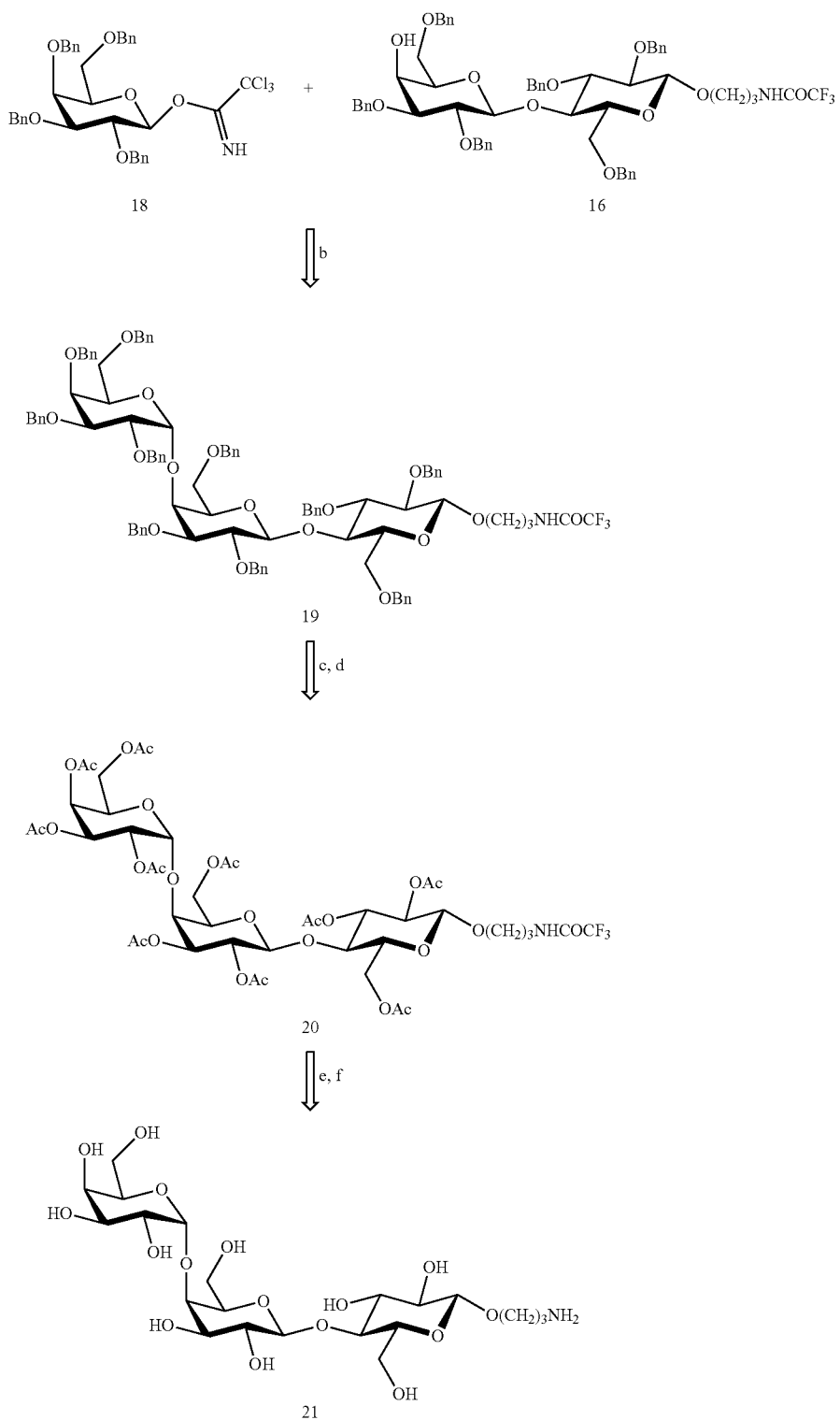
a Cl₃CNN, K₂CO₃, CH₂Cl₂, 60%;
b TMSOTf, MS-4A, CH₂Cl₂, 72%
c H₂, 10% Pd/C, MeOH;
d Ac₂O/Py, 90%
e MeONa/MeOH
f NaOH/H₂, 96%

Preparation of 2-azidoethyl (3,4-di-O-acetyl-2,6-di-O-benzyl-α-D-galactopyranosyl)-(1→4)-(2,3,6-tri-O-benzyl-β-D-galactopyranosyl)-(1→4)-2,3,6-tri-O-benzyl-β-D-glucopyranoside (25)

To the solution of ethyl 3,4-di-O-acetyl-2,6-di-O-benzyl-1-thio-β-D-galactopyranoside (23) (550 mg, 1.11 mmol) in dichloromethane (10 ml) was added $Br_2$ (57 μl, 1.11 mmol). The mixture was held for 20 min at room temperature, then concentrated in vacuo at room temperature and co-evaporated with anhydrous benzene (3×30 ml). The crude 3,4-di-O-acetyl-2,6-di-O-benzyl-α-D-galactopyranosylbromide (24) was used for glycosylation without purification.

The mixture of lactose derivative 22 (Sun et al (2006)) (500 mg, 0.525 mmol), 1,1,3,3-tetramethylurea (300 μl), molecular sieves MS 4 Å (1 g), and dichloromethane (25 ml) was stirred for 30 min at room temperature. Silver trifluoromethanesulfonate (285 mg, 1.11 mmol), molecular sieves MS 4 Å (0.5 g), and the freshly prepared galactopyranosyl-bromide (24) in dichloromethane (15 ml) were then added. The reaction mixture was stirred overnight, filtered, and concentrated in vacuo.

Column chromatography on Silica gel (elution with 3:1 to 1:1 (v/v) hexane-ethyl acetate) resulted in 570 mg (79%) of trisaccharide 25, $R_f$ 0.25 (2:1 (v/v) hexane-ethyl acetate); $[\alpha]_D$+32° (c 0.8, $CHCl_3$)

$^1$H NMR, $CDCl_3$: 1.88, 1.94 (2s, 2Ac), 3.00 (dd, 1H, $J_{5,6}$=4.9, $J_{6',6}$=8.4, H-6a), 3.19 (dd, $J_{1,2}$=8.5, $J_{2,3}$=8.9, H-2a), 3.30-3.36 (m, 2H, —CHHN$_3$, H-6'a), 3.38-3.47 (m, 4H, H-5a, H-5b, H-2b, H-6b), 3.48-3.54 (m, 1H, —CHHN$_3$), 3.61 (dd, 1H, $J_{2,3}$=8.9, $J_{3,4}$=9.2, H-3a), 3.69-3.75 (m, 3H, H-6'b, H-6c, —OCHH—), 3.85 (dd, 1H, $J_{5,6}$=4.6, $J_{6,6'}$=11.0, H-6c), 3.89 (dd, 1H, $J_{1,2}$=3.4, $J_{2,3}$=10.8, H-2c), 3.95 (dd, 1H, $J_{3,4}$=9.2, $J_{4,5}$=9.5, H-4a), 4.0-4.1 (m, 4H, —OCHH—, H-4b, CH$_2$Ph), 4.25, 4.29, 4.32, 4.39 (4 d, 4×1H, $J_{AB}$=12, 4 —CHPh), 4.43 (d, 1H, $J_{1,2}$=7.6, H-1), 4.48 (d, 1H, $J_{1,2}$=7.6, H-1), 4.54-4.62 (m, 5H, 4 —CHPh, H-5c), 4.71-4.84 (m, 4H, 4 —CHPh), 4.89, 4.91, and 5.09 (3 d, 3×1H, 3 4 —CHPh), 5.15 (d, 1H, $J_{1,2}$=3.0, H-1c), 5.39 (dd, 1H, $J_{2,3}$=10.8, $J_{3,4}$=3.4, H-3c), 5.56 (dd, 1H, $J_{3,4}$=3.4, $J_{4,5}$=0.9, H-4c), 7.14-7.48 (m, 40H, Ph).

Preparation of 2-aminoethyl α-D-galactopyranosyl-(1→4)-β-D-galactopyranosyl-(1→4)-β-D-glucopyranoside (Gb$_3$-S$_1$) (28)

Sodium methylate (100 μl of 2 M solution in methanol) was added to a suspension of trisaccharide (25) (500 mg, 0.363 mmol) in anhydrous methanol (50 ml). The mixture was stirred overnight at room temperature, quenched with acetic acid, and concentrated in vacuo.

Column chromatography on Silica gel (elution with 2:1 to 1:1 (v/v) hexane-ethyl acetate) resulted in 470 mg of trisaccharide (26), $R_f$ 0.5 (1:1 (v/v) hexane-ethyl acetate), $[\alpha]_D$+36° (c 0.5, $CHCl_3$).

To a solution of trisaccharide (26) and Boc$_2$O ((150 mg, 0.91 mmol) in anhydrous methanol (50 ml) was added the catalyst 10% Pd/C (500 mg). The mixture was degassed and the flask filled with hydrogen. The reaction mixture was stirred for 3 h, filtered off from the Pd/C, and concentrated in vacuo.

Column chromatography on Silica gel (elution with 6:5:1 (v/v/v) chloroform-ethanol-water) resulted in 160 mg (68%) of trisaccharide 27 $R_f$ 0.3 (6:5:1 (v/v/v) dichloromethane-ethanol-water). $^1$H NMR, $D_2O$: 1.45 (s, 9H, $(CH_3)_3$COCO—), 4.53 (d, 1H, $J_{1,2}$=7.8, H-1b), 4.58 (d, 1H, $J_{1,2}$=7.4, H-1b), 4.98 (d, 1H, $J_{1,2}$=3.0, H-1c).

The trisaccharide 27 was then treated with 95% CF$_3$COOH (5 ml, 10 min). Upon completion, the mixture was concentrated in vacuo, co-evaporated with toluene, and applied to a column (10×100 mm) of Dowex 50×4-400 (H$^f$) cation exchange resin. The target compound was eluted with 1 M aqueous ammonia and the eluant was concentrated in vacuo. Lyophilization from water provided trisaccharide 28 (135, quant.) as a colorless powder. $R_f$ 0.35 (100:10:10:10:2 (v/v/v/v/v) ethanol-n-butanol-pyridine-water-acetic acid), $[\alpha]_D$+25° (c 0.2; water).

$^1$H NMR, $D_2O$: 3.32 (m, 2H, —CH$_2$NH$_2$), 3.40-3.45 (m, 1H, H-2a), 3.63 (dd, 1H, $J_{1,2}$=7.9, $J_{2,3}$=10.3, H-2b), 3.66-3.78 (m, 5H, H-5a, H-3a, H-4a, H-6c, H-6'c), 3.8 (dd, 1H, $J_{3,4}$=3.1, $J_{3,2}$=10.3, H-3b), 3.84 (m, 2H, $J_{5,6}$=4.4, $J_{5,6'}$=7.9, H-5b), 3.88-3.92 (m, 3H, H-2c, H-6b, —OCHH—), 3.96 (dd, 1H, $J_{3,4}$=3.3, $J_{3,2}$=10.3, H-3c), 3.98-4.03 (m, 2H, H-6a, H-6'b), 4.06 (dd, 1H, $J_{5,6}$=2.2, $J_{6,6'}$=12.3, H-6'a), 4.08 (dd, 1H, $J_{3,4}$=3.3, $J_{4,5}$=0.9, H-4c), 4.09 (d, 1H, $J_{3,4}$=3.1, H-4b), 4.17-4.21 (m, 1H, —OCHH—), 4.41 (m, 1H, H-5c), 4.56 (d, 1H, J=7.9, H-1b), 4.60 (d, 1H, J=8.1, H-1a), 5.00 (d, 1H, $J_{1,2}$=3.9, H-1c).

SCHEME IX

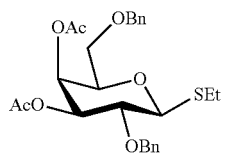

23

↓a

-continued
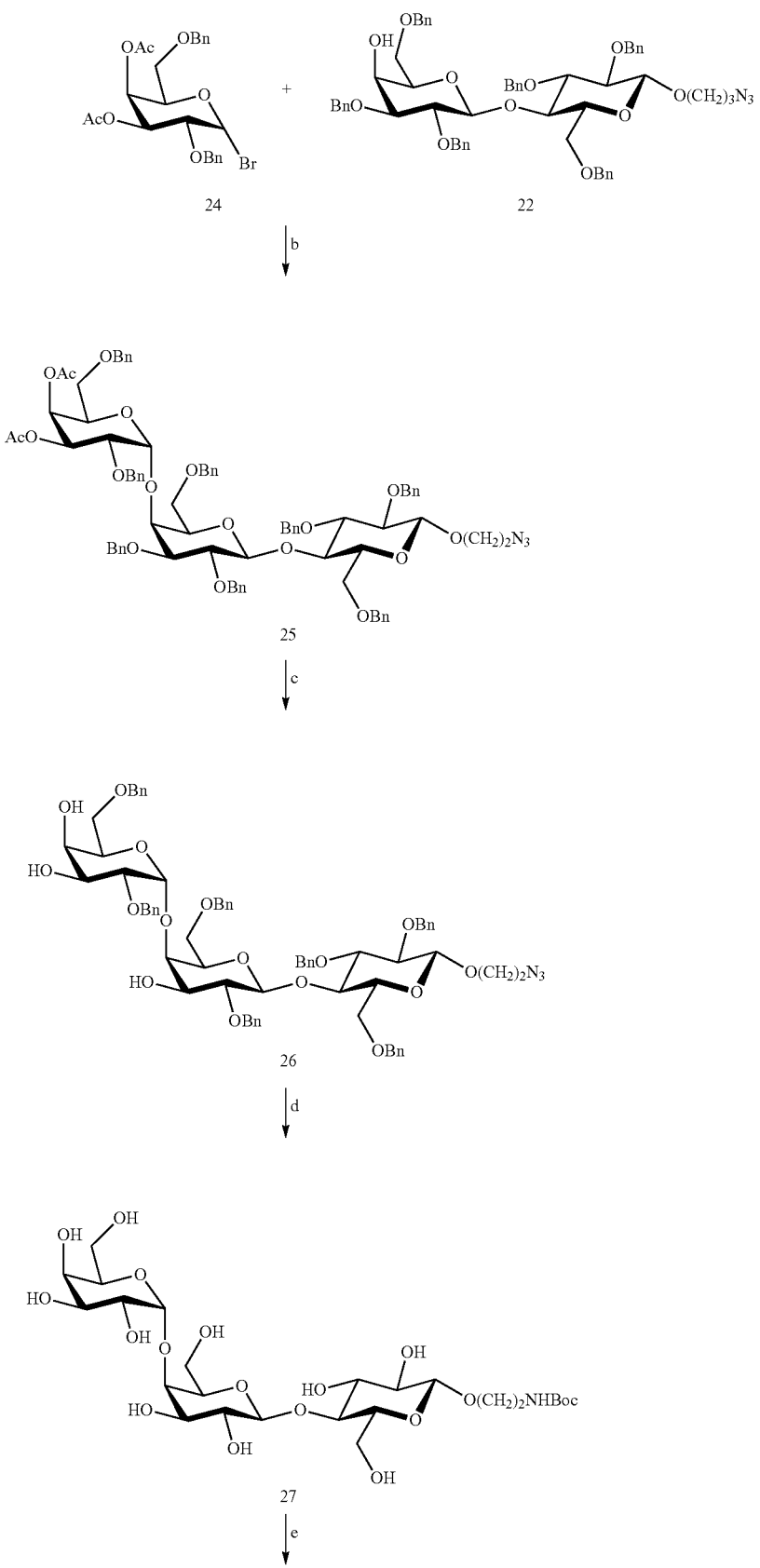

-continued

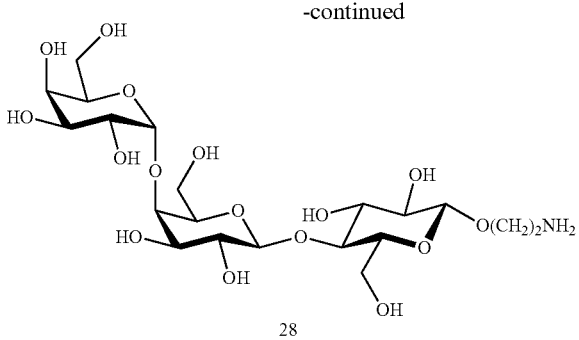

28 a Br₂, CH₂Cl₂, +4° C., 100%;
b AgOTf, MS-4A, CH₂Cl₂, 78%
c MeONa/MeOH—CH₂Cl₂;
d H₂, 10% Pd/C, MeOH, Boc₂O, 70%;
e CF₃COOH (95%), 96%

The preparation of the primary amino propyl glycosides GalNAcα1-3(Fucα1-2)Galβ-O(CH₂)₃NH₂ ($A^{tri}$-$S_1$) and Galα1-3(Fucα1-2)Galβ-O(CH₂)₃NH₂ ($B_{tri}$-$S_1$) is described in the publication of Korchagina and Bovin (1992). The preparation of the primary amino propyl glycosides Xylα1-3Glcβ-O(CH₂)₃NH₂ and Xylα1-3Xylα1-3Glcβ-O(CH₂)₃NH₂ is described in the publication of Krylov et al (2007). The preparation of the primary amino propyl glycosides Neu5Acα2-3Galβ1-3(Fucα1-4)GlcNAcβ-O(CH₂)₃NH₂ (sLe$^a$-$S_1$) and Neu5Acα2-3Galβ1-4(Fucα1-3)GlcNAcβ-O(CH₂)₃NH₂ (sLe$^x$-$S_1$) is described in the publication of Nifant'ev et al (1996). The preparation of the primary amino propyl glycosides GalNAcα1-3(Fucα1-2)Galβ1-4GlcNAcβ-O(CH₂)₃NH₂ ($A_{tetra}$(Type 2)-$S_1$), Galα1-3(Fucα1-2)Galβ1-4GlcNAcβ-O(CH₂)₃NH₂ ($B_{tetra}$ (Type 2)-$S_1$) Fucα1-2Galβ1-4GlcNAcβ-O(CH₂)₃NH₂ ($H_{tri}$ (Type 2)-$S_1$), Galβ1-4(Fucα1-3)GlcNAcβ-O(CH₂)₃NH₂ (Le$^x$-$S_1$), Fucα1-2Galβ1-4(Fucα1-3)GlcNAcβ-O(CH₂)₃NH₂ (Le$^y$-$S_1$), Galα1-3Galβ1-4GlcNAcβ-O(CH₂)₃NH₂ ($B_{tri}$(Type 2)-$S_1$) and Galα1-4Galβ1-4GlcNAcβ-O(CH₂)₃NH₂ ($P_1$-$S_1$) is described in the publication of Pazynina et al (2002). The preparation of the primary amino propyl glycosides Neu5Acα2-3Galβ-O(CH₂)₃NH₂, Neu5Acα2-3Galβ1-4GlcNAcβ-O(CH₂)₃NH₂ (3'SLN-$S_1$), Neu5Acα2-3Galβ1-4(6-HSO₃)GlcNAβ-O(CH₂)₃NH₂ (6-Su-3'SLN-$S_1$), Neu5Acα2-3Galβ1-3GalNAcα-O(CH₂)₃NH₂ (SiaTF-$S_1$), Neu5Acα2-3Galβ1-3(6-HSO₃)GalNAcα-O(CH₂)₃NH₂ (6-Su-SiaTF-$S_1$), Neu5Acα2-3Galβ1-3GlcNAcβ-O(CH₂)₃NH₂ (SiaLe$^c$-$S_1$), Neu5Acα2-3Galβ1-3(6-HSO₃)GlcNAcβ-O(CH₂)₃NH₂ (6-Su-SiaLe$^c$-$S_1$), Neu5Acα2-3Galβ1-3(Fucα1-4)GlcNAcβ-O(CH₂)₃NH₂ (SiaLe$^a$-$S_1$), Neu5Acα2-3Galβ1-4(Fucα1-3)GlcNAcβ-O(CH₂)₃NH₂ (SiaLe$^x$-$S_1$) is described in the publication of Pazynina et al (2003). The preparation of the primary amino propyl glycoside Galβ1-4GlcNAcβ1-3Galβ1-4GlcNAcβ1-3Galβ1-4GlcNAcβ-O(CH₂)₃NH₂ (trilactosamine-$S_1$) is described in the publication of Pazynina et al (2008). The preparation of the primary amino propyl glycosides Neu5Ac-α-(2-6')-Galβ1-4GlcNAcβ-O(CH₂)₃NH₂ (Neu5Ac-α-(2-6')-lactosamine-$S_1$) and Neu5Gc-α-(2-6')-Galβ1-4GlcNAcβ-O(CH₂)₃NH₂ (Neu5Gc-α-(2-6')-lactosamine-$S_1$) is described in the publication of Sherman et al (2001).

Preparation of Galili-CMG(2)-DOPE (22)

Figure 4:
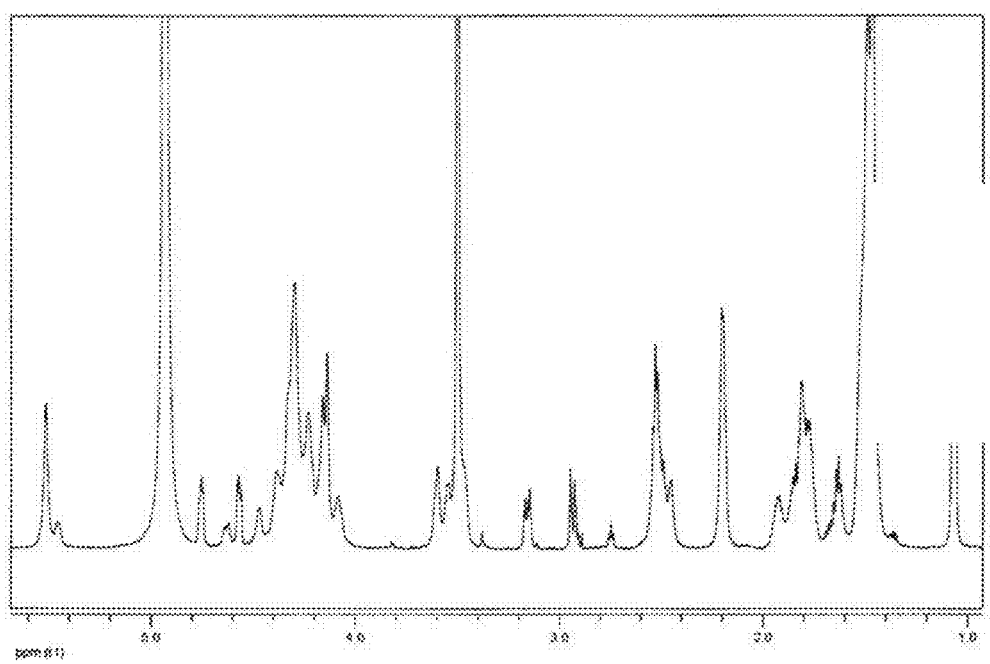
FIG. 4. $^1$H NMR spectrum of Biotin-CMG(2)-Ad-DOPE (I) (2.5 mg/ml in CD$_3$OD/D$_2$O 1:1, δ ppm, 600 MHz).
Figure 5:
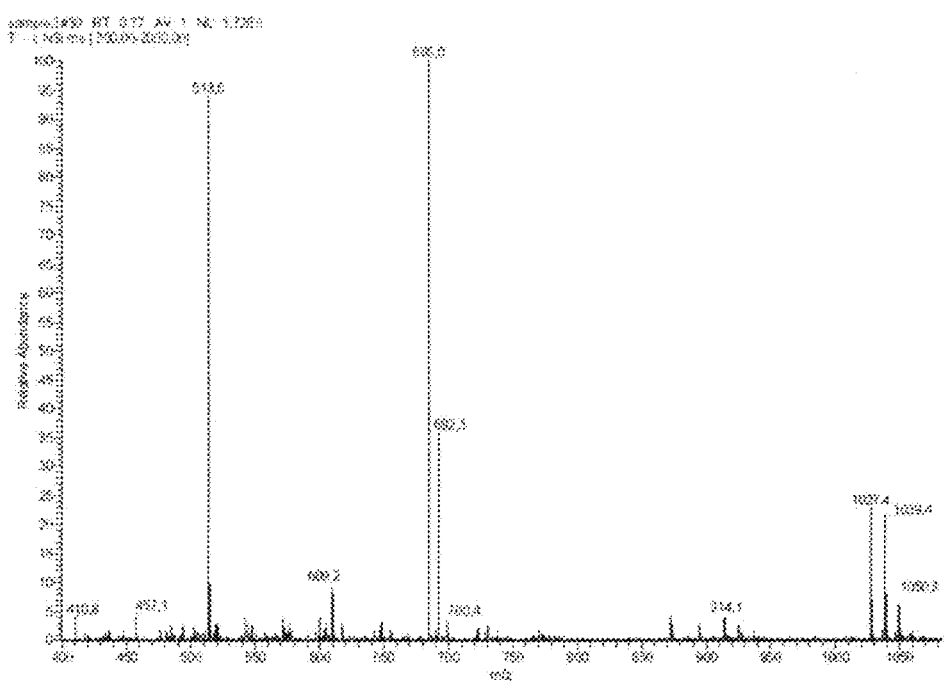
FIG. 5. ESI-MS spectrum of Biotin-CMG(2)-Ad-DOPE (I) (ThermoFinnigan LCQDecaXP (negative mode, 30% MeOH)).

To a stirred solution of compound 21 (66 mg, 0.079 mmol) in dry DMSO (6 mL) were added 15 μl Et₃N and powdered H₂N-CMG(2)-DOPE (20) (95 mg, 0.0495 mmol) in 3 portions. The mixture was stirred for 24 h at room temperature and then subjected to column chromatography (Sephadex LH-20, i-PrOH—H₂O, 1:2, 0.5 v % Py, 0.25 v % AcOH) to yield the crude compound 22 in a form of Py-salt; The compound was lyophilized from water two times, then dissolved again in 10 ml of water, aqueous solution of NaHCO₃ (50 mM) was added to pH 6.5 for obtaining the compound 22 in a form of Na-salt and the solution was subjected to lyophilization. The yield of compound 22 (Na-salt) was 114 mg (86% based on NH₂—CMG₂-DE), $R_f$ 0.6 (i-PrOH-MeOH-MeCN-H₂O, 4:3:6:4). ¹H NMR (FIG. 4) (700 MHz, D₂O-CD₃OD, 1:1 (v/v), 40° C.; selected signals) δ, ppm: 1.05 (t, J 7.03 Hz, 6H; 2 C$\underline{H}_3$), 1.40-1.58 (m, 40H; 20 C$\underline{H}_2$), 1.73-1.87 (m, 12H; 2×-COCH₂C$\underline{H}_2$C$\underline{H}_2$CH₂CO and 2×-COCH₂C$\underline{H}_2$—), 1.90-1.99 (m, 2H; OCH₂C$\underline{H}_2$CH₂N), 2.15-2.25 (m, 11H; 2×-C$\underline{H}_2$CH=CHC$\underline{H}_2$—, NHC(O)C$\underline{H}_3$), 2.39-2.59 (2m, total 12H, 2×-COCH₂C$\underline{H}_2$CH₂CH₂CO— and 2×-COCH₂C$\underline{H}_2$—) 4.63 (dd, 1H, J 2.51, J 12.20, C(O)OC$\underline{H}$HCHOCH₂O—), 4.67 and 4.69 (2d×1H, $J_{1,2}$ 7.81, $J_{1,2}$ 7.95, H-1$^I$, H-1$^{II}$), 5.30 (d, 1H, $J_{1,2}$ 3.88, H-1$^{III}$), 5.42-5.46 (m, 1H, —OCH₂—CHO—CH₂O—), 5.49-5.59 (m, 4H, 2×-C$\underline{H}$=C$\underline{H}$—); MALDI TOF mass-spectrum, M/Z: 2567 (M+Na); 2583 (M+K); 2589 (MNa+Na); 2605 (MNa+K); 2611 (MNa₂+Na).

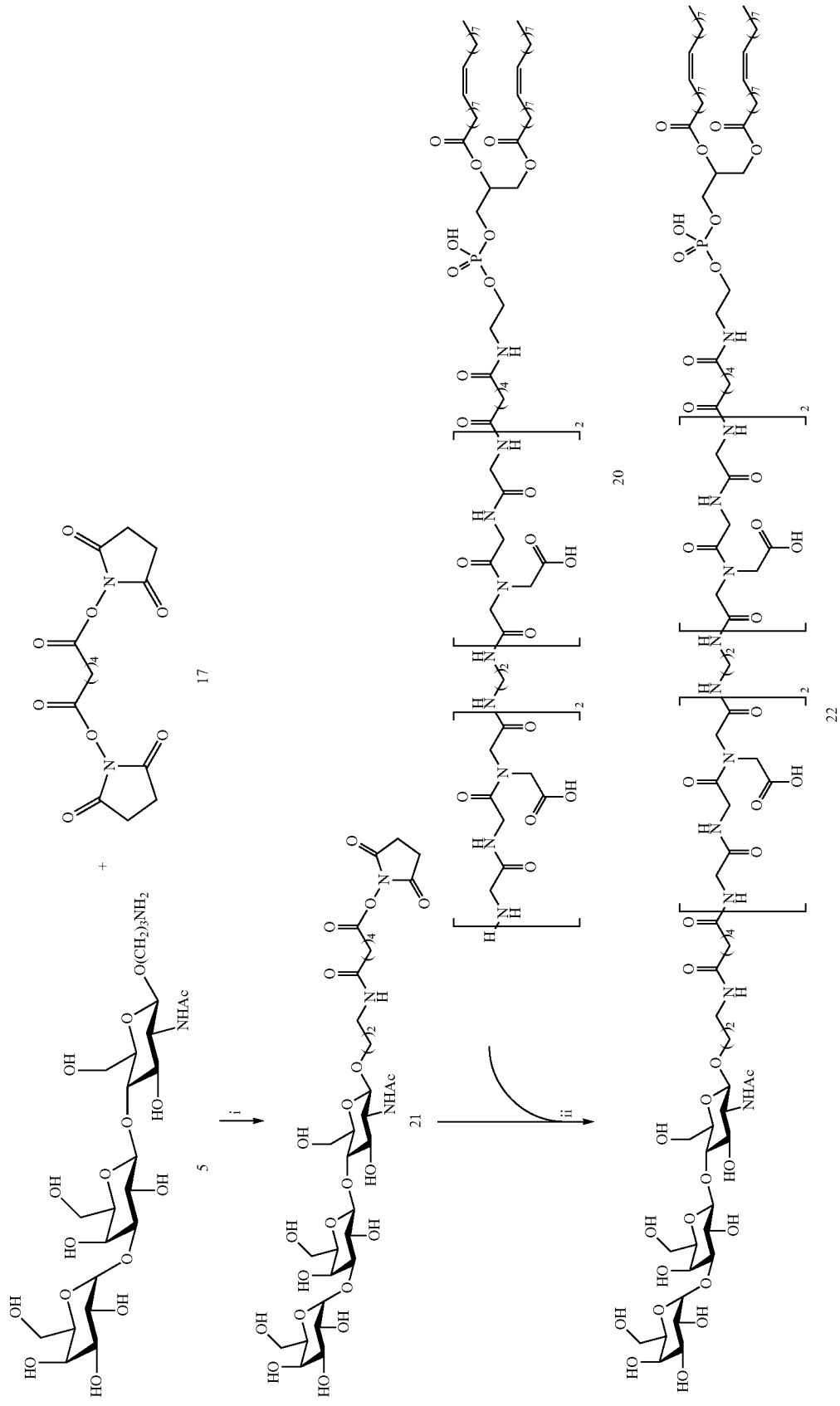

Biology

The use of the peptide-lipid constructs in methods for effecting qualitative and quantitative changes in the levels of peptide expressed at the surface of cells and multi-cellular structures was illustrated with reference to serodiagnosis. In the following table cross-reactivity of polyclonal sera and monoclonal antibodies of known specificities and red blood cells (RBCs) modified with the construct DOPE-Ad-CMG(I)-βAla-Mal-Mur(D14C) (XI) (2 hours, 37° C.) is summarized.

| Reagent ID | | Type | EIA/Miltenberger Specificity |
|---|---|---|---|
| 2 | T217 | Human group AB serum | Reactive with MUT-T peptides by EIA |
| 3 | T165 | Human group O serum | Reactive with MUR peptides by EIA |
| 4 | T7202 | Human group B serum | Reactive with MUT-M peptides by EIA |
| 6 | T6025 | Human group A serum | Reactive with MUT-T peptides by EIA |
| 7 | T8445 | Human group O serum | Uncertain |
| 8 | T5896 | Human group O serum | Uncertain |
| 9 | MIII | Monoclonal antibody | Reactive with Mi III red cells |
| 10 | Mia | Monoclonal antibody | Reactive with Mi III red cells |
| 11 | Mur | Monoclonal antibody | Reactive with Mur positive red cells |
| 12 | Gam | IgG monoclonal antibody | Reactive with Mi III red cells |
| 13 | BoxH | Human serum | Uncertain |
| 14 | TAP1 | Human group O serum | Presumed MUT-K specificity |
| 15 | TAP2 | Human serum | Presumed MUR specificity |

| | Antibody ID | | Specificities | Transformed cells | Untransformed cells |
|---|---|---|---|---|---|
| Expected postives | T165 | serum | Mur | 10 | 0 |
| | T6025 | serum | K + Mur | 5 | 0 |
| | T8445 | serum | Mur + Hil + Tsen | 5 | 0 |
| | T5896 | serum | M + K + (Mur) | 0 | 0 |
| Expected negatives | Japan T4130 | MoAb serum | Mur Hil + Tsen | 0 | 0 |
| | T217 | serum | T | 0 | 0 |
| | T7202 | serum | M | 0 | 0 |
| | T8012 | serum | M + K + T | 0 | 0 |
| | Japan | MoAb | Mi III (1:10) | 0 | 0 |
| | Box Hill | serum | ? | 0 | 0 |
| | Japan | MoAb | Mi$^a$ (1:50) | 0 | 0 |
| | E119 KBL 7201 | MoAb | Mia GAMMA(1:100) | 0 | 0 |

Modification of Red Blood Cells with Peptide-Lipid Constructs

Red blood cells are modified by mixing 1 part by volume of washed packed red blood cells with 1 part by volume of peptide-lipid construct dispersed at a concentration of 10 to 1000 pg/ml in cell media (Celpresol™).

The suspensions are either:

1. incubated for 2 hours at 37° C. before being washed and suspended in a cell medium for serological analysis at a concentration of 0.8 to 3% (Method 1); or 2. incubated for 3 to 4 hours at room temperature (circa 25° C.) followed by 18 hours at 4° C. before being washed and suspended in a cell medium for serological analysis at a concentration of 0.8 to 3% (Method 2).

Tube Serology Testing of Modified Red Blood Cells

Serological reactions are graded or scored by either of two established systems (0 or '−' no agglutination, 1+ or 3=very weak agglutination, 2+ or 5=weak agglutination, 3+ or 8=moderate strong agglutination, 4+ or 10/12=strong agglutination)

Serological platforms used are Tube (addition of reagents and reactants into plastic or glass serology tubes and after appropriate incubations, washing and centrifugation observing reactions macroscopically by eye and a 10× magnification eyepiece and scoring) and BioVue™ (addition of reactants into cassettes containing beads (including some reactants) and after appropriate incubations and centrifugation observing the reaction patterns trapped within the Gel matrix). BioVue is the serological column agglutination platform of Ortho-Clinical Diagnostics. Diamed is the serological column agglutination platform of Diamed AG.

Serum samples were available from 47 blood donors of negative antibody screen status. These samples were designated "negative samples", but not determined not to have anti-Miltenberger antibodies).

Three serum samples known to have Miltenberger related antibodies T217, T6025, T5896. These samples were designated "positive samples", but not determined to have anti-antibodies against the peptide of the peptide of the construct designated DOPE-PEG$_6$-βAla-Mal-Milt(K) (M00).

A suspension of 3% modified RBCs was prepared in PBS and 30 µl of the suspension mixed with 30 µl serum sample. The mixtures were then incubated for 45 min at 37° C. Following incubation the RBCs were centrifuged for 10 s in an Immufuge™ (setting: "high") and observed for agglutination before being washed 3 times with PBS.

After washing one drop of Epiclone™ anti-human globulin (AHG) was added and the tubes then centrifuged for 10 s in an Immufuge™ (setting: "high"). Tubes were then read and serology scores recorded.

Comments on the observed serology scores are provided in the legends to the following tables.

TABLE 1

Summary of reactivity of samples of serum from 47 blood donors not expected to have anti-Miltenberger activity ("negative samples"). AHG+ means sample reacted by the anti-human globulin test. AHG– means sample is unreactive. RBCs were modified with the peptide-lipid construct designated DOPE-PEG$_6$-βAla-Mal-Milt(K) at the concentrations indicated. Sera were tested against modified RBCs following 3 days storage.

| Age of modified RBCs (days) | Serum | Concentration of DOPE-PEG$_6$-βAla-Mal-Milt(K)(M00) (mg/ml) | | | | | |
|---|---|---|---|---|---|---|---|
| | | 1.0 (n = 47) | | 0.5 (n = 21) | | 0.25 (n = 21) | |
| | | AHG+ | AHG– | AHG+ | AHG– | AHG+ | AHG– |
| 3 | Negative samples | 1 | 46 | 0 | 21 | 0 | 21 |

TABLE 2

Results by tube serology of 3 serums known to contain antibodies against antigens of the Miltenberger complex. Score results show sample reactivity by the anti-human globulin test, 1+ = weak, 2+ = medium, 3+ = medium/strong, 4+ = strong, — means sample is unreactive. RBCs were modified with the peptide-lipid construct at the concentrations indicated. Sera were tested against modified RBCs following 3 days and 24 days storage. (n.t.—not tested).

| Age of modified RBCs (days) | Serum | Concentration of DOPE-PEG$_6$-βAla-Mal-Milt(K)(M00) (mg/ml) | | |
|---|---|---|---|---|
| | | 1.0 | 0.5 | 0.25 |
| 3 | T217 | 2+ | 1+ | — |
| 3 | T6025 | 4+ | 4+ | 4+ |
| 3 | T5896 | — | — | — |
| 24 | T217 | — | — | n.t. |
| 24 | T6025 | 2+ | 2+ | n.t. |
| 24 | T5896 | — | — | n.t. |

TABLE 3

Results by Diamed column serology of 3 serums known to contain antibodies against the Miltenberger complex. Score results show sample reactivity by the anti-human globulin test, 1+ =weak, 2+ = medium, 3+ = medium/strong, 4+ = strong, — means sample is unreactive. RBCs were modified with the peptide-lipid construct at the concentrations indicated. Sera were tested against modified RBCs following 3 days and 24 days storage.

| Age of modified RBCs (days) | Serum | Concentration of DOPE-PEG$_6$-βAla-Mal-Milt(K)(M00) (mg/ml) | | |
|---|---|---|---|---|
| | | 1.0 | 0.5 | 0.25 |
| 3 | T217 | — | — | 1+ |
| 3 | T6025 | 1+ | 2+ | 1+ |
| 3 | T5896 | — | — | — |
| 24 | T217 | — | — | — |
| 24 | T6025 | 2+ | 2+ | 1+ |
| 24 | T5896 | — | — | — |

TABLE 6

Identification of naturally occurring Miltenberger antigen positive (Milt$^+$) human red cells as determined in BioVue AHG cards.

| | | Polyclonal sera | | | | | | | | Monoclonal antibodies | | | |
|---|---|---|---|---|---|---|---|---|---|---|---|---|---|
| Cell ID | Antigen | 2 T217 | 3 T165 | 4 T7202 | 6 T6025 | 7 T8445 | 8 T5896 | 14 TAP1 | 15 TAP2 | 9 MIII | 10 Mia | 11 Mur | 12 Gam |
| 9422184 | Vw | 8 | 5 | 3 | 0 | 8 | 0 | 5 | 0 | 0 | 10 | 0 | 12 |
| 11297161 | MiIII | 12 | 10 | 12 | 12 | 10 | 10 | 10 | | 10 | 10 | 12 | 12 |
| 4131850 | MiIV | 12 | | | 12 | | | | 10 | 0 | 10 | 12 | 12 |
| 1523 | MiVI | 12 | | | 12 | | | | 8 | 0 | 10 | 12 | 10 |
| T1569 | MiVII | 0 | 0 | 0 | 0 | 10 | 0 | 0 | | 0 | 0 | 0 | 0 |
| C.BR | Mi?X | 12 | 10 | 12 | 12 | 8 | 12 | 12 | 8 | 0 | 10 | 10 | 10 |

TABLE 7

Identification of peptide-lipid constructs. Lowercase 'c' denotes a cysteine residue (Cys). All peptide Lipid constructs (F-S-L or L-S-F) were prepared as the DOPE (L) variant. M refers to a shorthand name for the molecule construct and is used in the following tables. The terminal peptide sequence is as indicated with. "little c" representing Cys via which S is linked to L. Spacer refers to the structural motif of the spacer (S). CMG denotes the peptide-lipid constructs described in this specification. PEG denotes peptide-lipid constructs of the structure described as the second aspect of the invention in the specification accompanying the international PCT application filed on 11 Sep. 2008 at the Intellectual Property Office of New Zealand as receiving Office (RO/NZ). All constructs were prepared as the DOPE variant.

| | Peptide sequence | | | | | | | | | | | | Leader | spacer |
|---|---|---|---|---|---|---|---|---|---|---|---|---|---|---|
| 13 MUTK | Ser | Ser | Gln | Thr | Asn | Asp | Lys | His | Lys | Arg | Asp | Thr Tyr | c | PEG6 |
| 34 MUTK | Ser | Ser | Gln | Thr | Asn | Asp | Lys | His | Lys | Arg | | | c | CMG(2) |
| 21 MUTK | | Ser | Gln | Thr | Asn | Asp | Lys | His | Lys | Arg | Asp | | c | CMG(2) |
| 22 MUTK | | Ser | Gln | Thr | Asn | Asp | Lys | His | Lys | Arg | Asp | | c | CMG(2) |
| 36 MUTK | | Ser | Gln | Thr | Asn | Asp | Lys | His | Lys | Arg | Asp | Thr | c | CMG(2) |
| 35 MUTK | | | Gln | Thr | Asn | Asp | Lys | His | Lys | Arg | Asp | Thr | c | CMG(2) |
| 1 MUTK | | | Gln | Thr | Asn | Asp | Lys | His | Lys | Arg | Asp | Thr Tyr | AAAAA | PEG6 |
| 2 MUTK | | | Gln | Thr | Asn | Asp | Lys | His | Lys | Arg | Asp | Thr Tyr | GSerGSerGc | PEG6 |
| 3 MUTK | | | Gln | Thr | Asn | Asp | Met | His | Lys | Arg | Asp | Thr Tyr | GSerGSerGc | PEG6 |
| 9 MUTK | | | Gln | Thr | Asn | Asp | Lys | His | Lys | Arg | Asp | Thr Tyr | GSerGSerGc | CMG(2) |
| 33 MUTK | | | Gln | Thr | Asn | Asp | Lys | His | Lys | Arg | Asp | Thr Tyr | c | CMG(2) |
| 37 MUTK | | | | Thr | Asn | Asp | Lys | His | Lys | Arg | Asp | Thr Tyr Pro | c | CMG(2) |
| 14 Mur | Asp | Thr | Tyr | Pro | Ala | His | Thr | Ala | Asn | Glu | Val | Ser Glu | c | CMG(2) |
| 14 Mur | Asp | Thr | Tyr | Pro | Ala | His | Thr | Ala | Asn | Glu | Val | Ser Glu | c | CMG(2) |
| 14 Mur | Asp | Thr | Tyr | Pro | Ala | His | Thr | Ala | Asn | Glu | Val | Ser Glu | c | CMG(2) |
| 30 Mur | Asp | Thr | Tyr | Pro | Ala | His | Thr | Ala | Asn | Glu | | | c | CMG(2) |
| 16 Mur | | Thr | Tyr | Pro | Ala | His | Thr | Ala | Asn | Glu | Val | | c | PEG |
| 17 Mur | | Thr | Tyr | Pro | Ala | His | Thr | Ala | Asn | Glu | Val | | c | CMG(2) |
| 28 Mur | | Thr | Tyr | Pro | Ala | His | Thr | Ala | Asn | Glu | | | c | CMG(2) |
| 27 Mur | | Thr | Tyr | Pro | Ala | His | Thr | Ala | Asn | | | | c | CMG(2) |
| 25 Mur | | | Tyr | Pro | Ala | His | Thr | Ala | Asn | Gln | | | c | CMG(2) |
| 26 Mur | | | Tyr | Pro | Ala | His | Thr | Ala | Asn | Glu | Val | | c | CMG(2) |
| 31 Mur | | | Tyr | Pro | Ala | His | Thr | Ala | Asn | Glu | Val | Ser | c | CMG(2) |
| 18 Mur | | | | Pro | Ala | His | Thr | Ala | Asn | Glu | Val | | c | CMG(2) |
| 19 Mur | | | | Pro | Ala | His | Thr | Ala | Asn | Glu | Val | | c | CMG(2) |
| 29 Mur | | | | Pro | Ala | His | Thr | Ala | Asn | Glu | Val | Ser | c | CMG(2) |
| 40 Hil | Glu | Glu | Glu | Thr | Gly | Glu | Thr | Gly | Gln | Leu | | | c | CMG(2) |
| 23 Hil | | Glu | Glu | Thr | Gly | Glu | Thr | Gly | Gln | Leu | Val | | c | CMG(2) |
| 24 Hil | | Glu | Glu | Thr | Gly | Glu | Thr | Gly | Gln | Leu | Val | | c | CMG(2) |
| 41 Hil | | | Glu | Thr | Gly | Glu | Thr | Gly | Gln | Leu | Val | His | c | CMG(2) |

TABLE 8

Analysis of sorted data for the reactivity against the Miltenberger Antibody Positive Panel of RBCs modified to incorporate the MUT peptide-lipid constructs identified at the concentration indicated. Constructs were able to show reactivity with one or more polyclonal serums indicating specificity to one or more peptide variations.

| | | Miltenberger Antibody Positive Panel | | | | | | | | | | | | |
|---|---|---|---|---|---|---|---|---|---|---|---|---|---|---|
| M | µg/ml | 4 T7202 | 8 T5896 | 2 T217 | 6 T6025 | 3 T165 | 14 TAP1 | 7 T8445 | 9 MIII | 10 Mia | 11 Mur | 12 Gam | 13 BoxH | 15 TAP2 |
| 13 | 250 | 8 | 3 | 8 | 8 | 0 | | 0 | 0 | 0 | 0 | 0 | 8 | |
| 34 | 50 | 0 | 0 | 0 | | 0 | 3 | | | | | | | 0 |
| 21 | 200 | 0 | 0 | 0 | 0 | 8 | 8 | | 0 | 0 | 0 | 0 | 3 | 5 |
| 22 | 200 | 0 | 0 | 0 | 10 | 0 | | 0 | 0 | 0 | 0 | 3 | | 0 |
| 36 | 50 | 0 | 0 | 0 | | 0 | 8 | | | | | | | 0 |
| 35 | 50 | 0 | 0 | 0 | | 0 | 5 | | | | | | | 0 |
| 1 | 500 | 5 | 0 | 3 | 8 | 0 | | 0 | 0 | 5 | 0 | 8 | | |
| 2 | 500 | 8 | 8 | 8 | 8 | 5 | | 0 | 0 | 5 | 0 | 8 | | |
| 9 | 300 | 8 | 10 | 8 | 8 | 8 | | 3 | 0 | 0 | 0 | 8 | 10 | |
| 33 | 50 | 0 | 0 | 0 | | 0 | 8 | | | | | | | 0 |
| 37 | 50 | 8 | 0 | 5 | | 0 | 8 | | | | | | | 0 |
| 3 | 1000 | 8 | 10 | 0 | | 5 | | 0 | 0 | 0 | 0 | | 5 | |

TABLE 9

Analysis of sorted data for the reactivity against the Miltenberger Antibody Positive Panel of RBCs modified to incorporate the MUR peptide-lipid constructs identified at the concentration indicated. Constructs were able to show reactivity with one or more polyclonal serums indicating specificity to one or more peptide variations.

| | | Miltenberger Antibody Positive Panel | | | | | | | | | | | |
|---|---|---|---|---|---|---|---|---|---|---|---|---|---|
| M | µg/ml | 3 T165 | 6 T6025 | 7 T8445 | 4 T7202 | 8 T5896 | 2 T217 | 15 TAP2 | 9 MIII | 10 Mia | 11 Mur | 12 Gam | 13 BoxH |
| 14 | 10 | 10 | 10 | 8 | 5 | 0 | 0 | 0 | | 0 | 0 | 0 | | 0 |
| 14 | 50 | 10 | 5 | 8 | 3 | 0 | 0 | | 0 | 0 | 0 | | | |
| 14 | 100 | 10 | 10 | 5 | 5 | 0 | 3 | | 0 | 0 | 0 | | 0 | |
| 30 | 50 | | | 8 | 10 | 0 | 0 | 8 | | | | | |
| 16 | 100 | 10 | 5 | 12 | 5 | 0 | 0 | | 0 | 0 | 0 | 0 | 0 | |
| 17 | 100 | 10 | 10 | 10 | 8 | 0 | 0 | 0 | 0 | 0 | 0 | 0 | | |
| 28 | 50 | | | 8 | 10 | 0 | 0 | 8 | | | | | |
| 27 | 50 | | | 0 | 10 | 0 | 0 | 0 | | | | | |
| 25 | 50 | 3 | 0 | 3 | 0 | 0 | 0 | 8 | 0 | 0 | 0 | 0 | |
| 26 | 50 | 10 | 8 | 8 | 0 | 0 | 0 | 3 | 0 | 0 | 0 | 0 | |
| 31 | 50 | | | 8 | 10 | 0 | 0 | 0 | | | | | |
| 18 | 100 | 10 | 10 | 8 | 0 | 0 | 0 | | 0 | 0 | 0 | 0 | | |
| 19 | 100 | 10 | 8 | 10 | 0 | 3 | 0 | | 0 | 0 | 0 | 0 | | |
| 29 | 50 | | | | 10 | 0 | 0 | 8 | | | | | |

TABLE 10

Negative serum reactivity. Miltenberger negative red cells were modified with the peptide-lipid construct M22 at a transformation concentration of 50 µg/ml and tested against antibody negative serums in the field to determine rates of false positivity. Studies were undertaken in clinical laboratories in Australia, Malaysia and Philippines using three different serological platforms; Column agglutination platforms BioVue and DiaMed as well as the simple technique of tube reactivity. Equal volumes of packed RBCs and a solution containing 50 µg/ml of the construct were contacted for 3 hours at room temperature and then 18 hours at 4° C. This field trial found that clinical antibody negative serums reacted with M22 transformed cells at rates 0.4 to 4.5% in the BioVue ™ platform and at a rate of 0.4% in the DiaMed ™ platform. No reactivity was observed in the tube platform. These results can be considered as false positive reactions.

| | | Number Tested | | | Number Positive | | | % Positive | | |
|---|---|---|---|---|---|---|---|---|---|---|
| Country | Laboratory | BioVue | DiaMed | Tube | BioVue | DiaMed | Tube | BioVue | DiaMed | Tube |
| Australia | CSL | 100 | | | 3 | | | 3.0 | | |
| | Melb Path | 45 | | | 2 | | | 4.5 | | |
| | RNSH | 500 | 500 | | 2 | 2 | | 0.4 | 0.4 | |
| Malaysia | UMMC | 749 | | | 19 | | | 2.5 | | |
| Philippines | Metrop Hosp | | | 60 | | | 0 | | | 0 |

TABLE 11

Positive serum reactivity. Miltenberger negative red cells were modified with the peptide-lipid construct M22 at a transformation concentration of 50 µg/ml, M17 at a transformation concentration of 200 µg/ml, M24 at a transformation concentration of 200 µg/ml, and tested against natural Mi III antibody reactive human serums in the field to determine rates of reactivity. Equal volumes of packed RBCs and a solution containing 50 µg/ml of the construct were contacted for 3 hours at room temperature and then 18 hours at 4° C. The three different constructs of MUT, MUR and HIL were able to discriminate most natural Mi III reactive polyclonal antibodies into specific reactivity profiles. Twelve serums were unreactive with the modified cells, suggesting they may have specificity against another Mi III antigen.

| Sample No. | 22 (50 µg/ml) | 17 (200 µg/ml) | 24 (200 µg/ml) | Interpretation |
|---|---|---|---|---|
| 488-6 | 10 | | | K |
| 9327986660 | 8 | 3 | 0 | K |
| 9325490091 | 5 | 5 | 0 | K |
| 9328791834 | 5 | 3 | 0 | K |
| 621-3 | 5 | | | K |
| 922390844-5 | 0 | 12 | 0 | Mur |
| 9322338631 | 0 | 10 | 0 | Mur |
| 914146821-8 | 0 | 10 | 0 | Mur |
| 932809044-1 | 0 | 8 | 0 | Mur |
| 942433813-3 | 0 | 8 | 0 | Mur |
| 942404708-4 | 0 | 5 | 0 | Mur |
| 942421413-0 | 0 | 5 | 0 | Mur |
| 942223755-1 | 0 | 5 | 0 | Mur |
| 942442720-2 | 0 | 5 | 0 | Mur |
| 927619701-8 | 0 | 3 | 0 | Mur |
| 912485657-9 | 0 | 3 | 0 | Mur |
| 926190919-0 | 0 | 3 | 0 | Mur |
| 9328154853 | 0 | 10 | 3 | Mur + Hil |
| 9328118428 | 0 | 10 | 5 | Mur + Hil |
| 9425256505 | 0 | 8 | 8 | Mur + Hil |
| 942433855-3 | 0 | 8 | 8 | Mur + Hil |
| 942753165-4 | 0 | 8 | 8 | Mur + Hil |
| 9424292604 | 0 | 8 | 5 | Mur + Hil |
| 9427455417 | 0 | 5 | 5 | Mur + Hil |
| S-3 | 0 | 3 | 5 | Mur + Hil |
| 942448627-8 | 0 | 0 | 5 | Hil |
| 942423002-4 | 0 | 0 | 3 | Hil |
| 942762589-1 | 0 | 0 | 3 | Hil |
| 9424248012 | 0 | 0 | 0 | other |
| 9427615156 | 0 | 0 | 0 | other |
| 9424396133 | 0 | 0 | 0 | other |
| 9427613497 | 0 | 0 | 0 | other |
| 927175131-4 | 0 | 0 | 0 | other |
| 932467774-5 | 0 | 0 | 0 | other |
| 927299700-1 | 0 | 0 | 0 | other |
| 926555294-1 | 0 | 0 | 0 | other |
| 932360876-4 | 0 | 0 | 0 | other |
| 927516053-2 | 0 | 0 | 0 | other |
| 942404708-4 | 0 | 0 | 0 | other |
| 589-6 | 0 | | | other |

TABLE 12

Anti-MUT serum reactivity. Miltenberger negative RBCs were modified with the peptide-lipid constructs M22 at concentrations ranging from 10 to 200 µg/ml, M17 at a concentration of 50 µg/ml and M24 at a concentration of 50 µg/ml. The modified cells were tested against a natural Mi III antibody reactive Taiwan human serum (TAP1) detected in the field to determine reactivity profile. Reactivity was compared against natural Mi III antigen positive cells. TAP1 (Taiwan Miltenberger antibody positive sample). TAP1 serum was shown to contain both IgG and IgM antibodies (the latter being saline reactive) directed against natural MiIII positive cells. The lack of reactivity against Abtectcell™ and Phenocell™ antibody screening and identification panels concludes no other antibodies against red cells are present. Reactivity with M22 modifed cells over transformation concentrations of 10 to 200 µg/ml (and not with untransformed cells - 0 µg/ml) concludes the presence of an antibody directed against MUT. The failure of the M22 modified cells to detect a saline reaction, suggests the assay is sensitive to the IgG class of antibody and not IgM - a clinically favourable result. The lack of reactivity with the M17 and M24 transformed cells concludes and absence of antibodies to the MUR and HIL mutations.

| RBCs | Peptide-lipid Construct (µg/ml) | TAP 1 Serum Saline | AHG |
|---|---|---|---|
| Natural Mi III positive cells | | | |
| R2R2, 11297161 | | 8 | 10 |
| R1Rz 11291347 | | 8 | 10 |
| Abtectcell III 8245009 | | | 10 |
| Modified cells | | | |
| M22 (MUT) | 200 | 0 | 10 |
| M22 (MUT) | 100 | 0 | 8 |
| M22 (MUT) | 50 | 0 | 8 |
| M22 (MUT) | 20 | 0 | 8 |
| M22 (MUT) | 10 | 0 | 5 |
| M22 (MUT) | 0 | 0 | 0 |
| M17 (Mur) | | 0 | 0 |
| M24 (Hil) | | 0 | 0 |
| Antibody Screen/ID panel | | | |
| Abtectcell III Batch 2223005 Cells I-III | | | 0 |
| Phenocell B Batch 2653046 Cells 1-11 | | | 0 |

TABLE 13

Anti-MUT serum reactivity. Miltenberger negative red cells were transformed with the peptide-lipid constructs M28 at a concentration of 100 µg/ml and M22 at a concentration of 100 µg/ml and tested against a natural Mi III antibody reactive Taiwan human serum (TAP2) detected in the field to determine reactivity profile. Reactivity was compared against natural Mi III antigen positive cells. TAP 2 (Taiwan Miltenberger antibody positive sample). TAP2 serum was shown to contain IgG antibodies antibodies directed against natural Mi III positive cells. The lack of reactivity against Abtectcell ™ antibody screening and identification panels concludes no other antibodies against red cells are present. Reactivity with M28 modified cells and not with M22 modiifed cells concludes the presence of an antibody directed against the MUR peptide.

| RED CELLS | Peptide-lipid construct (µg/ml) | TAP 2 Serum BioVue AHG |
|---|---|---|
| Natural Mi III positive cells | | |
| Mi III PDN No. 54 | | 5 |
| Mi IV No; 4131850 | | 10 |
| Mi VI 1523A | | 8 |
| Mi ?x ID: CBR | | 8 |
| Vw No: 9422184 | | 0 |
| M28 (MUR) | 100 | 10 |
| M22 (MUT) | 100 | 0 |
| Antibody Screen panel | | |
| Abtectcell III Batch 2223009 Cells I-III | | 0 |

TABLE 14

Identification of the M37 sequence as a candidate for the detection of anti-MUT. Miltenberger negative cells were modiifed with the peptide-lipid constructs M22, M33, M34, M35, M36, M37, M40 and M41 a concentration of 50 µg/ml. Modified cells were tested against serums 2, 3, 4 and 8 of the Miltenberger Antibody Positive Panel and Taiwan Mi III antibody positive serumTAP1 to determine its MUT reactivity profile. TAP 1 (Taiwan Miltenberger antibody positive sample). Cells modified with the peptide-lipid construct M37 were able to detect the anti-MUT activity of Miltenberger Antibody Positive Panel samples 2 and 4. Sample 3 containing MUR activity was expected negative. Sample 8 containing multiple antibodies was unexpectedly negative, but may have lost specificity. TAP1 serum was able to detect all MUT variations, indicating some polyclonal serums may have less defined anti-MUT activity than others.

| Positive Sample | ID | Specificities | BioVue |||||||| |
|---|---|---|---|---|---|---|---|---|---|---|---|
| | | | M22 | M33 | M34 | M35 | M36 | M37 | M40 | M41 | Unmodified |
| 3 | T165 | Mur | 0 | 0 | 0 | 0 | 0 | 0 | 0 | 0 | 0 |
| 8 | T5896 | M + K + Mur | 0 | 0 | 0 | 0 | 0 | 0 | 0 | 0 | 0 |
| 2 | T217 | T | 0 | 0 | 0 | 0 | 0 | 5 | 0 | 0 | 0 |
| 4 | T7202 | M | 0 | 0 | 0 | 0 | 0 | 8 | 0 | 0 | 0 |
|  | TAP1 |  | 8 | 3 | 5 | 5 | 8 | 8 | 0 | 0 | 0 |

| | | MUT peptides | | | | | | | | | | MUT ||| MUT/MUR | MUR |
|---|---|---|---|---|---|---|---|---|---|---|---|---|---|---|---|---|
| | | | | | | | | | | | | #2 | #4 | TAP1 | #8 | #3 |
| 34 | MUTK4 | S | S | Q | T | N | D | K | H | K | R | | − | − | ++ | − | − |
| 22 | MUTK3 |  | S | Q | T | N | D | K | H | K | R | D | − | − | +++ | − | − |
| 36 | MUTK6 |  | S | Q | T | N | D | K | H | K | R | D | T | − | − | +++ | − | − |
| 35 | MUTK5 |  |  | Q | T | N | D | K | H | K | R | D | T | − | − | ++ | − | − |
| 33 | MUTK1 |  |  | Q | T | N | D | K | H | K | R | D | T | − | − | + | − | − |
| 37 | MUTK7 |  |  |  | T | N | D | K | H | K | R | D | T | ++ | +++ | +++ | − | − |

| | | HIL peptides | | | | | | | | | | MUT ||| MUT/MUR | MUR |
|---|---|---|---|---|---|---|---|---|---|---|---|---|---|---|---|---|
| | | | | | | | | | | | | #2 | #4 | TAP1 | #2 | #4 |
| 40 | Hil 2 | E | E | E | T | G | E | T | G | Q | L |  | − | − | − | − | − |
| 41 | Hil 3 |  | E | T | G | E | T | G | Q | L | V | H | − | − | − | − | − |

TABLE 15

Anti-MUT serum (TAP1) reactivity. Miltenberger negative cells were modified with the peptide-lipid constructs M22, M33, M34, M35, M36, M37, M40 and M41 at a concentration of 50 µg/ml (2 hours, 37° C.). Modified cells were tested against Taiwan Mi III antibody positive serum TAP1 to determine its MUT reactivity profile. TAP 1 (Taiwan Miltenberger antibody positive sample). The TAP1 serum is able to recognize some, but not all, peptide variations of MUT. The lack of reactivity with M40 and M41 (HIL peptide) modified cells and the untransformed cells is expected.

| | | MUT Peptides ||||||||||| Reactivity |
|---|---|---|---|---|---|---|---|---|---|---|---|---|---|
| 34 | MUTK4 | S | S | Q | T | N | D | K | H | K | R |  |  | 5 |
| 22 | MUTK3 |  | S | Q | T | N | D | K | H | K | R | D |  | 8 |
| 36 | MUTK6 |  | S | Q | T | N | D | K | H | K | R | D | T | 8 |
| 35 | MUTK5 |  |  | Q | T | N | D | K | H | K | R | D | T | 5 |
| 33 | MUTK1 |  |  | Q | T | N | D | K | H | K | R | D | T | 3 |
| 37 | MUTK7 |  |  |  | T | N | D | K | H | K | R | D | T | 8 |

| | | HIL peptides |||||||||||
|---|---|---|---|---|---|---|---|---|---|---|---|---|---|
| 40 | Hil 2 | E | E | E | T | G | E | T | G | Q | L |  |  | — |
| 41 | Hil 3 |  | E | T | G | E | T | G | Q | L | V | H | — |

TABLE 16

Anti-MUR serum (TAP1) reactivity. Miltenberger negative cells were modified with the peptide-lipid constructs M17, M19, M25, M26, M27, M28, M29, M30 and M31 at a concentration of 50 μg/ml (2 hours, 37° C.). Modified cells were tested against antibody positive serum #7 from the Miltenberger Antibody Positive Panel to determine their MUR reactivity profile.

|    |        |   |   |   |   |   |   |   |   |   |   |   |   | Panel Serum #7 (T8445) |
|----|--------|---|---|---|---|---|---|---|---|---|---|---|---|---|
| 30 | Mur 9  | D | T | Y | P | A | H | T | A | N | E |   |   | 8 |
| 17 | Mur 2  |   | T | Y | P | A | H | T | A | N | E | V |   | 10 |
| 28 | Mur 6  |   | T | Y | P | A | H | T | A | N | E |   |   | 8 |
| 27 | Mur 5  |   | T | Y | P | A | H | T | A | N |   |   |   | — |
| 25 | Mur 4  |   |   | Y | P | A | H | T | A | N | E |   |   | 3 |
| 26 | Mur 7  |   |   | Y | P | A | H | T | A | N | E | V |   | 10 |
| 31 | Mur 10 |   |   | Y | P | A | H | T | A | N | E | V | S | 8 |
| 19 | Mur 3  |   |   |   | P | A | H | T | A | N | E | V |   | 8 |
| 29 | Mur 8  |   |   |   | P | A | H | T | A | N | E | V | S | 8 |

TABLE 17

False positive MUT construct reactions with negative serums. The rate of false positive reactions was determined against a panel of 51 blood donor plasma samples (PAC1-51). Plasma were tested against cells modified with the peptide-lipid constructs M22, M34, M36, M37 and M40 of peptide-lipid constructs at a concentration of 50 μg/ml (2 hours, 37° C.) and tested in BioVue AHG cards. The amino acid sequence can influence the rate of false positive reactions. One more or less amino acid at either end of the polypeptide chain can increase the chances of non-specific reactions occurring with serum.

| PAC Samples No. | Reaction scores - BioVue AHG | | | | |
|---|---|---|---|---|---|
|  | M22 | M34 | M36 | M37 | M40 |
| 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 49, 50, 52, 53 | 0 | 0 | 0 | 0 | 0 |
| 47 | 0 | 0 | 3 | 0 | 0 |
| 48 | 0 | 3 | 5 | 0 | 0 |
| 51 | 0 | 5 | 0 | 0 | 0 |
| % False Positives | 0 | 3.8% | 3.8% | 0 | 0 |

|    |        |   |   |   |   |   |   |   |   |   |   |   | Reactivity |
|----|--------|---|---|---|---|---|---|---|---|---|---|---|---|
|    |        | MUT Peptides | | | | | | | | | | | |
| 34 | MUTK4  | S | S | Q | T | N | D | K | H | K | R |   | 3.8% |
| 22 | MUTK3  |   | S | Q | T | N | D | K | H | K | R | D | 0 |
| 36 | MUTK6  |   | S | Q | T | N | D | K | H | K | R | D | T | 3.8% |
| 37 | MUTK7  |   |   |   | T | N | D | K | H | K | R | D | T | 0 |
|    |        | HIL peptides | | | | | | | | | | | |
| 40 | Hil 2  | E | E | E | T | G | E | T | G | Q | L |   | 0 |

TABLE 18

False positive MUR M17 construct reactions with 102 negative serums. Cells modified with the peptide-lipid construct M17 were tested against 102 negative serum samples. Cells modified with the peptide-lipid construct M17 give the most "false positive" reactive construct showing up to 36% false positive rate with negative serums.

| False positive reactions with M17 | | | | |
|---|---|---|---|---|
| Score | 12-10 | 8-5 | 3 | 0 |
| (n = 102) | 17 | 18 | 3 | 65 |
|  | 17% | 18% | 3% | 64% |

TABLE 19

"M17-false-positive" negative serum reactivity against other Mur constructs. The 6 most false positive negative serums reactive against cells modified with the peptide-lipid construct M17 were tested against cells modified by contacting with the peptide-lipid constructs M19, M25, M26, M27, M28, M29, M30 and M31 at a concentration of 50 µg/ml (2 hour 37° C.). The modified cells were tested in BioVue™ AHG cards. Cell modified with the peptide-lipid construct M17 provided the most "false positive" reactions with negative serums. The reactivity of the 6 most false positive samples when tested against other modified cells shows that some are unreactive (M28, M27), some are poorly reactive or show a single discrete reactivity (M5, M29, M19) while others are more reactive (M31, M26). Minor changes in amino acid sequence can influence the rate of false positive reactivity. Cells modified with the constructs M30 and M28 show both specificity and low non-specificity.

T series reactives (n = 58)

| | 2 | 4 | 31 | 44 | 61 | 18 | 21 | 28 | 55 | 42 | 63 | 62 | 7 | 20 | 48 | 22 | 39 | 23 | 30 | % positive |
|---|---|---|---|---|---|---|---|---|---|---|---|---|---|---|---|---|---|---|---|---|
| M17 | 10 | 8 | 8 | 10 | 10 | 12 | 12 | 12 | 12 | 10 | 10 | 8 | 8 | 8 | 8 | 8 | 5 | 3 | 3 | 33% |
| M28 | 10 | 8 | 8 | 10 | 10 | 0 | 0 | 0 | 0 | 0 | 0 | 0 | 0 | 0 | 0 | 0 | 0 | 0 | 0 | 9% |
| M30 | 10 | 8 | 8 | 10 | 10 | 0 | 0 | 0 | 0 | 0 | 0 | 0 | 0 | 0 | 0 | 0 | 0 | 0 | 0 | 9% |

39 T negative samples were negative with all 3 constructs.

Larger series = 102

| | | | | | | | | | | | | T18 | T21 | T28 | T55 | T78 | T92 |
|---|---|---|---|---|---|---|---|---|---|---|---|---|---|---|---|---|---|
| 30 Mur 9 | D | T | Y | P | A | H | T | A | N | E |   | — | — | — | — | — | — |
| 17 Mur 2 |   | T | Y | P | A | H | T | A | N | E | V | 12 | 12 | 12 | 12 | 12 | 12 |
| 28 Mur 6 |   | T | Y | P | A | H | T | A | N | E |   | — | — | — | — | — | — |
| 27 Mur 5 |   | T | Y | P | A | H | T | A | N |   |   | — | — | — | — | — | — |
| 25 Mur 4 |   |   | Y | P | A | H | T | A | N | E |   | — | — | — | — | 5 | — |
| 26 Mur 7 |   |   | Y | P | A | H | T | A | N | E | V | 5 | 10 | 12 | 10 | 10 | 12 |
| 31 Mur 10 |   |   | Y | P | A | H | T | A | N | E | V S | — | 10 | 12 | — | 8 | 12 |
| 19 Mur 3 |   |   |   | P | A | H | T | A | N | E | V | — | — | — | 12 | — | — |
| 29 Mur 8 |   |   |   | P | A | H | T | A | N | E | V S | — | — | 5 | — | — | 8 |

5 samples reacted with all 3 constructs

| | | | | | | | | | | | | Panel Serum #7 (T8445) | False Positivity |
|---|---|---|---|---|---|---|---|---|---|---|---|---|---|
| 30 Mur 9 | D | T | Y | P | A | H | T | A | N | E |   | 8 | - |
| 17 Mur 2 |   | T | Y | P | A | H | T | A | N | E | V | 10 | +++ |
| 28 Mur 6 |   | T | Y | P | A | H | T | A | N | E |   | 8 | - |
| 27 Mur 5 |   | T | Y | P | A | H | T | A | N |   |   | — | - |
| 25 Mur 4 |   |   | Y | P | A | H | T | A | N | E |   | 3 |   |
| 26 Mur 7 |   |   | Y | P | A | H | T | A | N | E | V | 10 | +++ |
| 31 Mur 10 |   |   | Y | P | A | H | T | A | N | E | V S | 8 | ++ |
| 19 Mur 3 |   |   |   | P | A | H | T | A | N | E | V | 8 | + |
| 29 Mur 8 |   |   |   | P | A | H | T | A | N | E | V S | 8 | + |

TABLE 20

Sera reactive with RBCs modified to incorporate the M1 peptide-lipid construct or M2 peptide-lipid construct constructs by contacting the cells with a 500 µg/ml dispersion of the construct (Method 1) were "neutralised" with the peptide QTNDKHKRDTY and retested against the modified cells. Sera were neutralized by adding 10 µL of 1 mg/ml solution of peptide to a 50 µL volume of sera and incubating for 30 minutes at 37° C. Testing was performed using BioVue™ cards.

| | M1 modified cells | | | M2 cells vs serum | | |
|---|---|---|---|---|---|---|
| Identity of sera | #4 | #5 | #6 | #2 | #6 | #8 |
| Serum alone | 5 | 5 | 10 | 8 | 8 | 8 |
| Serum + peptide | 0 | 0 | 0 | 0 | 2 | 0 |

TABLE 21

Sera reactive with RBCs modified to incorporate the M13 peptide-lipid construct by contacting the cells with a 500 µg/ml dispersion of the construct (Method 1) were "neutralised" with the peptide SSQTNDKHKRDTY and retested against the modified cells. Sera were neutralized by adding 10 µL of 1 mg/ml solution of peptide to a 50 µL volume of sera and incubating for 30 minutes at 37° C. Testing was performed using BioVue™ cards.

| | M13 modified cells | | | |
|---|---|---|---|---|
| Identity of sera | #3 | #42 | #37 | #34 |
| Serum alone | 8 | 8 | 8 | 8 |
| Serum + peptide | 0 | 0 | 0 | 0 |

TABLE 22

Cells were modified by the peptide-lipid construct M22 (2 hours, 37° C.) and two positive reactions were identified. Neutralisation experiments were then performed. A volume of 40 µl of plasma was incubated with 10 µl of peptide or Ac—C at a concentration of 1.0 mg/ml for 30 minutes at 37° C. The standard AHG test in BioVue ™ was then performed. The false positive reaction for PAC74 was confirmed as a reaction not neutralised by addition of peptide. The true positive reaction for TAP1 confirmed as reaction neutralised by peptide and the whole construct, but not the construct bearing only acetylated cysteine.

| | | | PAC74 | TAP1 |
|---|---|---|---|---|
| Pre-neutralisation serology (cells modified with the peptide-lipid construct M22) | | | 8 | 8 |

| Neutraliser | F | Linker | Post-neutralisation serology (cells modified with the peptide-lipid construct M22) | |
|---|---|---|---|---|
| nil | nil | nil | 8 | 8 |
| M22 peptide | SQTNDKHKRDC | nil | 8 | — |
| M28 peptide | TYPAHTANEC | nil | 8 | 8 |
| M22 molecule | SQTNDKHKRDC | CMG(2) | — | — |
| Cys-CMG-DE | Ac—C | CMG(2) | — | 8 |
| | VMYASSG? | | 8 | 8 |

TABLE 23

Cells were modified by the peptide-lipid construct M28 (2 hours, 37° C.) and four positive reactions were identified. Neutralisation experiments were then performed. A volume of 40 µl of plasma was incubated with 10 µl of peptide or Ac—C at a concentration of 1.0 mg/ml for 30 minutes at 37° C. The standard AHG test in BioVue ™ was then performed. The neutralisations of PAC70, 71 and 72 with the M28 peptide suggests specificity. The fact that the unrelated peptide M22 was also able to cause neutralisation of serums PAC71 and PAC72, together with reductions in score with other unrelated structures, revises the results for these two sera as being false positive reactivity. The fact that PAC70 does not react with Miltenberger positive cells suggests that although an antibody appears to be present to the peptide sequence it is not blood group specific. In contrast although TAP2 was not fully inhibited by peptide, the substantial reduction in score suggests specificity, although it is possible that specificity may be present with a low level of non-specificity as suggested by the reaction score reduction against Cys-CMG-DE.

| | | | PAC70 | PAC71 | PAC72 | TAP2 |
|---|---|---|---|---|---|---|
| Pre-neutralisation serology (cells modified with the peptide-lipid construct M28) | | | 8 | 5 | 5 | 8 |

| Neutraliser | F group | Linker | Post-neutralisation serology (cells modified with the peptide-lipid construct M22) | | | |
|---|---|---|---|---|---|---|
| saline | nil | nil | 8 | 5 | 5 | 8 |
| M22 peptide | SQTNDKHKRDC | nil | 8 | — | — | 3 |
| M28 peptide | TYPAHTANEC | nil | — | — | — | 8 |
| Cys-CMG-DE | Ac—C | CMG(2) | 8 | 3 | 3 | 5 |
| Atri-CMG-DE | GalNAcα3[Fucα2]Galβ | CMG(2) | 8 | 3 | 5 | 8 |
| Atri-adipate-DE | GalNAcα3[Fucα2]Galβ | adipate | 8 | 3 | 5 | 8 |
| | VMYASSG? | | 8 | 5 | 5 | 8 |

Consideration of the MUT peptide reactivities presented in the foregoing in Tables shows that peptides M22, M36 and M37 all showed superior sensitivity and specificity towards a human polyclonal antibody panel when compared with sequence 1, the sequence identified in the prior art (Reid and Lomas-Francis (2004)).

Modification of Red Blood Cells with Peptide-Lipid Constructs with Peptide in Alternative Configurations Peptide-lipid constructs comprising CMG(2) and the following peptides were prepared:

```
ThrTyrProAlaHisThrAlaAsnGluCys (M44)
and

CysThrTyrProAlaHisThrAlaAsnGlu (M45)
```

The termini of the peptides were formylated and amidated to provide "capped" peptides. The reactivity of random Miltenberger antibody positive samples and three false positive antibody negative samples were tested against RBCs modified to incorporate these "capped" peptide-lipid constructs (50 µg/mL, 2 hours at 37° C.).

The reactivity was assessed and recorded in Table 24. The capping of the peptide did not affect reactivity with positive samples, nor did it appear to affect reactivity with false-positive antibody-negative samples. However, linkage of the peptide via a Cys residue located at the amino terminus (as opposed to the carboxy terminus) appeared to reduce the likelihood of reactivity with the false-positive antibody negative samples and improve reactivity with the known antibody positive samples.

Whilst not wishing to be bound by theory it is speculated that the presentation of the peptide by cells modified to incorporate M45 may be more analogous to the presentation of the corresponding peptide sequence expressed by the naturally occurring antigen.

TABLE 24

| | Sample | M44 | M45 | Not modified | Natural MiIII cells |
|---|---|---|---|---|---|
| Antibody positive serums | 71 | 10 | 10 | 0 | 8 |
| | 67 | 8 | 10 | 0 | 5 |
| | 65 | 10 | 8 | 0 | 12 |
| | 55 | 8 | 8 | 0 | 10 |
| | 61 | 8 | 5 | 0 | 8 |
| | 942-433813-3 | 0 | 5 | 0 | 12 |
| | 68 | 0 | 0 | 0 | 10 |
| False-positive antibody negative serums | PAC302 | 5 | 0 | 0 | 0 |
| | PAC332 | 12 | 0 | 0 | 0 |
| | PAC340 | 5 | 0 | 0 | 0 |

Modification of Cells and Multi-Cellular Structures with Biotin-Lipid Constructs The modification of red blood cells (RBCs) and murine embryos by the construct designated Biotin-CMG(2)-Ad-DOPE was demonstrated using Avidin-Alexafluor (Avidin AF).

Materials

A stock solution of the construct designated Biotin-CMG(2)-Ad-DOPE (100 µL) was prepared in water at a concentration of 10 mg/mL. A stock solution of Avidin-Alexafluor (Avidin-AF) was prepared in sterile phosphate buffered saline (PBS) at a concentration of 2 mg/mL. A stock solution of biotinylated gangliocide (BioG) was prepared in sterile PBS at a concentration of 5 mg/mL.

Red Blood Cells

Dilution series of the construct designated Biotin-CMG(2)-Ad-DOPE and BioG (positive control) were prepared at concentrations of 0.001, 0.1, 0.1 and 1 mg/mL with Celpresol™. 0 group red blood cells (RBCs) were modified by incubation of 15 µL of packed RBCs and 5 µL of a dilution of the construct designated biotin-CMG(2)-Ad-DOPE or BioG. Incubations were performed in a plastic ependorf tube of nominal volume 1.5 mL for 2 hours at 37° C. in a water bath. O group RBCs were incubated with a solution of BioG at a concentration of 0.33 mg/mL as a positive control.

Incubated RBCs were washed 3 times with PBS in a mini centrifuge. Fluorescent labeling of the washed, modified RBCs was performed by adding 10 µL of a solution of Avidin-AF at a concentration of 0.1 mg/mL. The RBCs were then incubated in the dark for 1 hour at 37° C. in a water bath and washed 3 times with PBS.

Figure 6:
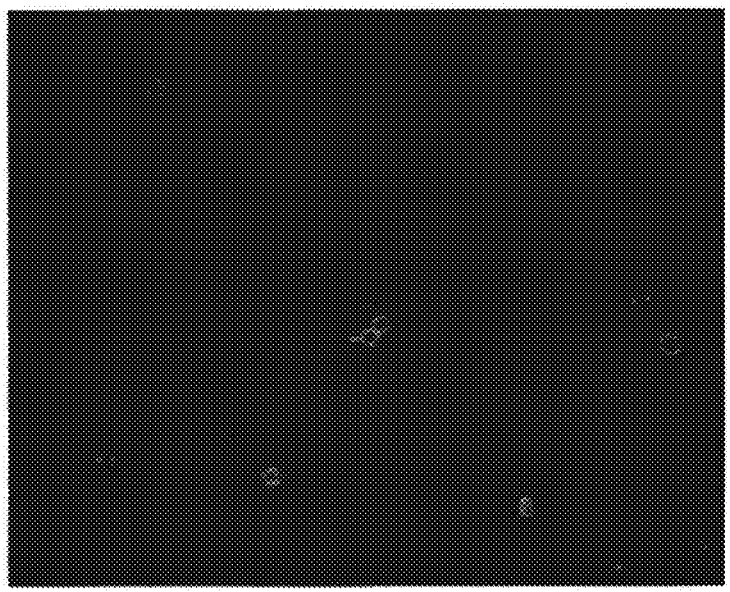
FIG. 6. Fluorescence microscopy of avidin AF labelled red blood cells modified with the construct designated Biotin-CMG(2)-Ad-DOPE (I) (1 mg/mL) and stored for 14 days.
Figure 7:
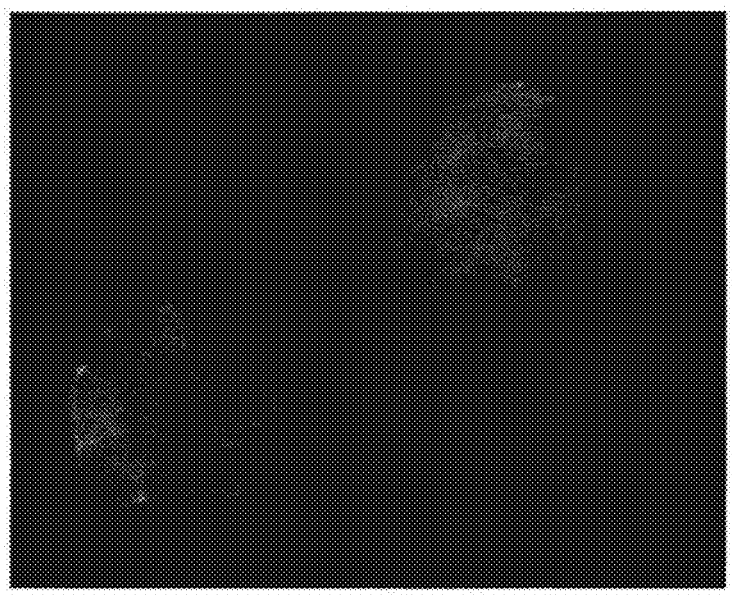
FIG. 7. Fluorescence microscopy of avidin AF labelled zona-free D3.5pc murine embryos modified with the construct designated Biotin-CMG(2)-Ad-DOPE (I) (0.1 mg/mL) (400× magnification).
Figure 8:
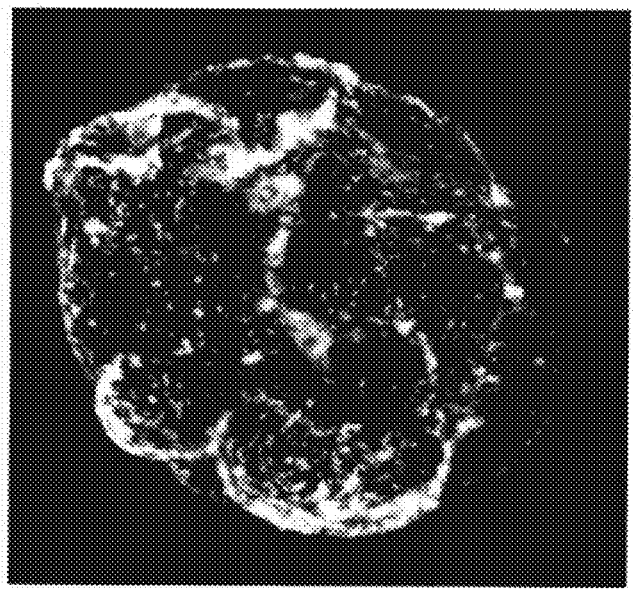
FIG. 8. Fluorescence confocal microscopy of an avidin AF labelled Biotin-CMG(2)-Ad-DOPE (I) modified murine embryo.

85% solution of the washed, fluorescent labeled RBCs were viewed on a slide with cover slip under a fluorescent microscope at 488 nm and photographic exposure of 1.903 (FIG. 6). The intensity of the fluorescent signal was recorded using a scoring system of 0 (no fluorescence observed) to 4 (maximum fluorescence observed).

An aliquot of the washed, modified RBCs obtained from incubation with the construct designated biotin-CMG(2)-Ad-DOPE at a concentration of 1 mg/mL was retained and stored at 14° C. for 14 days. Retention of the construct by the RBCs was assessed by incubation with Avidin-AF as before.

The assessment of the fluorescence is recorded in Table 25.

TABLE 25

| Dilution (mg/ml) | 1 | 0.1 | 0.01 | 0.001 | 0 |
|---|---|---|---|---|---|
| Biotin-CMG(2)-Ad-DOPE Day 0 | 4 | 2 | 1 | 0 | 0 |
| Biotin-CMG(2)-Ad-DOPE Day 14 | 4 | — | — | — | — |
| BioG Day 0 | 3 | 2 | 0 | 0 | 0 |

Murine Embryos

Murine embryos (morula/early blastocyst stage, 3.5 day) were incubated in 50 microlitre microdrops in Blastassist™ culture media. Embryos were incubated with construct designated biotin-CMG(2)-Ad-DOPE at a concentration of 0.1, 1 or 2 mg/mL or BioG at a concentration of 0.5 mg/ml, (positive control).

The zona pellucida of the embryos was removed by treatment with 0.5% pronase (4 minute incubation) and washing 3 times in embryo handling media prior to introduction into the microdrops. Each microdrop was equilibrated 5% $CO_2$ at 37° C. overnight prior to introduction of the embryos.

Microdrops containing embryos and the construct designated biotin-CMG(2)-Ad-DOPE were incubated for 2 hours in 5% $CO_2$ at 37° C. Microdrops containing embryos and BioG were incubated for 40 minutes in 5% $CO_2$ at 37° C.

Following incubation each group of embryos was washed 3 times in handling media and transferred to 50 microlitre microdrops containing 2 mg/ml, Avidin-AF microdrops for fluorescent labelling. The microdrops containing transferred embryos were incubated at 37° C. for 30 minutes in the dark.

Each group of embryos was then washed 3 times in handling media and mounted on a glass microscope slide for viewing. Embryos were viewed under a fluorescent microscope at 488 nm. The intensity of the fluorescence was recorded using a scoring system of 0 (no fluorescence) to 4 (maximum fluorescence).

TABLE 26

| Biotin-CMG(2)-Ad-DOPE 0.1 mg/mL | Biotin-CMG(2)-Ad-DOPE 1 mg/mL | Biotin-CMG(2)-Ad-DOPE 2 mg/mL | BioG 0.5 mg/mL | Media alone |
|---|---|---|---|---|
| 2 | 1 | 1 | 3 | 1 |
| n = 21 | n = 19 | n = 19 | n = 19 | n = 19 |

Immobilization of Spermatozoa and Cells

The immobilization of spermatozoa and red blood cells (RBCs) was demonstrated by use of the construct designated Biotin-CMG(2)-Ad-DOPE and streptavidin beads (Dynabeads® M-280).

Materials

A stock solution of the construct designated Biotin-CMG(2)-Ad-DOPE (100 µL) was prepared in water at a concentration of 10 mg/mL and diluted in culture media (Medicult 10310060A) to provide a test dilution at 0.1 mg/mL.

The spermatozoa in fresh semen (less than one day old) were assessed for motility (80%, grade 3 (fast, forward progression) by 10-fold dilution in culture medium (Medicult 10310060A; pre-incubated for a minimum of 2 hours at 37° C. in a 5% $CO_2$ atmosphere). Spermatozoa counts ($91.5 \times 10^6$/mL) were performed by 10-fold dilution in deionised water.

Spermatozoa were washed and isolated by layering 1.1 mL of fresh semen over a gradient of SpermGrad 125 (Vitrolife 10099; 2 mL of 40% solution over 2 mL of 80% solution in a 15 mL round bottom tube) and centrifuging at 500×g for 20 min.

The bottom layer of the gradient (c. 0.7 mL was transferred to 4 mL round bottom tubes and c. 2 mL flushing (handling) media (Medicult 10840125A) added. The tube was centrifuged at 300×g for 10 min and the spermatozoa washed two more times (mixing by tube inversion).

Samples of washed spermatozoa were incubated overnight at 37° C. in a 5% $CO_2$ atmosphere. Spermatozoa counts (c. $25 \times 10^6$/mL) were performed post overnight incubation by 10-fold dilution in deionised water.

Spermatozoa

A volume of 100 µl of the test dilution of the construct designated Biotin-CMG(2)-Ad-DOPE (I) was added to each of four 0.6 mL ependorf tubes (A-D) and 100 µL of culture media added to one 0.6 mL ependorf tube (E).

Open tubes were incubated at 37° C. in a 5% $CO_2$ atmosphere prior to addition of c. 70 µL spermatozoa (c. $25 \times 10^6$/mL) to each tube and incubation for 120 min (A), 60 min (B), 30 min (C), 10 min (B) and 120 min (E).

Following incubation a couple of drops of flushing media were added and the tubes centrifuged at 300×g for 5 min. The spermatozoa were washed two more times with flushing media and before being re-suspended in culture media to a final volume of 100 µL.

Streptavidin beads at a concentration of c. $6.25 \times 10^6$/100 µL were diluted 35 times in BSA plus flushing media to provide a ratio of 0.1 beads/spermatozoa when mixed in equal volume with a diluted suspension of the modified spermatozoa.

A volume of 5 µL of a diluted suspension of the modified spermatozoa was mixed on a slide with 5 µL of a diluted suspension of streptavidin beads and covered with a coverslip.

Figure 9:
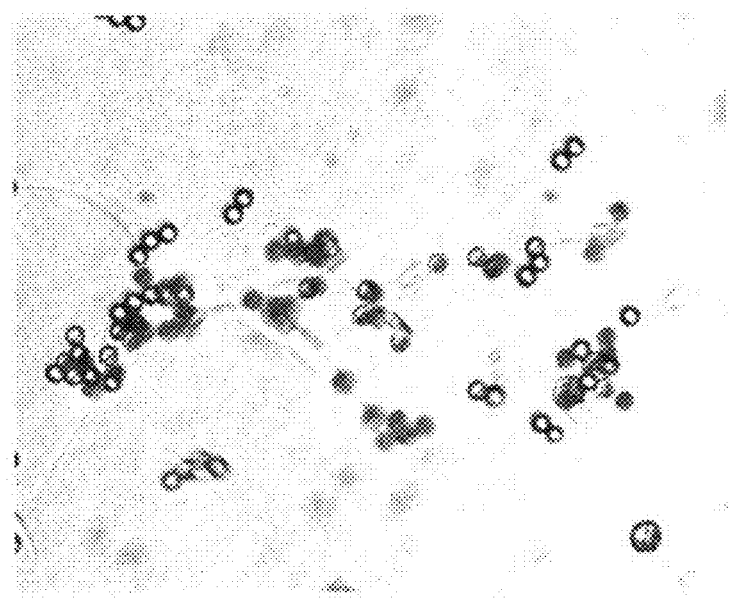
FIG. 9. Attachment of streptavidin beads to spermatozoa following modification of the spermatozoa by incubation with the construct designated Biotin-CMG(2)-Ad-DOPE (I).

The mixture was observed under a microscope at 400× magnification. FIG. 9 provide a photomicrograph of the mixture provided following incubation with 0.1 mg/mL of the construct designated Biotin-CMG(2)-Ad-DOPE for 60 min (B).

The assessment of the attachment of streptavidin beads to modified spermatozoa is recorded in Table 27.

TABLE 27

| Biotin-CMG(2)-Ad-DOPE (I) treatment | Incubation time (min) | Number of beads attached to spermatozoa | |
|---|---|---|---|
| | | Immediate | 30 min |
| A | 120 | 10-12 | 10-15 (with cross-linking) |
| B | 460 | 2, 4, 8 | 8 |
| C | 30 | 1-3 | 3 |
| D | 10 | 1 | 1 |
| E (Control) | 120 | 0 | 0 |

Spermatozoa were observed to retain motile capacity despite attachment of beads (no acrosome reaction was evident) with a preference of attachment to motile spermatozoa.

Red Blood Cells

A dilution of the construct designated Biotin-CMG(2)-Ad-DOPE was prepared at a concentration of 1 mg/mL with Celpresol™. A volume of 60 µL washed A group red blood cells (RBCs) was modified by incubation with 20 µL of the dilution of the construct at 37° C. for 2 hours.

The modified RBCs were washed twice in PBS and once in Celpresol™ as described above. A 2% cell suspension of washed cells (modified or control) was prepared in Celpresol™ and cell concentration ($150 \times 10^6$/mL) determined using a haemocytometer. Similarly the concentration of a suspension streptavidin beads ($134 \times 10^6$/mL) was determined.

A volume of 50 µL of the suspension of streptavidin beads was added to the wells of a 96-well plat with a Neodymium (Rare-Earth) Super magnet (Magnets NZ Limited) affixed to the base. A volume of 50 µL of a suspension of RBCs was added to provide a bead to RBC ratio of c. 1:1 and incubated at room temperature for 1 hour to allow RBCs to settle.

Figure 10:
FIG. 10. Retention by streptavidin beads of following modification of the RBCs by incubation with the construct designated Biotin-CMG(2)-Ad-DOPE (I).
Figure 11:
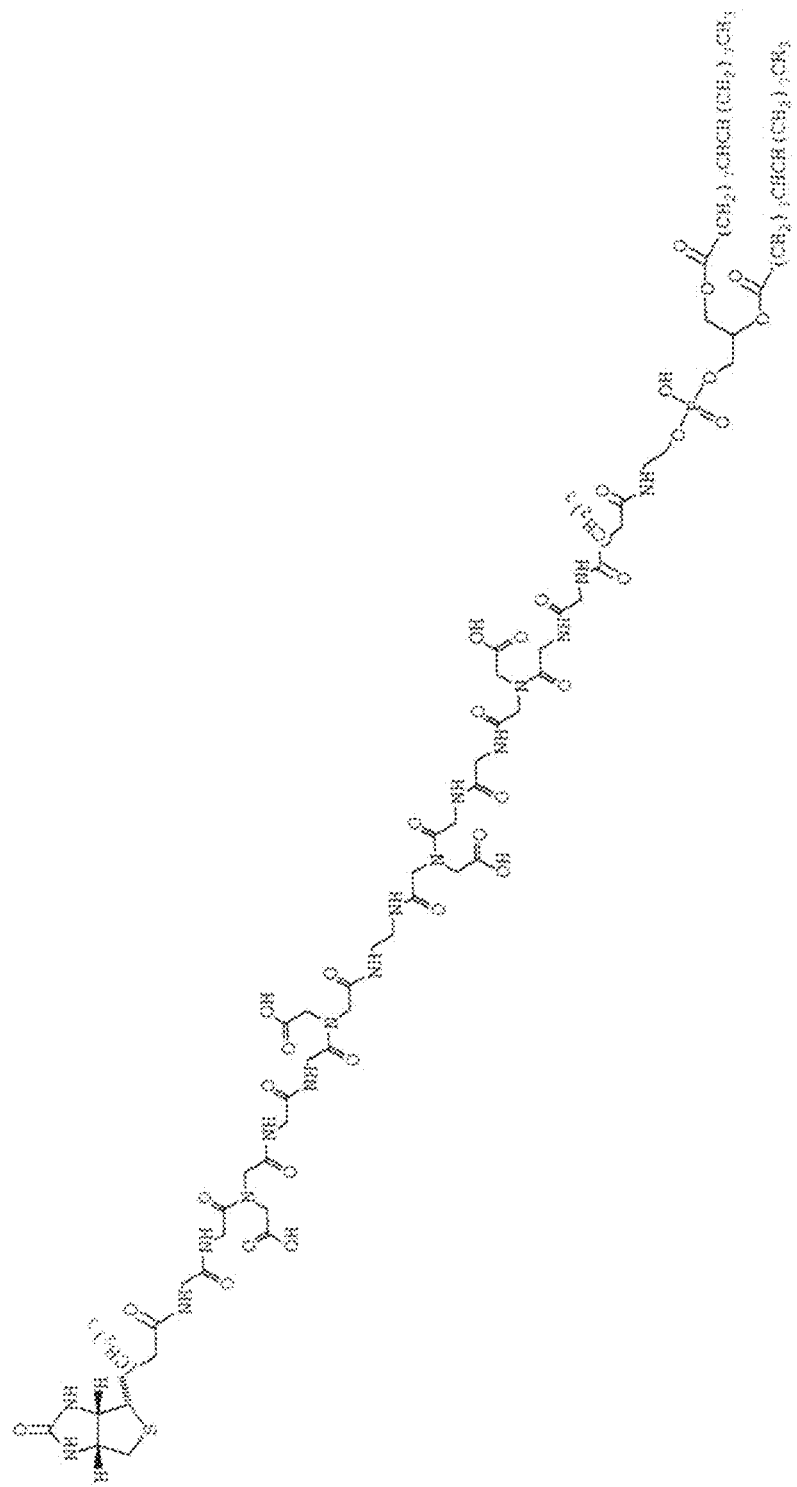
FIG. 11. Structure of the construct designated Biotin-CMG(2)-Ad-DOPE.

The wells were washed 3× with PBS, aspirating the washing solution with a pipette. The washed wells were observed under a microscope and the RBCs determined to be retained (FIG. 10).

Separation of Populations of Cells

A 0.5 mg/ml solution of the construct designated Biotin-CMG(2)-Ad-DOPE was prepared in Celpresol™ and a volume of 10 µl used to modify 30 µl packed cell volume of group 0 RBCs in a 1 ml eppendorf tube to provide a first population of cells. Unmodified group A RBCs were used as a second population of cells.

Both populations of cells were incubated for 37° C. for 2 hrs in a water bath and then washed 2× in PBS and 1× in Celpresol using an Immufuge II (low, 1 min). The concentration of cells in each suspension was made up to 2% by adding 1.5 mL.

The suspensions of RBCs were mixed with avidinylated magnetic Dynabeads at an approximate ratio of RBC:bead of 1 and incubated for 10 min at room temperature on a gyrator. Samples of the first and second populations of RBCs were then mixed in equal volumes (35 µl each) in an ependorf tube for two minutes.

The contents of the ependorf were transferred to the well of a 96-well plate and a magnet was applied to the underside of the well for 1 minute. The supernatant was carefully removed with the magnet applied and without disruption of the beads. The blood grouping of the cells of the supernatants were then assessed by applying 30 µl of supernatant and 30 µl anti-A antibody to a Dynamed™ gel card. Cards were spun for 10 min in a centrifuge. Retention of the 0 group RBCs by the magnet was demonstrated by the absence of a pellet of group 0 cells.

Modification of Cell Layers with Biotin-Lipid Constructs

The modification of monolayers of the cell line RL95-2 (established from a human endometrial adenocarcinoma (ATCC HTB CRL 1671)) in serum-free and serum-containing media was evaluated.

D-MEM/F12 (Gibco 11320-033, Invitrogen NZ) containing 1% penicillin/streptomycin (Gibco 15140-122, Invitrogen NZ) was used as a serum-free medium. D-MEM/F12 10% FBS (Gibco 10091-130, Invitrogen NZ) containing 1% penicillin/streptomycin and 5 pg/mL insulin (Gibco 12585-014, Invitrogen NZ) was used as a serum-containing medium.

A suspension of the cell line RL95-2 was diluted in pre-warmed serum-containing media to the required concentration e.g. $4 \times 10^5$ cells/mL. A 25 μL volume of the suspension was used to seed the required wells in a Terasaki tray so that each treatment was performed in duplicate. The plates were incubated overnight in a 5% $CO_2$, 37° C. incubator until the monolayer was approximately 60% confluent.

Dilutions of Biotin-CMG(2)-Ad-DOPE were prepared and 12 μl volumes added to wells containing washed cell layers to provide final concentrations of 20, 100 or 500 pg/mL. Trays were incubated at 37° C., 5% $CO_2$ for 120 min.

The cells were then washed and a 12 μl volume of a 0.1 mg/mL solution of Avidin Alexa Fluor® 488 added. The cells were then incubated at room temperature for a further 30 minutes in the dark.

Figure 12:
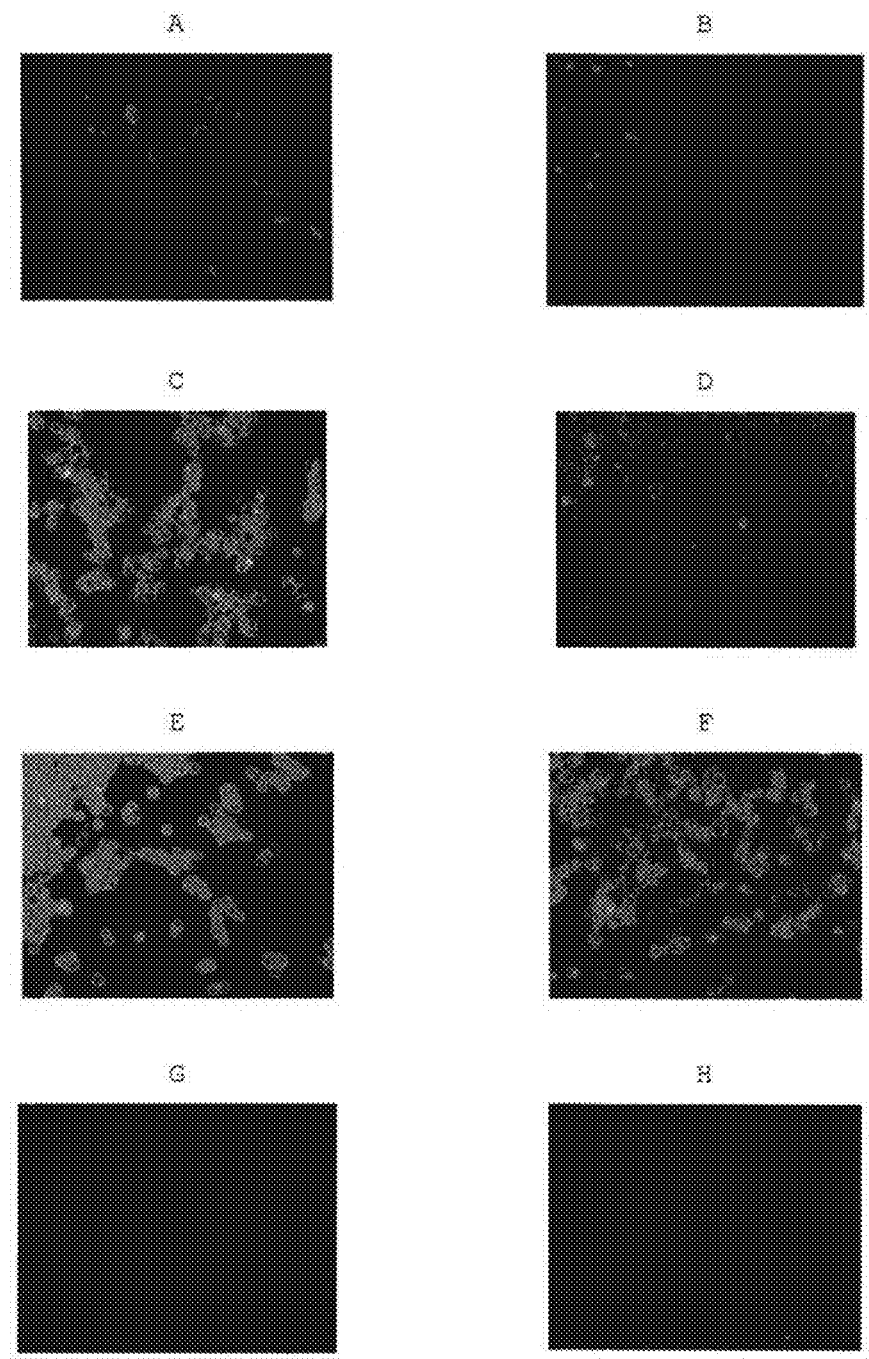
FIG. 12. RL95-2 monolayers modified with 20, 100 and 500 pg/mL biotin-CMG(2)-Ad-DOPE or media alone in serum-free media (A, C, E and G) and serum-containing media (B, D, F and H).

The monolayers were finally washed 3 times with PBS, the trays inverted and photographed using an Olympus BX51 fluorescent microscope at 200× magnification, exposure time 475 ms (FIG. 12).

When the construct is inserted in serum-free media at 20, 100 and 500 μg/mL, a homogenous intense fluorescent signal is observed in the cell membrane that intensifies with increasing concentration of the construct (FIGS. 12A, C and E). When the construct is inserted in serum-containing media, weakened fluorescence is observed at the same concentrations (FIGS. 12B, D and F). These results imply that optimal insertion of construct into the cell membranes requires serum-free media.

When the construct is inserted in serum-free media at 20, 100 and 500 μg/mL, an homogenous intense fluorescent signal is observed in the cell membrane that intensifies with increasing concentration of construct. The intensity of the fluorescence also increased with increasing insertion time (Table 28).

These results imply that optimal insertion of construct into cell membranes occurs with increased concentration of construct and/or increased insertion time.

TABLE 28

Optimal insertion of construct into cell membranes occurs with increased concentration of construct and/or increased insertion time.

| Concentration of biotin- | Mean Fluorescence* Insertion time | | | |
|---|---|---|---|---|
| CMG(2)-Ad-DOPE (μg/mL) | 10 | 30 | 60 | 120 |
| 20 | 1+ | 1-2+ | 2-3+ | 3-4+ |
| 100 | 2+ | 3 | 3+ | 4+ |
| 500 | 3+ | 3-4+ | na | na |
| Media alone | 0 | 0 | 0 | 0 |

'na' denotes "not assessed".

Figure 13:
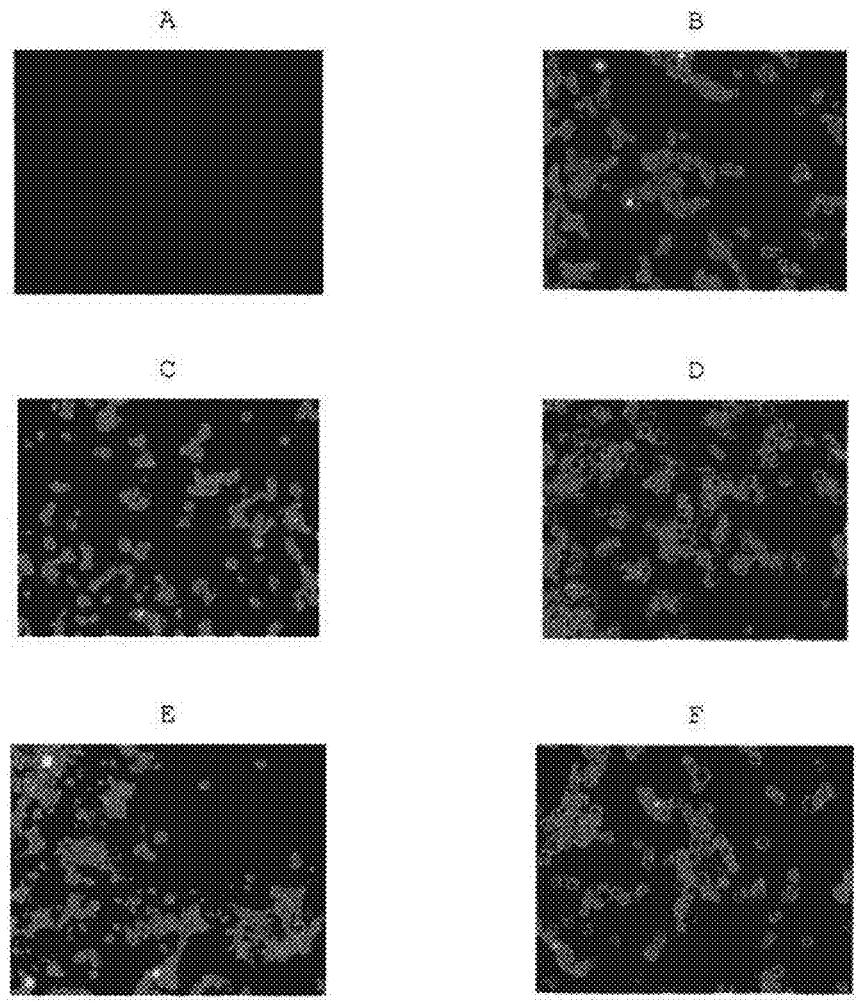
FIG. 13. Addition of Avidin Alexa Fluor® 488 to RL95-2 monolayers modified with biotin-CMG(2)-Ad-DOPE. Fluorescence microscopy images of cells after addition of Avidin Alexa Fluor® 488 incubated at 37° C. show fluorescence starts to internalize within 4 hr (C) and is present in the cell interior in 24 hr (E). No internalization was observed when cells were incubated at 4° C. (D, F).

When avidin Alexa Fluor® 488 was added to construct modified RL95-2 cells and incubated at 37° C. for 4 and 24 hr the fluorescence gradually shifted from the cell surface to the cell interior (FIG. 13). No internalization was observed when cells were incubated at 4° C.

Fluorescence was detected in construct modified RL95-2 cells 24 hr post-insertion when cultured in serum-free media, albeit with reduced fluorescence from T=0 (Table 29). However, when cells were cultured in serum-containing media a fluorescence score of 1+ was detected at the highest concentration of construct (500 mg/mL), but not at lower. These results imply that the construct is optimally retained in cell membranes 24 hr post-insertion when cultured in serum-free media, but not in serum-containing media.

TABLE 29

Retention of construct 24 hours post-insertion. The construct was detected in cells cultured for 24 hr post-insertion in serum-free media, but was only detected at the highest concentration in serum-containing media.

| Concentration of biotin- | Mean Fluorescence* | | |
|---|---|---|---|
| CMG(2)-Ad-DOPE | | T = 24 hr | |
| (μg/mL) | T = 0 | Serum-free | Serum-containing |
| 20 | 3-4+ | 1-2+ | 0 |
| 100 | 4+ | 2-3+ | 0 |
| 500 | | 4+ | 1+ |
| Media alone | 0 | 0 | 0 |

'na' denotes "not assessed".

Modification of Antigen Presentation

The amount of construct used in the manufacture of quality controls cells as described in the specification accompanying international application no. PCT/NZ2005/000052 (publication no. WO 2005/090368) is a determinant of the cost of manufacture.

It was anticipated that presentation of antigen at a distance from the immediate milieu of the cell surface may promote recognition by cross-reactive antibody and subsequent agglutination. The estimated distances from the cell surface for an antigen (F) of a functional lipid construct (F-S-L) where the spacer (S) includes the structural motif of the present invention are 7.2 nm (CMG(2)) and 11.5 nm (CMG(4)). These distances compare with 1.9 nm for the antigen of a construct (F-S-L) where the spacer is one described in the specification accompanying international application no. PCT/NZ2005/000052 (publication no. WO 2005/090368), i.e. $A_{tri}$-sp-Ad-DOPE (I).

To test the hypothesis solutions of four different trisaccharide ($A_{tri}$)-lipid constructs were prepared as 50 μM, 10 μM and 5 μM solutions in Celpresol™. Modified red blood cells were then prepared by contacting 0.6 mls (pcv) of washed RBCs with 0.6 mls of the relevant solution. The mixtures were incubated at 37° C. for 2 hours and then washed 3 times to provide a modified cell suspension.

The modified cell suspensions were prepared in 0.8% in Celpresol LISS™ suitable for BioVue serology cards. A volume of 0.05 mls of CSL monoclonal anti-A (026129801) followed by 0.05 mls of modified cell suspension was applied to each card. Reactions were recorded following centrifugation in a BioVue cassette centrifuge (Table 29).

A comparison of the recorded reaction for molar equivalents of the $A_{tri}$-lipid constructs demonstrates that less CMG(2) or CMG(4) construct is required to provide an equivalent serological result. There was no significant gain with CMG(2) compared with CMG(4). There was a minor, but not significant change for MCMG (2).

Although the invention has been described by way of examples it should be appreciated that variations and modifications may be made to the claimed methods without departing from the scope of the invention. As noted it will be understood that for a non-specific interaction, such as the interaction between the diacyl- or dialkyl-glycerolipid portion of the functional-lipid constructs and a membrane, structural and stereo-isomers of naturally occurring lipids can be functionally equivalent.

Where known equivalents exist to specific features, such equivalents are incorporated as if specifically referred to in this specification. For example, it is contemplated that diacylglycerol 2-phosphate could be substituted for phosphatidate (diacylglycerol 3-phosphate) and that the absolute configuration of phosphatidate could be either R or S.

TABLE 30

A_tri-lipid construct

| Structural motif of spacer | Conc (µM) | Serological result at reciprocal of dilution of anti-A | | | | | | | | | | |
|---|---|---|---|---|---|---|---|---|---|---|---|---|
| | | Neat | 2 | 4 | 8 | 16 | 32 | 64 | 128 | 256 | 512 | 1024 | 0 |
| Adipate | 50 | 12 | 12 | 12 | 12 | 12 | 12 | 10 | 8 | 8 | 3 | — | — |
| | 10 | 10 | 10 | 10 | 8 | 8 | 8 | 8 | 3 | — | — | — | — |
| | 5 | 8 | 8 | 5 | 3 | — | — | — | — | — | — | — | — |
| CMG(2) | 50 | 12 | 12 | 12 | 12 | 12 | 12 | 10 | 10 | 8 | 5 | 3 | — |
| | 10 | 12 | 12 | 12 | 10 | 10 | 10 | 10 | 8 | 5 | 3 | — | — |
| | 5 | 10 | 10 | 10 | 10 | 8 | 8 | 8 | 5 | 3 | — | — | — |
| mCMG(2) | 50 | 12 | 12 | 12 | 12 | 12 | 12 | 12 | 10 | 10 | 8 | 5 | — |
| | 10 | 12 | 12 | 12 | 12 | 12 | 10 | 10 | 8 | 8 | 5 | — | — |
| | 5 | 10 | 10 | 10 | 10 | 10 | 8 | 8 | 5 | 3 | — | — | — |
| CMG(4) | 50 | 12 | 12 | 12 | 12 | 12 | 12 | 10 | 10 | 8 | 5 | 3 | — |
| | 10 | 12 | 12 | 12 | 10 | 10 | 10 | 10 | 8 | 8 | 3 | — | — |
| | 5 | 10 | 10 | 10 | 10 | 8 | 8 | 8 | 5 | 3 | — | — | — |

REFERENCES

Audibert et al (1987) Conjugates of haptenes and muramyl-peptides, endowed with immunogenic activity and compositions containing them U.S. Pat. No. 4,639,512.

Blume et al (1993) Specific targeting with poly(thylene glycol)-modified liposomes coupling of homing devices to the ends of the polymeric chains combines effective target binding with long circulation times. Biochimica et Biophysica Acto, 1149: 180-184

Bovin et al (1993) Synthesis of polymeric neoglycoconjugates based on N-substituted polyacrylamides Glycoconjugate Journal 10, 142-151.

Bovin et al (2005) Synthetic membrane anchors International application no. PCT/NZ2005/000052 (publ. no. WO 2005/090368).

Carter et al (2007) Cell Surface Coating with Hyaluronic Acid Oligomer Derivative International application no. PCT/NZ2006/000245 [publ. no. WO 2007/035116].

Chung et al (2004) Casual Cell Surface Remodelling Using Biocompatible Lipid-poly(ethylene glycol)(n): Development of Stealth Cells and Monitoring of Cell Membrane Behaviour in Serum-supplemented Conditions. J Biomed. Mater. Res, Part A, 70A/2:179-185

Frame et al (2007) Synthetic glycolipid modification of red blood cell membranes Transfusion, 47, 876-882.

Galanina et al (1997) Further refinement of the description of the ligand-binding characteristics for the galactoside-binding mistletoe lectin, a plant agglutin with immunomodulatory potency Journal of Molecular Recognition, 10, 139-147.

Haselgrübler et al (1995) Synthesis and Applications of a New Poly(ethylene glycol) Derivative for the Crosslinking of Amines with Thiols. Bioconjugate Chem, 6: 242-248

Hashimoto et al (1986) Iodacetylated and biotinylated liposomes: Effect of spacer length on sulfhydryl ligand binding and avidin precipitability. Biochim Biophys Acta, 856: 556-565.

Holmberg et al (2005) The Biotin-streptavidin interaction can be reversibly broken using water at elevated temperatures, Electrophoresis, 26 (3), 501 to 510.

Ishida et al (2001) Liposomes Bearing Polytheneglycol-Coupled Transferrin with Intracellular Targeting Property to the Solid Tumors In Vivo. Pharmaceutical Research, 18 (7): 1042-1048

Kato et al (2004) Rapid Proprotein anchoring into the membranes of mammalian cells using olial chain and polyethylene glycol derivatives.

Kinsky et al (1983) An alternative procedure for the preparation of immunogenic liposomal model membranes. J Immunol Method, 65: 295-306

Korchagina and Bovin (1992) Synthesis of spacered trisaccharides with blood group A and B specificities and fragments and structural analogues of them Soviet Journal of Bioorganic Chemistry, Vol. 18, No. 2, 153-165.

Krylov et al (2007) Stereoselective synthesis of the 3-aminopropyl glycosides of α-D-Xyl-(1→3)-β-D-Glc and α-D-Xyl-(1→3)-α-D-Xyl-(1→3)-β-D-Glc and of their corresponding N-octanoyl derivatives Synthesis, 20, 3147-3154.

Kung and Redemann (1986) Synthesis of carboxyacyl derivatives of phosphatidylethanolamine and use as an efficient method for conjugation of protein to liposomes. Biochim Biophys Acta, 862: 435-439

Lee and Lee (1997) Facile Synthesis of a High-Affinity Ligand for Mammalian Hepatic Lectin Containing Three Terminal N-Acetylgalactosamine Residues Bioconjugate Chem., 8, 762-765.

Legler et al (2004) Differential insertion of GPI-anchored GFPs into lipid rafts of live cells The FASEB Journal, Online article 10.1096/fj.03-1338fje Litherland and Mann (1938) The amino-derivatives of pentaerythritol Part I. Preparation Journal of the Chemical Society, 1588-95.

Mann and Litherland (1938) Nature, No. 3574, 789.

Mannino et al (1993) Liposomes as adjuvants for peptides: Preparation and use of immunogenic peptide-phospholipid complexes. Liposome Technology: 167-184

Martin and Papahadjopoulos (1982) Irreversible coupling of immunoglobulin fragments to preformed vesicles. An improved method for liposome targeting. J Biol Chem, 257: 286-288

Martin et al (1990) Liposomes a Practical Approach, 163-182

Massaguer et al (2001) Synthesis of RGD Containing Peptides. Comparative Study of their Incorporation to the Surface of 5-Fluoruridine Loaded Liposomes. Journal of Liposome Research, 11(I):103-113

McHugh et al (1995) Construction, purification, and functional incorporation on tumor cells of glycoplipid-anchored human B7-1 (CD80) Proc. Natl. Acad. Sci. USA, 92: 8059-8063

McNaught (1996) *Nomenclature of carbohydrates* Pure & App. Chem., 68, No. 10, 1919-2008.

Medof et al (1996) Cell-surface engineering with GPI-anchored proteins The FASEB Journal, 10: 574-586

Morandat et al (2002) Cholesterol-dependent insertion of glycosylphosphatidylinositol-anchored enzyme Biochimica et Biophysica Acta, 1564: 473-478

New (1992) Liposomes: A Practical Approach

Nifant'ev et al (1996) *Selectin-receptors 4: synthesis of tetrasaccharides sialyl Lewis A and sialyl Lewis X containing a spacer group*[1,2] J. Carbohydrate Chemistry, 15(8), 939-953.

Paulsen et al (1978) *Darstellung selektiv blockierter 2-azido-2-desoxy-$_d$-gluco-und-$_d$-galactophyranosylhalogenide: Reaktivitat and $^{13}C$-NMR-Spektren* Carbohydrate Research, 64, 339-364.

Pazynina et al (2002) *Synthesis of histo blood-group antigens A and B (type 2), xenoantigen Galα1-3Galβ1-4GlcNAc and related type 2 backbone oligosaccharides as haptens in spacered form* Mendeleev Commun. 12(4), 143-145.

Pazynina et al (2003) *Synthesis of complex 2-3 sialooligosaccharides, including sulfated and fucosylated ones, using Neu5Acα2-3Gal as a building block* Mendeleev Commun, 13(6), 245-248.

Premkumar et al (2001) Properties of Exogenously Added GPI-Anchored Proteins Following Their Incorporation Into Cells Journal of Cellular Biochemistry, 82: 234-245

Reid and Lomas-Francis (2004) The Blood Group Antigen facts book. Elsevier Academic Press, Amsterdam, 2nd ed.

Ronzon et al (2004) Insertion of Glycosylphosphatidylinositol-Anchored Enzyme into Liposomes The Journal of Membrane Biology, 197: 169-177

Shek and Heath (1983) Immune response mediated by liposome-associated protein antigens III Immunogenicity of bovine serum albumin covelantly coupled to vesicle surface. Immunology, 50: 101-106

Sherman et al (2001) *Synthesis of Neu5Ac-and Neu5Gc-α-(2→6')-lactosamine 3-aminopropyl glycosides* Carbohydrate research 330, 445-458.

Skountzou et al (2007) Incorporation of Glycosylphosphatidylinositol-Anchored Granulocyte-Macrophage Colony-Stimulating Factor or CD40 Ligand Enhances Immunogenecity of Chimeric Simian Immunodeficiency Virus-Like Particles Journal of Virology, 81, 3: 1083-1094

Vodovozova et al (2000) *Antitumour activity of cytotoxic liposomes equipped with s electin ligand SiaLe$_X$*, in a mouse mammary adenocarcinoma model European Journal of Cancer, 36, 942-949.

Winger et al (1996) Lipopeptide conjugates: biomolecular building blocks for receptor activating membrane-mimetic structures. Biomaterials, 17: 437-441

---

The invention claimed is:

1. A construct of the structure:

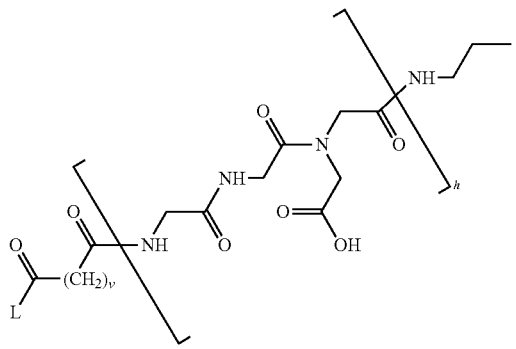
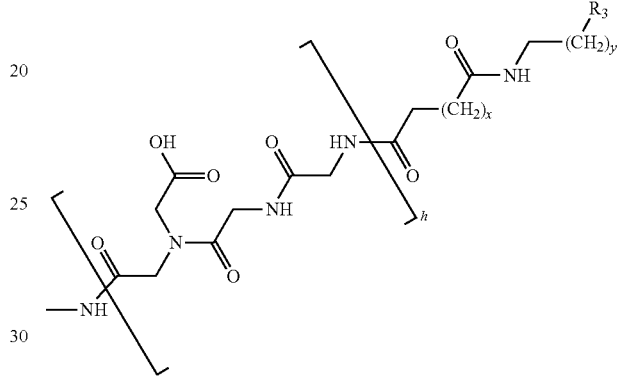

where h is the integer 1, 2, 3 or 4, v is the integer 3, 4, or 5, x is the integer 2, 3 or 4, y is the integer 1, 2 or 3, L is phosphatidylethanolamine and $R_3$ is O of a substituted hydroxyl of a glycan.

2. A construct of claim 1 of the structure:

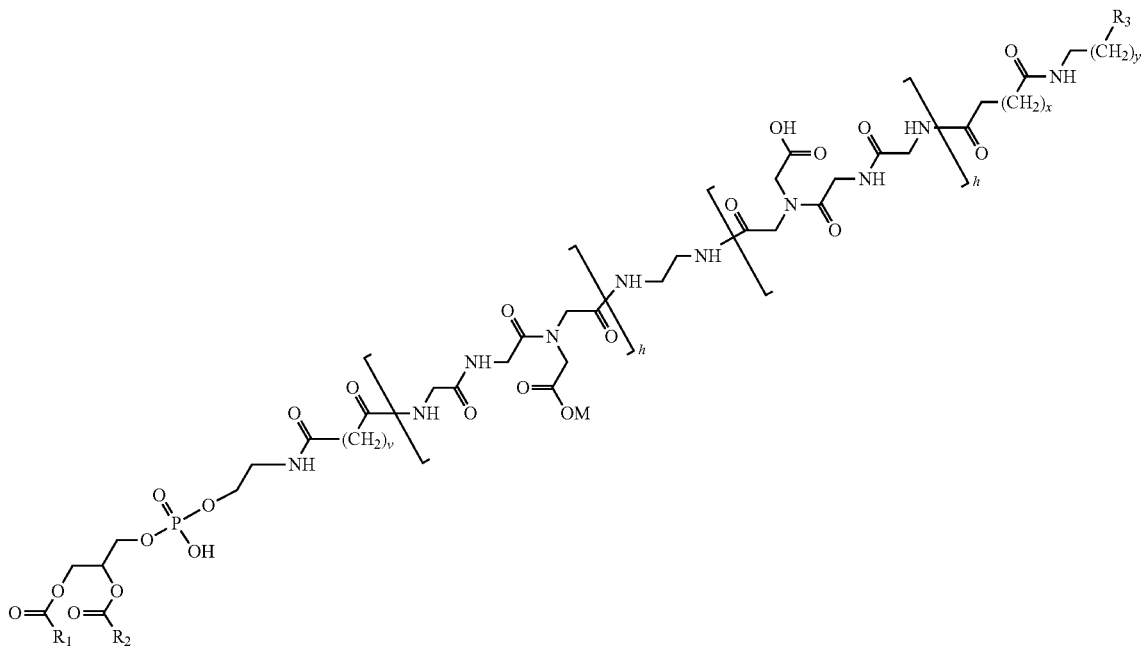

where $R_1$ and $R_2$ are independently selected from the group consisting of: alkyl or alkenyl substituents of the fatty acids trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid and cis-13-docsenoic acid.

3. A construct of claim 2 where the glycan is a glycotope.

4. A construct of claim 3 where the glycan is a trisaccharide.

5. A construct of claim 4 where h is the integer 2, x is the integer 3, and y is the integer 2.

\* \* \* \* \*